US006632645B1

(12) United States Patent
Gu et al.

(10) Patent No.: US 6,632,645 B1
(45) Date of Patent: Oct. 14, 2003

(54) **THERMOPHILIC DNA POLYMERASES FROM *THERMOACTINOMYCES VULGARIS***

(75) Inventors: Trent Gu, Madison, WI (US); Fen Huang, Madison, WI (US); James Robert Hartnett, Madison, WI (US)

(73) Assignee: Promega Corporation, Madison, WI (US)

(*) Notice: Subject to any disclaimer, the term of this patent is extended or adjusted under 35 U.S.C. 154(b) by 11 days.

(21) Appl. No.: 09/517,439

(22) Filed: Mar. 2, 2000

(51) Int. Cl.[7] .......................... C12N 9/12; C12N 15/00; C12Q 1/68; C07H 21/04

(52) U.S. Cl. ........................ 435/194; 435/6; 435/320.1; 536/23.2

(58) Field of Search ........................... 435/252.3, 320.1, 435/325, 91.1, 194; 536/23.2, 24.32

(56) References Cited

U.S. PATENT DOCUMENTS

| | | | | |
|---|---|---|---|---|
| 4,683,195 A | | 7/1987 | Mullis et al. | 435/6 |
| 4,683,202 A | | 7/1987 | Mullis | 435/91 |
| 4,707,235 A | | 11/1987 | Englert et al. | 204/182.8 |
| 4,889,818 A | | 12/1989 | Gelfand et al. | 435/194 |
| 4,965,188 A | | 10/1990 | Mullis et al. | 435/6 |
| 5,075,216 A | | 12/1991 | Innis et al. | 435/6 |
| 5,079,352 A | | 1/1992 | Gelfand et al. | 536/27 |
| 5,096,815 A | | 3/1992 | Ladner et al. | 435/69.1 |
| 5,198,346 A | | 3/1993 | Ladner et al. | 435/69.1 |
| 5,210,036 A | | 5/1993 | Comb et al. | 435/194 |
| 5,223,409 A | | 6/1993 | Ladner et al. | 435/69.7 |
| 5,322,770 A | | 6/1994 | Gelfand | 435/6 |
| 5,322,785 A | | 6/1994 | Comb et al. | 435/194 |
| 5,324,637 A | | 6/1994 | Thompson et al. | 435/68.1 |
| 5,352,600 A | | 10/1994 | Gelfand et al. | 435/194 |
| 5,436,149 A | | 7/1995 | Barnes | 435/194 |
| 5,747,298 A | | 5/1998 | Hong et al. | 435/91.1 |
| 5,830,714 A | | 11/1998 | Swaminathan et al. | 435/91.2 |
| 5,834,253 A | | 11/1998 | Hong et al. | 435/91.1 |
| 5,866,395 A | | 2/1999 | Mathur | 435/194 |
| 5,874,282 A | * | 2/1999 | Riggs et al. | 435/252.3 |
| 5,912,155 A | | 6/1999 | Chatterjee et al. | 435/194 |
| 5,939,301 A | | 8/1999 | Hughes, Jr. et al. | 435/194 |
| 5,948,663 A | | 9/1999 | Mathur | 435/194 |
| 5,968,799 A | | 10/1999 | Gelfand et al. | 435/194 |
| 6,001,645 A | | 12/1999 | Slater et al. | 435/320.1 |
| 6,008,025 A | | 12/1999 | Komatsubara et al. | 435/912 |
| 6,013,451 A | | 1/2000 | Wong et al. | 435/6 |
| 6,242,235 B1 | | 6/2001 | Shultz et al. | |

FOREIGN PATENT DOCUMENTS

| | | | |
|---|---|---|---|
| EP | 258017 | | 3/1988 |
| EP | 0 870 832 A1 | | 10/1998 |
| WO | WO 89/06691 | | 7/1989 |
| WO | WO 91/09944 | | 7/1991 |
| WO | WO 91/09950 | | 7/1991 |
| WO | WO 92/02909 | | 2/1992 |
| WO | WO 92/03556 | | 3/1992 |
| WO | WO 92/06188 | | 4/1992 |
| WO | WO 92/06200 | | 4/1992 |
| WO | WO 92/09689 | | 6/1992 |
| WO | WO 92/09690 | | 6/1992 |
| WO | WO 94/16107 | | 7/1994 |
| WO | WO 94/26766 | | 11/1994 |
| WO | WO 95/27067 | * | 10/1995 |
| WO | WO 98/14588 | | 4/1998 |
| WO | WO 99/67371 | | 12/1999 |

OTHER PUBLICATIONS

Newton, CR. PCR, Essential Data, John Wiley & Sons publishers in association with BIOS Scientific Publishers limited, pp. 38–43 and 162. Nov. 1997.*

Riley et al. Preliminary characterization of DNA–polymerases from a range of thermophilic microorganisms and bacteriophages; thermostabe DNA–polymerase purification and characterization with respect to reverse–transcriptase activity and thermostability, Dec. 1992.*

Newton, CR. PCR, Essential Data. John Wiley and Sons, New York, Nov. 1997.*

Stryer ed., *Biochemistry*, p. 17–21, 2nd ed, WH Freeman and Co. (1981).

Itakura et al., Recombinant DNA, Proc 3rd Cleveland Sympos. Macromol., Walton, ed., Elsevier, Amsterdam, pp 273–289 (1981).

Caruthers et al., Nuc. Acids Res. Symp. Ser., 7:215–233 (1980).

Matteucci and Caruthers, Tetrahedron Lett., 21:719 (1980).

Wahl, et al., Methods Enzymol. 152:399–407 (1987).

Creighton, *Proteins Structures and Molecular Principles*, W. H. Freeman and Co, New York N.Y. (1983).

Kaledin et al., Biochem., 47:1515–1521 (1982); Biokhimiya 47:1785–1791 (1982).

Davis et al., *Basic Methods in Molecular Biology* (1986).

J.G. Black, *Microbiology Principles and Applications*, 2d edition, Prentice Hall, New Jersey, p. 145–146 (1993).

T.D. Brock, "Introduction: An overview of the thermophiles," in T.D. Brock (ed.), *Thermophiles: General, Molecular and Applied Microbiology*, John Wiley & Sons, New York, 1986, pp. 1–16.

T.K. Ng and William R. Kenealy, "Industrial Application of Thermostable Enzymes," in T.D. Brock (ed.), *Thermophiles: General, Molecular, and Applied Microbiology*, 1986, John Wiley & Sons, New York, pp. 197–215.

(List continued on next page.)

*Primary Examiner*—Kenneth R. Horlick
*Assistant Examiner*—Cynthia Wilder
(74) *Attorney, Agent, or Firm*—Medlen & Carroll, LLP

(57) ABSTRACT

The present invention provides compositions comprising thermostable DNA polymerases derived from hyperthermophilic eubacteria. In particular, the present invention comprises thermostable DNA polymerases from the hyperthermophilic eubacterial species *Thermoactinomyces vulgaris*. The present invention also provides methods for utilizing naturally-occurring and non-naturally-occurring forms of *T. vulgaris* DNA polymerase in sequencing, reverse transcription, and amplification reactions.

13 Claims, 8 Drawing Sheets

OTHER PUBLICATIONS

Bessman et al. *J. Biol. Chem.* 223:171 (1957).
Buttin and Kornberg, J. Biol. Chem. 241:5419 (1966).
Joyce and Steitz, Trends Biochem. Sci., 12:288–292 (1987).
Stenesh and McGowan, Biochim. Biophys. Acta 475:32–44 (1977).
Stenesh and Roe, Biochim, Biophys. Acta 272:156–166 (1972).
Low et al., J. Biol. Chem., 251:1311 (1976).
Ott et al., J. Bacteriol., 165:951 (1986).
Harwood et al., J. Biol. Chem., 245:5614 (1970).
Hamilton and Grossman, Biochem. 13:1885 (1974).
Lopez et al., J. Biol. Chem., 264:4255 (1989).
Engler and Bessman, Cold Spring Harbor Symp., 43:929 (1979).
Barr et al., Biotechniques 4:428 (1986).
Kaledin et al., Biochem. 45:494–501 (1980) Biokhimiya 45:644–651 (1980).
Chien et al., J. Bacteriol., 127:1550 (1976).
University of Cincinnati Master's thesis by A. Chien, "Purification and Characterization of DNA Polymerase from *Thermus aquaticus*," (1976).
University of Cincinnati, Master's thesis by D. B. Edgar, "DNA Polymerase From an Extreme Thermophile: *Thermus aquaticus*," (1974).
Simpson et al., Biochem. Cell Biol., 68:1292–1296 (1990).
Myers and Gelfand, Biochem., 30:7661 (1991).
Bechtereva et al., Nucleic Acids Res., 17:10507 (1989).
Glukhov et al., Mol. Cell. Probes 4:435–443 (1990).
Carballeira et al., BioTech., 9:276–281 (1990).
Rüttiman et al., Eur. J. Biochem., 149:41–46 (1985).
Oshima et al., J. Biochem., 75:179–183 (1974).
Sakaguchi and Yajima, Fed. Proc., 33:1492 (1974) (abstract).
Kaledin et al., Biochem., 46:1247–1254 (1981); Biokhimiya 46:1576–1584 (1981).
Mizusawa et al., Nucl. Acids Res. 14:1319 (1986).
Kaledin et al., Biochem., 47:1515–1521 (1982); Biokhimiya 47:1785–1791 (1982).
Sanger et al., Proc. Natl. Acad. Sci. USA 74:5463 (1977).
Hamal et al., Eur. J. Biochem., 190:517–521 (1990).
Salhi et al., Biochem. Biophys. Res. Comm., 167:1341–1347 (1990).
Salhi et al., J. Mol. Biol., 209:635–641 (1989).
Rella et al., Ital. J. Biochem., 39:83–99 (1990).
Forterre et al., Can. J. Microbiol., 35:228–233 (1989).
Rossi et al., System. Appl. Microbiol., 7:337–341 (1986).
Klimczak et al., Nucleic Acids Res., 13:5269–5282 (1985).
Elie et al., Biochim. Biophys. Acta 951:261–267 (1988).
Sellmann et al., J. Bacteriol., 174:4350–4355 (1992).
Kaboev et al., J. Bacteriol., 145:21–26 (1981).
Klimczak et al., Biochem., 25:4850–4855 (1986).
Kong et al., J. Biol. Chem. 268:1965 (1993).
Lundberg et al., Gene 108:1 (1991).
A.T. Bankier, "Dideoxy sequencing reactions using Klenow fragment DNA polymerase I," in H. and A. Griffin (eds.), *Methods in Molecular Biology: DNA Sequencing Protocols*, Humana Press, Totowa, NJ, 1993, pp. 83–90.
Lawyer et al., J. BIol. Chem., 264:6427–6437 (1989).
Lawyer et al., PCR Meth. Appl., 2:275–287 (1993).
Sambrook et al., 1989, *Nucleic Acid Hybridization, A Practical Approach*, IRL Press, Washington D.C. (1985).
Anderson and Young, Quantitative Filter Hybridization, in *Nucleic Acid Hydribization* (1985).
C.R. Newton et al., *PCR*, 2nd Ed., Springer–Verlag (New York, 1997), p. 24.
Maniatis, et al., Science 236:1237 (1987).
Voss, et al., Trends Biochem. Sci., 11:287 (1986).
Dijkema et al., EMBO J. 4:761 (1985).
Uetsuki et al., J. Biol. Chem., 264:5791 (1989).
Mizushima and Nagata, Nuc. Acids. Res., 18:5322 (1990).
Gorman et al., Proc. Natl. Acad. Sci. USA 79:6777 (1982).
Boshart, et al., Cell 41:521 (1985).
Kim, et al., Gene 91:217 (1990).
Sambrook, et al., *Molecular Cloning: A Laboratory Manual*, 2nd ed., Cold Spring Harbor Laboratory Press, New York [1989] pp. 16.7–16.8.
Kornberg, *DNA Replication*, W.H. Freeman and Co., San Francisco, pp. 127–139 (1980).
Tindall and Kunkell, Biochem. 27:6008 (1988).
Brutlag et al., Biochem. Biophys. Res. Commun. 37:982 (1969).
Erlich et al., Science 252:1643 (1991).
Bebenek et al., J. Biol. Chem. 265:13878 (1990).
Barnes, Gene 112:29 (1992).
Bernard et al. Cell 59:219 (1989.
Wahl, et al., Methods Enzymol. 152:399–407 (1987).
Davis et al., *Basic Methods in Molecular Biology* (1986).
Ben–Bassat et al., J. Bacteriol. 169:751–757 (1987).
Miller et al., PNAS 84:2718–1722 (1990).
Stryer ed., *Biochemistry*, pp. 17–21, 2nd ed, WH Freeman and Co. (1981).
Narang, Tetrahedron 39:39 (1983).
Itakura et al., Recombinant DNA, Proc 3rd Cleveland Sympos. Macromol., Walton, ed., Elsevier, Amsterdam, pp 273–289 (1981).
Itakura et al., Annu. Rev. Biochem. 53:323, 1984.
Ike et al., Nucleic Acid Res. 11:477 (1983).
Scott et al., Science 249:386–390 (1980).
Roberts et al., PNAS 89:2429–2433 (1992).
Devlin et al., Science 249: 404–406 (1990;).
Cwirla et al., PNAS 87: 6378–6382 (1990).
Marks et al., J. Biol. Chem., 267:16007–16010 (1992).
Griffths et al., EMBO J., 12:725–734 (1993).
Clackson et al., Nature, 352:624–628 (1991).
Barbas et al., PNAS 89:4457–4461 (1992).
Ruf et al., Biochem., 33:1565–1572 (1994).
Wang et al., J. Biol. Chem., 269:3095–3099 (1994).
Balint et al. Gene 137:109–118 (1993).
Grodberg et al., Eur. J. Biochem., 218:597–601 (1993).
Nagashima et al., J. Biol. Chem., 268:2888–2892 (1993).
Lowman et al., Biochem., 30:10832–10838 (1991).
Cunningham et al., Science, 244:1081–1085 (1989).
Gustin et al., Virol., 193:653–660 (1993).
Brown et al., Mol. Cell. Biol., 12:2644–2652 (1992).
McKnight et al., Science, 232:316.
Meyers et al.,Science, 232:613 (1986).
Caruthers et al., Nuc. Acids Res. Symp. Ser., 7:215–233 (1980).
Crea and Horn, Nuc. Acids Res., 9:2331 (1980).
Matteucci and Caruthers, Tetrahedron Lett., 21:719 (1980).
Chow and Kempe, Nuc.Acids Res., 9;2807–2817 (1981).
Creighton, *Proteins Structures and Molecular Principles*, W H Freeman and Co, New York N.Y. (1983).
Roberge et al., Science 269:202–204 (1995).
Innis et al., Proc. Natl. Acad Sci USA 85:9436 (1988).
Maxam and Gilbert, Proc. Natl. Acad. Sci. USA 74:560 (1977).

Itakura et al., Science 198:1056 (1984).
Riley et al., Thermophiles Science Technology pp. 1–11 (1992).
Sanger et al., Proc. Natl. Acad. Sci. USA 74:5463 (1977).
Kaledin et al., Biokhimiya 45:494 (1980).
Mizusawa et al., Nucl. Acids Res. 14:1319 (1986).

* cited by examiner

FIGURE 2

| | Exo I | | Exo II | | Exo III |
|---|---|---|---|---|---|
| *Bsu* Pol III | 419 | ETYV-VFDVETTGLSAVY | 502 | LVAHN-A-SFDMGFLN | 552 | TLCKKF-DIELTQH |
| *Eco* Pol III ε | 6 | TRQI-VLDTETTGMNQIG | 95 | LVIHN-AA-FDIGFMD | 147 | ALCARY-EIDNSKR |
| ØT4 | 182 | RVIYMPFDNERDMLMEYI | 210 | FTGWNI-EGFDVPYIM | 332 | DKIRGF--IDLVLS |
| ØT7 | 1 | ---MIVSDIEANALLESV | 57 | V-FHNGH-KYDVPALT | 165 | EEMMDYNVQDVVVT |
| *Eco* Pol I | 348 | KAPVFAFDTETDSLDNIS | 417 | V-GQNL--KYDRGILA | 492 | EEAGRYAAEDADVT |
| *Tma* | 316 | ESPSFAIDLETSSLDPFD | 382 | V-GQNL--KFDYKVLM | 459 | EKAANYSCEDADIT |
| *Tne* | 316 | EVPSFALDLETSSLDPFN | 382 | V-GQNL--KYDYKVLM | 459 | DKAANYSCEDADIT |

Figure 3
Nucleotide sequence of full-length *Tvu* DNA polymerase (SEQ ID NO: 1)

```
TTGAAAAACA AGCTCGTCTT AATTGACGGC AACAGCGTGG CGTACCGCGC   50
CTTTTTCGCG TTGCCGCTTT TGCATAACGA TAAAGGGATT CATACGAACG  100
CAGTCTACGG GTTTACGATG ATGTTAAACA AAATTTTGGC GGAAGAGCAG  150
CCGACCCACA TTCTCGTGGC GTTTGACGCC GGGAAAACGA CGTTCCGCCA  200
TGAAACGTTC CAAGACTATA AAGGCGGGCG GCAGCAGACG CCGCCGGAAC  250
TGTCGGAACA GTTTCCGCTG CTGCGCGAAT TGCTCAAGGC GTACCGCATC  300
CCCGCCTATG AGCTCGACCA TTACGAAGCG GACGATATTA TCGGAACGAT  350
GGCGGCGCGG GCTGAGCGGG AAGGGTTTGC AGTGAAAGTC ATTTCCGGCG  400
ACCGCGATTT AACCCAGCTT GCTTCCCCGC AAGTGACGGT GGAGATTACG  450
AAAAAAGGGA TTACCGACAT CGAGTCGTAC ACGCCGGAGA CGGTCGCGGA  500
AAAATACGGC CTCACCCCGG AGCAAATTGT CGACTTGAAA GGATTGATGG  550
GCGACAAATC CGACAACATC CCCGGCGTGC CCGGCATCGG GGAAAAAACA  600
GCCGTCAAGC TGCTCAAGCA ATTCGGCACG GTCGAAAACG TACTGGCATC  650
GATCGATGAG ATCAAAGGGG AGAAGCTGAA AGAAAATTTG CGCCAATACC  700
GGGATTTGGC GCTTTTAAGC AAACAGCTGG CCGCCATTCG CCGCGACGCC  750
CCAGTTGAGC TGACGCTCGA TGACATTGTC TACAAAGGAG AAGACCGGGA  800
AAAAGTGGTC GCCTTATTTA AGGAGCTCGG GTTCCAGTCG TTTCTCGACA  850
AGATGGCCGT CCAAACGGAT GAAGGCGAGA AGCCGCTCGC CGGGATGGAC  900
TTTGCGATCG CCGACGGCGT CACGGACGAA ATGCTCGCCG ACAAGGCGGC  950
CCTCGTCGTG GAGGTGGTGG GCGACAACTA TCACCATGCC CCGATTGTCG 1000
GGATCGCCTT GGCCAACGAA CGCGGGCGGT TTTTCCTGCG CCCGGAGACG 1050
GCGCTCGCCG ATCCGAAATT TCTCGCTTGG CTTGGCGATG AGACGAAGAA 1100
AAAAACGATG TTTGATTCAA AGCGGGCGGC CGTCGCGTTA AAATGGAAAG 1150
GAATCGAACT GCGCGGCGTC GTGTTCGATC TGTTGCTGGC CGCTTACTTG 1200
CTCGATCCGG CGCAGGCGGC GGGCGACGTT GCCGCGGTGG CGAAAATGCA 1250
TCAGTACGAG GCGGTGCGGT CGGATGAGGC GGTCTATGGA AAAGGAGCGA 1300
AGCGGACGGT TCCTGATGAA CCGACGCTTG CCGAGCATCT CGCCCGCAAG 1350
GCGGCGGCCA TTTGGGCGCT TGAAGAGCCG TTGATGGACG AACTGCGCCG 1400
CAACGAACAA GATCGGCTGC TGACCGAGCT CGAACAGCCG CTGGCTGGCA 1450
TTTTGGCCAA TATGGAATTT ACTGGAGTGA AAGTGGACAC GAAGCGGCTT 1500
GAACAGATGG GGGCGGAGCT CACCGAGCAG CTGCAGGCGG TCGAGCGGCG 1550
CATTTACGAA CTCGCCGGCC AAGAGTTCAA CATTAACTCG CCGAAACAGC 1600
TCGGGACGGT TTTATTTGAC AAGCTGCAGC TCCCGGTGTT GAAAAAGACA 1650
AAAACCGGCT ATTCGACTTC AGCCGATGTG CTTGAGAAGC TTGCACCGCA 1700
CCATGAAATC GTCGAACATA TTTTGCATTA CCGCCAACTC GGCAAGCTGC 1750
AGTCAACGTA TATTGAAGGG CTGCTGAAAG TGGTGCACCC CGTGACGGGC 1800
AAAGTGCACA CGATGTTCAA TCAGGCGTTG ACGCAAACCG GGCGCCTCAG 1850
CTCCGTCGAA CCGAATTTGC AAAACATTCC GATTCGGCTT GAGGAAGGGC 1900
GGAAAATCCG CCAGGCGTTC GTGCCGTCGG AGCCGGACTG GCTCATCTTT 1950
GCGGCCGACT ATTCGCAAAT CGAGCTGCGC GTCCTCGCCC ATATCGCGGA 2000
AGATGACAAT TTGATTGAAG CGTTCCGGCG CGGGTTGGAC ATCCATACGA 2050
AAACAGCCAT GGACATTTTC CATGTGAGCG AAGAAGACGT GACAGCCAAC 2100
ATGCGCCGCC AAGCGAAGGC CGTCAATTTT GGCATCGTGT ACGGCATTAG 2150
TGATTACGGT CTGGCGCAAA ACTTGAACAT TACGCGCAAA GAAGCGGCTG 2200
AATTTATTGA GCGATATTTT GCCAGTTTTC CAGGTGTAAA GCAATATATG 2250
GACAACACTG TGCAAGAAGC GAAACAAAAA GGGTATGTGA CGACGCTGCT 2300
GCATCGGCGC CGCTATTTGC CCGATATTAC AAGCCGCAAC TTCAACGTCC 2350
GCAGCTTCGC CGAGCGGACG GCGATGAACA CACCGATTCA AGGGAGCGCC 2400
GCTGATATTA TTAAAAAAGC GATGATCGAT CTAAGCGTGA GGCTGCGCGA 2450
AGAACGGCTG CAGGCGCGCC TGTTGCTGCA AGTGCATGAC GAACTCATTT 2500
TGGAGGCGCC GAAAGAGGAA ATCGAGCGGC TGTGCCGCCT CGTTCCAGAG 2550
GTGATGGAGC AAGCCGTCGC ACTCCGCGTG CCGCTGAAAG TCGATTACCA 2600
TTACGGTCCG ACGTGGTACG ACGCCAAATA A                    2631
```

Figure 4
Amino Acid Sequence of Full-length Tvu DNA Polymerase (SEQ ID NO: 2)

```
LKNKLVLIDG NSVAYRAFFA LPLLHNDKGI HTNAVYGFTM MLNKILAEEQ   50
PTHILVAFDA GKTTFRHETF QDYKGGRQQT PPELSEQFPL LRELLKAYRI  100
PAYELDHYEA DDIIGTMAAR AEREGFAVKV ISGDRDLTQL ASPQVTVEIT  150
KKGITDIESY TPETVAEKYG LTPEQIVDLK GLMGDKSDNI PGVPGIGEKT  200
AVKLLKQFGT VENVLASIDE IKGEKLKENL RQYRDLALLS KQLAAIRRDA  250
PVELTLDDIV YKGEDREKVV ALFKELGFQS FLDKMAVQTD EGEKPLAGMD  300
FAIADGVTDE MLADKAALVV EVVGDNYHHA PIVGIALANE RGRFFLRPET  350
ALADPKFLAW LGDETKKKTM FDSKRAAVAL KWKGIELRGV VFDLLLAAYL  400
LDPAQAAGDV AAVAKMHQYE AVRSDEAVYG KGAKRTVPDE PTLAEHLARK  450
AAAIWALEEP LMDELRRNEQ DRLLTELEQP LAGILANMEF TGVKVDTKRL  500
EQMGAELTEQ LQAVERRIYE LAGQEFNINS PKQLGTVLFD KLQLPVLKKT  550
KTGYSTSADV LEKLAPHHEI VEHILHYRQL GKLQSTYIEG LLKVVHPVTG  600
KVHTMFNQAL TQTGRLSSVE PNLQNIPIRL EEGRKIRQAF VPSEPDWLIF  650
AADYSQIELR VLAHIAEDDN LIEAFRRGLD IHTKTAMDIF HVSEEDVTAN  700
MRRQAKAVNF GIVYGISDYG LAQNLNITRK EAAEFIERYF ASFPGVKQYM  750
DNTVQEAKQK GYVTTLLHRR RYLPDITSRN FNVRSFAERT AMNTPIQGSA  800
ADIIKKAMID LSVRLREERL QARLLLQVHD ELILEAPKEE IERLCRLVPE  850
VMEQAVALRV PLKVDYHYGP TWYDAK                            876
```

Figure 5
Nucleotide Sequence of M285 (SEQ ID NO: 3)

```
ATGGCCGTCC AAACGGATGA AGGCGAGAAG CCGCTCGCCG GGATGGACTT   50
TGCGATCGCC GACGGCGTCA CGGACGAAAT GCTCGCCGAC AAGGCGGCCC  100
TCGTCGTGGA GGTGGTGGGC GACAACTATC ACCATGCCCC GATTGTCGGG  150
ATCGCCTTGG CCAACGAACG CGGGCGGTTT TTCCTGCGCC CGGAGACGGC  200
GCTCGCCGAT CCGAAATTTC TCGCTTGGCT TGGCGATGAG ACGAAGAAAA  250
AAACGATGTT TGATTCAAAG CGGGCGGCCG TCGCGTTAAA ATGGAAAGGA  300
ATCGAACTGC GCGGCGTCGT GTTCGATCTG TTGCTGGCCG CTTACTTGCT  350
CGATCCGGCG CAGGCGGCGG GCGACGTTGC CGCGGTGGCG AAAATGCATC  400
AGTACGAGGC GGTGCGGTCG GATGAGGCGG TCTATGGAAA AGGAGCGAAG  450
CGGACGGTTC CTGATGAACC GACGCTTGCC GAGCATCTCG CCCGCAAGGC  500
GGCGGCCATT TGGGCGCTTG AAGAGCCGTT GATGGACGAA CTGCGCCGCA  550
ACGAACAAGA TCGGCTGCTG ACCGAGCTCG AACAGCCGCT GGCTGGCATT  600
TTGGCCAATA TGGAATTTAC TGGAGTGAAA GTGGACACGA AGCGGCTTGA  650
ACAGATGGGG GCGGAGCTCA CCGAGCAGCT GCAGGCGGTC GAGCGGCGCA  700
TTTACGAACT CGCCGGCCAA GAGTTCAACA TTAACTCGCC GAAACAGCTC  750
GGGACGGTTT TATTTGACAA GCTGCAGCTC CCGGTGTTGA AAAAGACAAA  800
AACCGGCTAT TCGACTTCAG CCGATGTGCT TGAGAAGCTT GCACCGCACC  850
ATGAAATCGT CGAACATATT TTGCATTACC GCCAACTCGG CAAGCTGCAG  900
TCAACGTATA TTGAAGGGCT GCTGAAAGTG GTGCACCCCG TGACGGGCAA  950
AGTGCACACG ATGTTCAATC AGGCGTTGAC GCAAACCGGG CGCCTCAGCT 1000
CCGTCGAACC GAATTTGCAA AACATTCCGA TTCGGCTTGA GGAAGGGCGG 1050
AAAATCCGCC AGGCGTTCGT GCCGTCGGAG CCGGACTGGC TCATCTTTGC 1100
GGCCGACTAT TCGCAAATCG AGCTGCGCGT CCTCGCCCAT ATCGCGGAAG 1150
ATGACAATTT GATTGAAGCG TTCCGGCGCG GGTTGGACAT CCATACGAAA 1200
ACAGCCATGG ACATTTTCCA TGTGAGCGAA GAAGACGTGA CAGCCAACAT 1250
GCGCCGCCAA GCGAAGGCCG TCAATTTTGG CATCGTGTAC GGCATTAGTG 1300
ATTACGGTCT GGCGCAAAAC TTGAACATTA CGCGCAAAGA AGCGGCTGAA 1350
TTTATTGAGC GATATTTTGC CAGTTTTCCA GGTGTAAAGC AATATATGGA 1400
CAACACTGTG CAAGAAGCGA AACAAAAAGG GTATGTGACG ACGCTGCTGC 1450
ATCGGCGCCG CTATTTGCCC GATATTACAA GCCGCAACTT CAACGTCCGC 1500
AGCTTCGCCG AGCGGACGGC GATGAACACA CCGATTCAAG GGAGCGCCGC 1550
TGATATTATT AAAAAAGCGA TGATCGATCT AAGCGTGAGG CTGCGCGAAG 1600
AACGGCTGCA GGCGCGCCTG TTGCTGCAAG TGCATGACGA ACTCATTTTG 1650
GAGGCGCCGA AAGAGGAAAT CGAGCGGCTG TGCCGCCTCG TTCCAGAGGT 1700
GATGGAGCAA GCCGTCGCAC TCCGCGTGCC GCTGAAAGTC GATTACCATT 1750
ACGGTCCGAC GTGGTACGAC GCCAAATAA                        1779
```

Figure 6
Amino Acid Sequence of M285 (SEQ ID NO: 4)

```
MAVQTDEGEK PLAGMDFAIA DGVTDEMLAD KAALVVEVVG DNYHHAPIVG   50
IALANERGRF FLRPETALAD PKFLAWLGDE TKKKTMFDSK RAAVALKWKG  100
IELRGVVFDL LLAAYLLDPA QAAGDVAAVA KMHQYEAVRS DEAVYGKGAK  150
RTVPDEPTLA EHLARKAAAI WALEEPLMDE LRRNEQDRLL TELEQPLAGI  200
LANMEFTGVK VDTKRLEQMG AELTEQLQAV ERRIYELAGQ EFNINSPKQL  250
GTVLFDKLQL PVLKKTKTGY STSADVLEKL APHHEIVEHI LHYRQLGKLQ  300
STYIEGLLKV VHPVTGKVHT MFNQALTQTG RLSSVEPNLQ NIPIRLEEGR  350
KIRQAFVPSE PDWLIFAADY SQIELRVLAH IAEDDNLIEA FRRGLDIHTK  400
TAMDIFHVSE EDVTANMRRQ AKAVNFGIVY GISDYGLAQN LNITRKEAAE  450
FIERYFASFP GVKQYMDNTV QEAKQKGYVT TLLHRRRYLP DITSRNFNVR  500
SFAERTAMNT PIQGSAADII KKAMIDLSVR LREERLQARL LLQVHDELIL  550
EAPKEEIERL CRLVPEVMEQ AVALRVPLKV DYHYGPTWYD AK          592
```

Figure 7
Nucleotide Sequence of T289M (SEQ ID NO: 5)

```
ATGGATGAAG GCGAGAAGCC GCTCGCCGGG ATGGACTTTG CGATCGCCGA   50
CGGCGTCACG GACGAAATGC TCGCCGACAA GGCGGCCCTC GTCGTGGAGG  100
TGGTGGGCGA CAACTATCAC CATGCCCCGA TTGTCGGGAT CGCCTTGGCC  150
AACGAACGCG GGCGGTTTTT CCTGCGCCCG GAGACGGCGC TCGCCGATCC  200
GAAATTTCTC GCTTGGCTTG GCGATGAGAC GAAGAAAAAA ACGATGTTTG  250
ATTCAAAGCG GGCGGCCGTC GCGTTAAAAT GGAAAGGAAT CGAACTGCGC  300
GGCGTCGTGT TCGATCTGTT GCTGGCCGCT TACTTGCTCG ATCCGGCGCA  350
GGCGGCGGGC GACGTTGCCG CGGTGGCGAA AATGCATCAG TACGAGGCGG  400
TGCGGTCGGA TGAGGCGGTC TATGGAAAAG GAGCGAAGCG GACGGTTCCT  450
GATGAACCGA CGCTTGCCGA GCATCTCGCC CGCAAGGCGG CGGCCATTTG  500
GGCGCTTGAA GAGCCGTTGA TGGACGAACT GCGCCGCAAC GAACAAGATC  550
GGCTGCTGAC CGAGCTCGAA CAGCCGCTGG CTGGCATTTT GGCCAATATG  600
GAATTTACTG GAGTGAAAGT GGACACGAAG CGGCTTGAAC AGATGGGGGC  650
GGAGCTCACC GAGCAGCTGC AGGCGGTCGA GCGGCGCATT TACGAACTCG  700
CCGGCCAAGA GTTCAACATT AACTCGCCGA AACAGCTCGG GACGGTTTTA  750
TTTGACAAGC TGCAGCTCCC GGTGTTGAAA AAGACAAAAA CCGGCTATTC  800
GACTTCAGCC GATGTGCTTG AGAAGCTTGC ACCGCACCAT GAAATCGTCG  850
AACATATTTT GCATTACCGC CAACTCGGCA AGCTGCAGTC AACGTATATT  900
GAAGGGCTGC TGAAAGTGGT GCACCCCGTG ACGGGCAAAG TGCACACGAT  950
GTTCAATCAG GCGTTGACGC AAACCGGGCG CCTCAGCTCC GTCGAACCGA 1000
ATTTGCAAAA CATTCCGATT CGGCTTGAGG AAGGGCGGAA AATCCGCCAG 1050
GCGTTCGTGC CGTCGGAGCC GGACTGGCTC ATCTTTGCGG CCGACTATTC 1100
GCAAATCGAG CTGCGCGTCC TCGCCCATAT CGCGGAAGAT GACAATTTGA 1150
TTGAAGCGTT CCGGCGCGGG TTGGACATCC ATACGAAAAC AGCCATGGAC 1200
ATTTTCCATG TGAGCGAAGA AGACGTGACA GCCAACATGC GCCGCCAAGC 1250
GAAGGCCGTC AATTTTGGCA TCGTGTACGG CATTAGTGAT TACGGTCTGG 1300
CGCAAAACTT GAACATTACG CGCAAAGAAG CGGCTGAATT TATTGAGCGA 1350
TATTTTGCCA GTTTTCCAGG TGTAAAGCAA TATATGGACA ACACTGTGCA 1400
AGAAGCGAAA CAAAAAGGGT ATGTGACGAC GCTGCTGCAT CGGCGCCGCT 1450
ATTTGCCCGA TATTACAAGC CGCAACTTCA ACGTCCGCAG CTTCGCCGAG 1500
CGGACGGCGA TGAACACACC GATTCAAGGG AGCGCCGCTG ATATTATTAA 1550
AAAAGCGATG ATCGATCTAA GCGTGAGGCT GCGCGAAGAA CGGCTGCAGG 1600
CGCGCCTGTT GCTGCAAGTG CATGACGAAC TCATTTTGGA GGCGCCGAAA 1650
GAGGAAATCG AGCGGCTGTG CCGCCTCGTT CCAGAGGTGA TGGAGCAAGC 1700
CGTCGCACTC CGCGTGCCGC TGAAAGTCGA TTACCATTAC GGTCCGACGT 1750
GGTACGACGC CAAATAA                                     1767
```

Figure 8
Amino Acid Sequence of T289M (SEQ ID NO: 6)

```
TDEGEKPLAG MDFAIADGVT DEMLADKAAL VVEVVGDNYH HAPIVGIALA  50
NERGRFFLRP ETALADPKFL AWLGDETKKK TMFDSKRAAV ALKWKGIELR 100
GVVFDLLLAA YLLDPAQAAG DVAAVAKMHQ YEAVRSDEAV YGKGAKRTVP 150
DEPTLAEHLA RKAAAIWALE EPLMDELRRN EQDRLLTELE QPLAGILANM 200
EFTGVKVDTK RLEQMGAELT EQLQAVERRI YELAGQEFNI NSPKQLGTVL 250
FDKLQLPVLK KTKTGYSTSA DVLEKLAPHH EIVEHILHYR QLGKLQSTYI 300
EGLLKVVHPV TGKVHTMFNQ ALTQTGRLSS VEPNLQNIPI RLEEGRKIRQ 350
AFVPSEPDWL IFAADYSQIE LRVLAHIAED DNLIEAFRRG LDIHTKTAMD 400
IFHVSEEDVT ANMRRQAKAV NFGIVYGISD YGLAQNLNIT RKEAAEFIER 450
YFASFPGVKQ YMDNTVQEAK QKGYVTTLLH RRRYLPDITS RNFNVRSFAE 500
RTAMNTPIQG SAADIIKKAM IDLSVRLREE RLQARLLLQV HDELILEAPK 550
EEIERLCRLV PEVMEQAVAL RVPLKVDYHY GPTWYDAK             588
```

THERMOPHILIC DNA POLYMERASES FROM *THERMOACTINOMYCES VULGARIS*

FIELD OF THE INVENTION

The present invention relates to thermostable DNA polymerases derived from the thermophilic eubacterial species *Thermoactinomyces vulgaris*, as well as means for isolating and producing these enzymes. The thermostable DNA polymerases of the present invention are useful in many recombinant DNA techniques, including thermal cycle sequencing, nucleic acid amplification and reverse transcription.

BACKGROUND

Thermophilic bacteria are organisms which are capable of growth at elevated temperatures. Unlike the mesophiles, which grow best at temperatures in the range of 25–40° C., or psychrophiles, which grow best at temperatures in the range of 15–20° C., thermophiles grow best at temperatures greater than 50° C. Indeed, some thermophiles grow best at 65–75° C., and some of the hyperthermophiles grow at temperatures up to 130° C. (e.g., J. G. Black, *Microbiology Principles and Applications*, 2d edition, Prentice Hall, N.J., 1993, p. 145–146).

The thermophilic bacteria encompass a wide variety of genera and species. There are thermophilic representatives included within the phototrophic bacteria (i.e., the purple bacteria, green bacteria, and cyanobacteria), eubacteria (i.e., Bacillus, Clostridium, Thiobacillus, Desulfotomaculum, Thermus, lactic acid bacteria, actinomycetes, spirochetes, and numerous other genera), and the archaebacteria (i.e., Pyrococcus, Thermococcus, Thermoplasma, Thermotoga, Sulfolobus, and the methanogens). There are aerobic, as well as anaerobic thermophilic organisms. Thus, the environments in which thermophiles may be isolated vary greatly, although all of these organisms are isolated from areas associated with high temperatures. Natural geothermal habitats have a worldwide distribution and are primarily associated with tectonically active zones where major movements of the earth's crust occur. Thermophilic bacteria have been isolated from all of the various geothermal habitats, including boiling springs with neutral pH ranges, sulfur-rich acidic springs, and deep-sea vents. In general, the organisms are optimally adapted to the temperatures at which they are living in these geothemal habitats (T. D. Brock, "Introduction: An overview of the thermophiles," in T. D. Brock (ed.), *Thermophiles: General, Molecular and Applied Microbiology*, John Wiley & Sons, New York, 1986, pp. 1–16). Basic, as well as applied research on thermophiles has provided some insight into the physiology of these organisms, as well as use of these organisms in industry and biotechnology.

I. Uses For Thermophilic Enzymes

Advances in molecular biology and industrial processes have led to increased interest in thermophilic organisms. Of particular interest has been the development of thermophilic enzymes for use in industries such as the detergent, flavor-enhancing, and starch industries. Indeed, the cost savings associated with longer storage stability and higher activity at higher temperatures of thermophilic enzymes, as compared to mesophilic enzymes, provide good reason to select and develop thermophilic enzymes for industrial and biotechnology applications. Thus, there has been much research conducted to characterize enzymes from thermophilic organisms. However, some thermophilic enzymes have less activity than their mesophilic counterparts under similar conditions at the elevated temperatures used in industry (typically temperatures in the range of 50–100° C.) (T. K. Ng and William R. Kenealy, "Industrial Applications of Thermostable Enzymes," in T. D. Brock (ed.), *Thermophiles: General, Molecular, and Applied Microbiology*, 1986, John Wiley & Sons, New York, pp. 197–215). Thus, the choice of a thermostable enzyme over a mesophilic one may not be as beneficial as originally assumed. However, much research remains to be done to characterize and compare thermophilic enzymes of importance (e.g., polymerases, ligases, kinases, topoisomerases, restriction endonucleases, etc.) in areas such as molecular biology .

II. Thermophilic DNA Polymerases

Extensive research has been conducted on isolation of DNA polymerases from mesophilic organisms such as *E. coli*. (e.g., Bessman et al., J. Biol. Chem. 223:171,1957; Buttin and Kornberg, J. Biol. Chem. 241:5419, 1966; and Joyce and Steitz, Trends Biochem. Sci., 12:288–292, 1987). Other mesophilic polymerases have also been studied, such as those of *Bacillus licheniformis* (Stenesh and McGowan, Biochim. Biophys. Acta 475:32–44, 1977; Stenesh and Roe, Biochim. Biophys. Acta 272:156–166, 1972); *Bacillus subtilis* (Low et al., J. Biol. Chem., 251:1311, 1976; and Ott et al., J. Bacteriol., 165:951, 1986); *Salmonella typhimurium* (Harwood et al., J. Biol. Chem., 245:5614, 1970; Hamilton and Grossman, Biochem., 13:1885, 1974); *Streptococcus pneumoniae* (Lopez et al., J. Biol. Chem., 264:4255, 1989); and *Micrococcus luteus* (Engler and Bessman, Cold Spring Harbor Symp., 43:929, 1979), to name but a few.

Somewhat less investigation has been performed on the isolation and purification of DNA polymerases from thermophilic organisms. However, native (i.e., non-recombinant) and/or recombinant thermostable DNA polymerases have been purified from various organisms, as shown in Table 1 below.

TABLE 1

Polymerase Isolation From Thermophilic Organisms

| Organism | Citation |
|---|---|
| *Thermus aquaticus* | Kaledin et al., Biochem., 45:494–501 (1980); Biokhimiya 45:644–651 (1980). |
| | Chien et al., J. Bacteriol., 127:1550 (1976). |
| | University of Cincinnati Master's thesis by A. Chien, "Purification and Characterization of DNA Polymerase from *Thermus aquaticus,*" (1976). |
| | University of Cincinnati, Master's thesis by D. B. Edgar, "DNA Polymerase From an Extreme Thermophile: *Thermus aquaticus,*" (1974). |
| | U.S. Pat. No. 4,889,818* |
| | U.S. Pat. No. 5,352,600* |
| | U.S. Pat. No. 5,079,352* |
| | European Patent Pub. No. 258,017* |
| | PCT Pub. No. WO 94/26766* |
| | PCT Pub. No. WO 92/06188* |
| | PCT Pub. No. WO 89/06691* |
| *Thermatoga maritima* | PCT Pub. No. WO 92/03556* |
| *Thermatoga neapolitana* | U.S. Pat. No. 5,912,155* |
| | U.S. Pat. No. 5,939,301* |
| | U.S. Pat. No. 6,001,645* |
| Thermotoga strain FjSS3-B.1 | Simpson et al., Biochem. Cell Biol., 68:1292–1296 (1990). |
| *Thermosipho* | PCT Pub. No. 92/06200* |

TABLE 1-continued

Polymerase Isolation From Thermophilic Organisms

| Organism | Citation |
|---|---|
| *africanus* | U.S. Pat. No. 5,968,799* |
| *Thermus* | Myers and Gelfand, Biochem., 30:7661 (1991). |
| *thermophilus* | PCT Pub. No. WO 91/09950* |
| | PCT Pub. No. WO 91/09944* |
| | Bechtereva et al., Nucleic Acids Res., 17:10507 (1989). |
| | Glukhov et al., Mol. Cell. Probes 4:435–443 (1990). |
| | Carballeira et al., BioTech., 9:276–281 (1990). |
| | Rüttiman et al., Eur. J. Biochem., 149:41–46 (1985). |
| | Oshima et al., J. Biochem., 75:179–183 (1974). |
| | Sakaguchi and Yajima, Fed. Proc., 33:1492 (1974) (abstract). |
| *Thermus flavus* | Kaledin et al., Biochem., 46:1247–1254 (1981); Biokhimiya 46:1576–1584 (1981). |
| | PCT Pub No. WO 94/26766* |
| *Thermus ruber* | Kaledin et al., Biochem., 47:1515–1521 (1982); Biokhimiya 47:1785–1791 (1982). |
| *Thermoplasma* | Hamal et al., Eur. J. Biochem., 190:517–521 (1990). |
| *acidophilum* | Forterre et al., Can. J. Microbiol., 35:228–233 (1989). |
| *Sulfolobus* | Salhi el al., J. Mol. Biol., 209:635–641 (1989). |
| *acidocaldarius* | Salhi et al., Biochem. Biophys. Res. Comm., 167:1341–1347 (1990). |
| | Rella et al., Ital. J. Biochem., 39:83–99 (1990). |
| | Forterre et al., Can. J. Microbiol., 35:228–233 (1989). |
| | Rossi et al., System. Appl. Microbiol., 7:337–341 (1986). |
| | Klimczak et al., Nucleic Acids Res., 13:5269–5282 (1985). |
| | Elie et al., Biochim. Biophys. Acta 951:261–267 (1988). |
| *Bacillus caldotenax* | J. Biochem., 113:401–410 (1993). |
| *Bacillus* | Sellmann et al., J. Bacteriol., |
| *stearothermophilus* | 174:4350–4355 (1992). |
| | Stenesh and McGowan, Biochim. Biophys. Acta 475:32–44 (1977). |
| | Stenesh and Roe, Biochim. Biophys. Acta 272:156–166 (1972). |
| | Kaboev et al., J. Bacteriol., 145:21–26 (1981). |
| *Methanobacterium* | Klimczak et al., Biochem., |
| *thermoautotropicum* | 25:4850–4855 (1986). |
| *Thermococcus* | Kong et al., J. Biol. Chem. 268:1965 (1993) |
| *litoralis* | U.S. Pat. No. 5,210,036* |
| | U.S. Pat. No. 5,322,785* |
| *Anaerocellum thermophilus* | Ankenbauer et al., WO 98/14588* |
| Pyrococcus sp. $KOD_1$ | U.S. Pat. No. 6,008,025* |
| *Pyrococcus furiosus* | Lundberg et al., Gene 108:1 (1991) |
| | PCT Pub. WO 92/09689 |
| | U.S. Pat. No. 5,948,663 |
| | U.S. Pat. No. 5,866,395 |

*Herein incorporated by reference.

In addition to native forms, modified forms of thermostable DNA polymerases having reduced or absent 5' to 3' exonuclease activity have been expressed and purified from *T. aquaticus, T. maritima*. Thermus species sps17, Thermus species Z05*, T. thermophilus, Bacillus stearothermophilus* (U.S. Pat. Nos. 5,747,298, 5,834,253, 5,874,282, and 5,830,714) and *T. africanus* (WO 92/06200).

III. Uses For Thermophilic DNA Polymerases

One application for thermostable DNA polymerases is the polymerase chain reaction (PCR). The PCR process is described in U.S. Pat. Nos. 4,683,195 and 4,683,202, the disclosures of which are incorporated herein by reference. Primers, template, nucleoside triphosphates, appropriate buffer and reaction conditions, and polymerase are used in the PCR process, which involves multiple cycles of denaturation of target DNA, hybridization of primers to the target DNA and synthesis of complementary strands. The extension product of each primer becomes a template in the subsequent cycle for production of the desired nucleic acid sequence. Use of a thermostable DNA polymerase enzyme in PCR allows repetitive heating/cooling cycles without the requirement of fresh DNA polymerase enzyme at each cooling step because heat will not destroy the polymerase activity. This represents a major advantage over the use of mesophilic DNA polymerase enzymes such as Klenow in PCR, as fresh mesophilic polymerase must be added to each individual reaction tube at every cycle. The use of Taq in PCR is described in U.S. Pat. No. 4,965,188, EP Publ. No. 258,017, and PCT Publ. No. 89/06691, herein incorporated by reference.

In addition to PCR, thermostable DNA polymerases are widely used in other molecular biology techniques including recombinant DNA methods. For example, various forms of Taq have been used in a combination method which utilizes reverse transcription and PCR (e.g., U.S. Pat. No. 5,322,770, herein incorporated by reference). DNA sequencing methods utilizing Taq DNA polymerase have also been described (e.g., U.S. Pat. No. 5,075,216, herein incorporated by reference).

However, some thermostable DNA polymerases have certain characteristics (e.g., 5' to 3' exonuclease activity) which are undesirable in PCR and other applications. In some cases, when thermostable DNA polymerases that have 5' to 3' exonuclease activity (e.g., Taq, Tma, Tsps17, TZ05, Tth and Taf) are used in the PCR process and other methods, a variety of undesirable results have been observed, including a limitation of the amount of PCR product produced, an impaired ability to generate long PCR products or to amplify regions containing significant secondary structure, the production of shadow bands or the attenuation in signal strength of desired termination bands during DNA sequencing, the degradation of the 5' end of oligonucleotide primers in the context of double-stranded primer-template complex, nick-translation synthesis during oligonucleotide-directed mutagenesis and the degradation of the RNA component of RNA:DNA hybrids. When utilized in a PCR process with double-stranded primer-template complex, the 5' to 3' exonuclease activity of a DNA polymerase may result in degradation of oligonucleotide primers from their 5' end. This activity is undesirable not only in PCR, but also in second-strand cDNA synthesis and sequencing processes.

When choosing to produce and use an enzyme for sequencing, various factors are considered. For example, large quantities of the enzyme should be easy to prepare; the enzyme should be stable upon storage for considerable time periods; the enzyme should accept all deoxy and dideoxy nucleotides and analogues as substrates with equal affinities and high fidelity; the polymerase activity should be highly processive over nucleotide extensions to 1 kb and beyond, even through regions of secondary structure within the template; the activity should remain high, even in suboptimal conditions; and the enzyme should be inexpensive (A. T. Bankier, "Dideoxy sequencing reactions using Klenow fragment DNA polymerase I," in H. and A. Griffin (eds.), *Methods in Molecular Biology: DNA Sequencing Protocols*, Humana Press, Totowa, N.J., 1993, pp. 83–90). Furthermore, the enzyme should be able to function at elevated temperatures (e.g., greater than about 70° C.), so that non-specific priming reactions are minimized. However, there are no native enzymes which fully meet all of these criteria. Thus, mutant forms of enzymes have been produced in order to address some of these needs.

For example, mutant forms of thermostable DNA polymerases that exhibit reduced or absent 5' to 3' exonuclease activity have been generated. The Stoffel fragment of Taq DNA polymerase lacks 5' to 3' exonuclease activity due to genetic manipulations that resulted in the production of a truncated protein lacking the N-terminal 289 amino acids (e.g., Lawyer et al., J. Biol. Chem., 264:6427–6437, 1989; and Lawyer et al., PCR Meth. Appl., 2:275–287, 1993). Analogous mutant polymerases have been generated from various polymerases, including Tma, Tsps17, TZ05, Tth and Taf. While the generation of thermostable polymerases lacking 5' to 3' exonuclease activity provides improved enzymes for certain applications, some of these mutant polymerases still have undesirable characteristics, including the presence of 3' to 5' exonuclease activity.

The 3' to 5' exonuclease activity is commonly referred to as proof-reading activity, it removes bases that are mismatched at the 3' end of a primer in a primer-template duplex. While the presence of 3' to 5' exonuclease activity may be advantageous, as it leads to an increase in the fidelity of replication of nucleic acid strands, it also has some undesirable characteristics. The 3' to 5' exonuclease activity found in thermostable DNA polymerases such as Tma (including mutant forms of Tma that lack 5' to 3' exonuclease activity) also degrades single-stranded DNA such as primers used in PCR, single-stranded templates and single-stranded PCR products. The integrity of the 3' end of an oligonucleotide primer used in a primer extension process (e.g., PCR, Sanger sequencing methods, etc.) is critical, as it is from this terminus that extension of the nascent strand begins. Degradation of the 3' end of a primer results in loss of specificity in the priming reaction (i.e., the shorter the primer, the more likely that non-specific priming will occur).

Degradation of an oligonucleotide primer by a 3' to 5' exonuclease can be prevented by use of nucleotides modified at their 3' terminus. For example, use of dideoxynucleotides or deoxynucleotides having a phosphorothiolate linkage between nucleotides at the 3' terminus of an oligonucleotide can prevent degradation by 3' to 5' exonucleases. However, the need to use modified nucleotides to prevent degradation of oligonucleotides by a 3' to 5' exonuclease increases the time and cost required to prepare oligonucleotide primers.

A few examples of thermostable polymerases lacking both 5' to 3' exonuclease and 3' to 5' exonuclease are known. As discussed above, the Stoffel fragment of Taq DNA polymerase lacks the 5' to 3' exonuclease activity due to genetic manipulation and no 3' to 5' activity. is present, as Taq polymerase is naturally lacking in 3' to 5' exonuclease activity. Likewise, Tth polymerase naturally lacks 3' to 5' exonuclease activity and deletion nucleotide sequence encoding N-terminal amino acids can be used to remove 5' to 3' exonuclease activity.

Despite development of recombinant enzymes such as Stoffel fragment, there remains a need for other thermostable polymerases having improved characteristics for various applications. For example, some thermostable polymerases possess reverse transcriptase activity and they find use in reverse transcription methods since elevated temperatures help the enzyme to proceed through regions of the RNA which at lower temperatures would possess secondary structure. However, reverse transcription by thermostable DNA polymerases is often dependent on manganese. Unfortunately, the presence of manganese ions can cause higher rates of infidelity and damage to polynucleotides. Accordingly, what is needed in the art are improved thermostable DNA polymerases with enhanced properties, such as reverse transcriptase activity in the presence of magnesium.

SUMMARY OF THE INVENTION

The present invention relates to purified thermostable *Thermoactinomyces vulgaris* (*Tvu*) DNA polymerase. The present invention is not limited to any particular nucleic acid or amino acid sequence. Indeed, a variety of nucleic acid sequences encoding full-length, mutant, and truncated Tvu DNA polymerases are contemplated. The present invention also provides methods for the isolation of purified preparations of Tvu DNA polymerases. The origin of the Tvu DNA polymerases of the present invention is not limited to any particular source. Tvu DNA polymerases may be isolated from Tvu cells (i.e., native) or from host cells expressing nucleic acid sequences encoding Tvu DNA polymerase (i.e., recombinant).

In one embodiment, the present invention contemplates an isolated and purified, native thermostable Tvu DNA polymerase that has DNA synthesis activity. In another embodiment, the purified, native Tvu DNA polymerase has 5' to 3' exonuclease activity.

A contemplated isolated and purified, native Tvu DNA polymerase enzyme is at least 85 percent pure, in a more preferred embodiment the enzyme is at least 90 percent pure, and in a most preferred embodiment the enzyme is at least 95 percent pure, as determined by gel electrophoresis followed by staining or autoradiography then and laser scanning densitometry.

In another embodiment, the purified, native Tvu DNA polymerase exhibits reverse transcriptase activity in the presence of either magnesium ions or manganese ions. In a preferred embodiment, the purified, native Tvu DNA polymerase exhibits elevated reverse transcriptase activity in the presence of magnesium ions in comparison to reverse transcriptase activity in the presence of manganese ions. In still another embodiment, reverse transcriptase activity in the presence magnesium ions is manganese ion-independent.

In one embodiment, the present invention contemplates a purified, recombinant thermostable Tvu DNA polymerase that has DNA synthesis activity. In another embodiment, the purified, recombinant Tvu DNA polymerase has 5' to 3' exonuclease activity. A contemplated recombinant Tvu DNA polymerase has similar 5' to 3' exonuclease activity as compared to native Tvu DNA polymerase. In another embodiment, the recombinant Tvu DNA polymerase is mutant and has reduced 5' to 3' exonuclease activity as compared to the 5' to 3' exonuclease activity of wild-type Tvu DNA polymerase. In another embodiment, the mutant Tvu polymerase is substantially free of 5' to 3' exonuclease activity.

In a preferred embodiment, the purified, recombinant Tvu DNA polymerase enzyme is at least 80 percent pure, in a more preferred embodiment, the enzyme is at least 90 percent pure, and in a most preferred embodiment, the enzyme is at least 95 percent pure, as determined by gel electrophoresis followed by staining or autoradiography and then laser scanning densitometry.

In another embodiment, the purified, recombinant Tvu DNA polymerase exhibits reverse transcriptase activity in the presence of either magnesium ions or manganese ions. In still other embodiments, reverse transcriptase activity in the presence magnesium ions is substantially manganese ion-independent.

The present invention further provides nucleic acids encoding thermostable Tvu DNA polymerases. The present invention is not limited to any particular form of nucleic acid. In some embodiments, the nucleic acid is DNA. In other embodiments, the nucleic acid is RNA. Preferred contemplated Tvu DNA polymerase enzymes are encoded by the oligonucleotide having the sequence of SEQ ID NO: 1, or the truncated DNA coding sequence of SEQ ID NO: 3 or the truncated DNA coding sequence of SEQ ID NO: 5 or variants thereof.

However, the present invention is not limited to any one sequence. Indeed, a variety of variant nucleic acid sequences are contemplated. In some embodiments, the nucleic acid encoding thermostable Tvu DNA polymerases is mutated to encode a polymerase that is substantially free of 5' to 3' exonuclease activity. A DNA variant encoding Tvu DNA polymerase with DNA synthesis activity can have either conservative or non-conservative amino acid substitutions.

In some embodiments, the nucleic acid sequence is selected from sequences that hybridize to SEQ ID NO: 1 under high stringency conditions and sequences that hybridize to the complementary sequence of SEQ ID NO: 1 under high stringency conditions.

In other embodiments, the present invention provides purified oligonucleotides of at least 15 consecutive nucleotides of the nucleic acid of SEQ ID NO: 1 or complementary to at least 15 consecutive nucleotides of the nucleic acid sequence of SEQ ID NO: 1.

In some embodiments, these oligonucleotides of at least 15 consecutive nucleotides of SEQ ID NO: 1 or its complement are used to amplify the nucleic acid of SEQ ID NO: 1 and variants or homologs thereof. In still other embodiments, the oligonucleotides are used to identify homologs or variants of the nucleic acid sequence of SEQ ID NO: 1 by hybridization procedures.

The present invention also provides recombinant DNA vectors or expression vectors comprising nucleic acid sequences that encode a thermostable Tvu DNA polymerase having DNA synthesis activity. In some embodiments, the polymerase-encoding nucleic acid sequence is set forth in SEQ ID NO: 1 or a DNA variant thereof. The DNA variant is as discussed above. In other embodiments, the recombinant DNA vector contains a mutant nucleic acid sequence set forth in SEQ ID NO: 3 and 5, or a DNA variant thereof, encoding a thermostable Tvu DNA polymerase that is substantially free of 5' to 3' exonuclease activity. A variant nucleic acid sequence is a sequence that encodes an amino acid residue sequence that is at least 95 percent or more identical to the sequence of a Tvu DNA polymerase of SEQ ID NOs. 2, 4, or 6.

In further embodiments, the vector comprises a recombinant nucleic acid selected from nucleic acids that hybridize to SEQ ID NO: 1, 3, or 5 or DNA variants thereof under conditions of medium or high stringency. In still further embodiments, the vector comprises a prokaryotic origin of replication. In other embodiments, the vector further comprises a promoter or enhancer sequence operably linked to the recombinant nucleic acid encoding Tvu DNA polymerase. Optionally, the promoter is inducible by an exogenously supplied agent, most preferably the promoter is induced by exogenously supplied IPTG. In some embodiments, the vector further comprises a selectable marker.

The present invention further contemplates host cells transformed with a vector comprising a nucleic acid sequence (or a variant thereof) encoding a Tvu DNA polymerase capable of DNA synthesis activity. The invention is not limited by the choice of host cell; host cells may comprise prokaryotic or eukaryotic cells. In some embodiments, the host cell is a bacterial cell (e.g., an E. Coli cell). In other embodiments the host cell is a mammalian cell, yeast cell, or insect cell.

The invention further provides methods for determining the DNA sequence of a segment or portion of a DNA molecule using the Tvu DNA polymerases of the invention. Traditional (i.e., Sanger) as well as other methods, including but not limited to, chain termination sequencing or thermal cycle sequencing protocols benefit from the use of the Tvu DNA polymerases of the invention. Thus, for example, in some embodiments, dideoxynucleotide (ddNTP) chain termination sequencing protocols are used in conjunction with the polymerases of the invention.

Accordingly, in some embodiments, the present invention provides methods for determining the nucleotide base sequence of a DNA molecule comprising the steps of a) providing in any order: i) a reaction vessel (e.g., any suitable container such as a microcentrifuge tube or a microtiter plate); ii) at least one deoxynucleoside triphosphate; iii) a thermostable Tvu DNA polymerase; iv) at least one DNA synthesis terminating agent that terminates DNA synthesis at a specific nucleotide base; v) a first DNA molecule; and vi) at least one primer capable of hybridizing to the first DNA molecule; b) adding to the reaction vessel, in any order, the deoxynucleoside triphosphate, DNA polymerase, DNA synthesis terminating agent, first DNA molecule, and the primer so as to form a reaction mixture, under conditions such that the primer hybridizes to the DNA molecule, and the DNA polymerase is capable of conducting primer extension to produce a population of DNA molecules complementary to the first DNA molecule; and c) determining at least a part of the nucleotide base sequence of the first DNA molecule. As the present invention encompasses any order of addition that permits the primer to hybridize to the DNA molecule and the DNA polymerase to be capable of conducting primer extension, the methods of the present invention are not limited by the order in which the reaction components are added to the reaction vessel. In a preferred embodiment, the DNA polymerase is added last. The conditions that permit the primer to hybridize to the DNA molecule, and allow the DNA polymerase to conduct primer extension may comprise the use of a buffer.

In one embodiment, the sequencing method uses a native Tvu DNA polymerase. In an alternative embodiment the sequencing method uses a recombinant DNA polymerase.

In an alternative embodiment, the conditions of the method comprise heating the mixture. In another embodiment, the method further comprises cooling the mixture to a temperature at which the thermostable DNA polymerase conducts primer extension. In a particularly preferred embodiment, the method further comprises one or more cycles of heating and then cooling. In yet another embodiment of the method, the reaction mixture comprises 7-deaza dGTP, dATP, dTTP and dCTP.

It is contemplated that various DNA synthesis terminating agents are useful in the present invention. In a preferred embodiment, the DNA synthesis terminating agent is a dideoxynucleoside triphosphate. In a particularly preferred embodiment, the dideoxynucleoside triphosphate is selected from the group consisting of ddGTP, ddATP, ddTTP and ddCTP.

It is also contemplated that the primer used in the sequencing method of the present invention is labelled. In a preferred embodiment, the primer is labelled with $^{32}P$, $^{33}P$, $^{35}S$, enzyme, or fluorescent molecule. It is also contemplated that reactants other than the primer used in the method of the present invention are labelled. For example, in one embodiment, one deoxynucleoside triphosphate is labelled. In a preferred form of this embodiment, the deoxynucleoside triphosphate is labelled with $^{32}P$, $^{33}P$, $^{35}S$, enzyme, or a fluorescent molecule.

It is further contemplated that additional steps or substeps will be incorporated into the sequencing method of the present invention. For example, in one embodiment, step b) further comprises adding a thermostable pyrophosphatase to the reaction mixture. In a preferred form of this embodiment, the thermostable pyrophosphatase is *Thermus thermophilus* pyrophosphatase. In some embodiments, the method uses a mixture or blend comprising a Tvu DNA polymerase and a thermostable pyrophosphatase.

The present invention also provides kits, for example, for determining the nucleotide base sequence of a DNA molecule comprising: a) a thermostable Tvu DNA polymerase; and b) at least one nucleotide mixture comprising deoxynucleoside triphosphates and one dideoxynucleoside triphosphate. In a preferred embodiment, the polymerase of the kit is a non-naturally occurring DNA polymerase. It is also contemplated that the mutant Tvu DNA polymerase is substantially free of significant 5' exonuclease activity. In another embodiment, the mutant Tvu DNA polymerase of the kit is substantially free of 3' exonuclease activity.

In an alternative embodiment, the kit of the present invention contains a first nucleotide mixture, a second nucleotide mixture, a third nucleotide mixture, and a fourth nucleotide mixture, with the first nucleotide mixture comprising ddGTP, 7-deaza dGTP, dATP, dTTP and dCTP, the second nucleotide mixture comprising ddATP, 7-deaza dGTP, dATP, dTTP and dCTP, the third nucleotide mixture comprising ddTTP, 7-deaza dGTP, dATP, dTTP and dCTP and the fourth nucleotide mixture ddCTP, 7-deaza dGTP, dATP, dTTP and dCTP. It is also contemplated that the kit of this embodiment further comprises a thermostable pyrophosphatase. In a particularly preferred embodiment, the thermostable pyrophosphatase is Tth pyrophosphatase. In preferred embodiments, the kit contains a mixture or blend comprising a Tvu DNA polymerase and a thermostable pyrophosphatase.

The present invention also provides methods for amplifying a double stranded DNA molecule, comprising the steps of: a) providing: i) a first DNA molecule comprising a first strand and a second strand, wherein the first and second strands are complementary to one another; ii) a first primer and a second primer, wherein the first primer is complementary to the first DNA strand, and the second primer is complementary to the second DNA strand; and iii) a first thermostable DNA polymerase derived from the eubacterium *Thermoactinomyces vulgaris*; and b) mixing the first DNA molecule, first primer, second primer, and polymerase to form a reaction mixture under conditions such that a second DNA molecule comprising a third strand and a fourth strand are synthesized, with the third strand having a region complementary to the first strand and the fourth strand having a region complementary to the second strand. The method of the present invention is not limited by the source of the first DNA molecule. In a preferred embodiment, the first DNA molecule is present in a genomic DNA mixture (e.g., in genomic DNA extracted from an organism, tissue or cell line). In alternative embodiments, the first DNA molecule is derived from an RNA molecule by means of reverse transcription (RT). The newly synthesized DNA molecule (cDNA) then serves as substrate in a subsequent amplification reaction (PCR). The conditions that permit the primer to hybridize to the DNA molecule, and allow the DNA polymerase, either alone or in combination with another thermostable DNA polymerase, to conduct primer extension may comprise the use of a buffer.

In one embodiment, the method conditions comprise heating the mixture. In an alternative embodiment, the method further comprises cooling the mixture to a temperature at which the thermostable Tvu DNA polymerase, either alone or in combination with another thermostable DNA polymerase, can conduct primer extension. In a particularly preferred embodiment, the method comprises repeating the heating and cooling the mixture one or more times.

It is also contemplated that the Tvu DNA polymerase of the method will have various properties. It is therefore contemplated that in one embodiment of the method, the polymerase is substantially free of 5' to 3' exonuclease activity. In another embodiment, the polymerase is substantially free of both 5' to 3' exonuclease and 3 to 5' exonuclease activity. In other embodiments, the polymerase has reverse transcriptase activity in the presence of either magnesium or manganese ions. In still other embodiments, the reverse transcriptase activity in presence of magnesium ions is substantially manganese ion-independent.

The present invention has many benefits and advantages, several of which are listed below.

One benefit of the invention is that the thermostable Tvu DNA polymerase enzyme can be used for processes of high temperature nucleic acid amplification and sequencing without substantial loss of DNA synthesis activity.

An advantage of the invention is that the enzyme can be used to perform high temperature reverse transcription in the absence of manganese ions.

A further advantage of the invention is that the enzyme can be used in high throughput robotically-manipulated procedures because greater enzymatic stability is retained at room temperature.

Still further benefits and advantages will be apparent to the worker of ordinary skill from the disclosure that follows.

BRIEF DESCRIPTION OF THE DRAWINGS

FIG. 2 illustrates the single letter code alignment of amino acid residue sequences from three regions within the 3' to 5' exonuclease domain of selected DNA polymerases as well as a consensus sequence of identical residues present in all three enzymes, wherein dashes in a sequence represent residues absent.

FIG. 3 provides the single letter code nucleotide for the DNA sequence encoding full-length Tvu DNA polymerase (SEQ ID NO: 1).

FIG. 4 provides the predicted amino acid sequence of full-length Tvu DNA polymerase (SEQ ID NO: 2).

FIG. 5 provides the DNA sequence encoding the 5' to 3' exonuclease deletion mutant form of Tvu DNA polymerase called M285. This DNA sequence encodes the enzyme beginning at the nucleotides encoding the methionine amino acid at position 285 of wild type Tvu DNA polymerase and ending at the termination codon of the wild type enzyme (SEQ ID NO: 3).

FIG. 6 provides the predicted amino acid sequence of M285 Tvu DNA polymerase (SEQ ID NO: 4).

FIG. 7 provides the DNA sequence encoding the 5' to 3' exonuclease deletion mutant form of Tvu DNA polymerase called T289M. This DNA sequence encodes the enzyme beginning at amino acid 289 of the wild type Tvu DNA polymerase, mutated to encode a methionine instead of threonine that appears at this position in wild type, and ending at the termination codon of the wild type enzyme (SEQ ID NO: 5).

FIG. 8 provides the predicted amino acid sequence of T289M Tvu DNA polymerase (SEQ ID NO: 6).

DEFINITIONS

Figure 1:
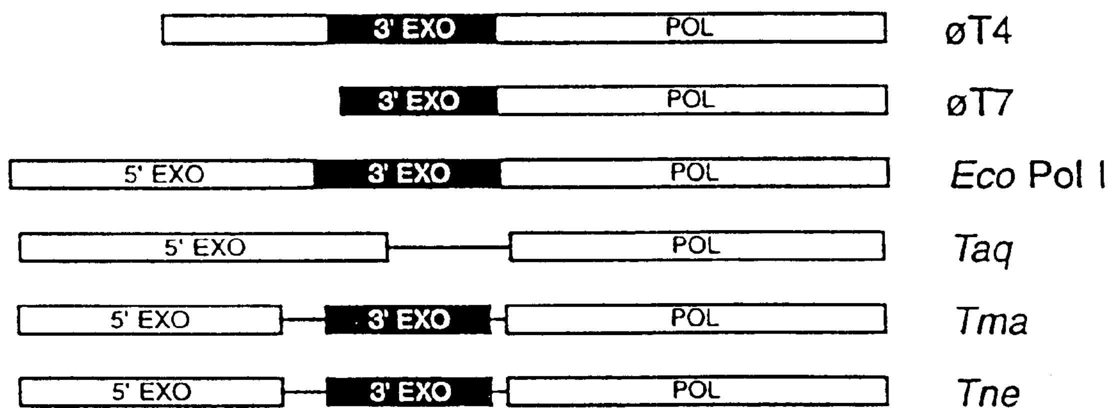
FIG. 1 provides a schematic representation of the 5' to 3' exonuclease, 3' to 5' exonuclease and polymerase domains of several DNA polymerases.

To facilitate understanding of the invention, a number of terms are defined below.

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

"Nucleoside", as used herein, refers to a compound consisting of a purine [guanine (G) or adenine (A)] or pyrimidine [thymine (T), uridine (U), or cytidine (C)] base covalently linked to a pentose, whereas "nucleotide" refers to a nucleoside phosphorylated at one of its pentose hydroxyl groups.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product. The wild-type form of the coding region for the Tvu DNA polymerase is shown in SEQ ID NO: 1; the wild-type form of the Tvu DNA polymerase protein is shown in SEQ ID NO: 2. Tvu DNA polymerase proteins encoded by "mutant" genes are referred to as "variant" Tvu DNA polymerases. Tvu DNA polymerase proteins encoded by "modified" or "mutant" genes are referred to as "non-naturally occurring" or "variant" Tvu DNA polymerases. Tvu DNA polymerase proteins encoded by the wild-type Tvu DNA polymerase gene (i.e., SEQ ID NO:1) are referred to as "naturally occurring" Tvu DNA polymerases.

As used herein, the term "sample template" refers to a nucleic acid originating from a sample which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other than those to be detected may be present as background in a test sample.

As used herein, the term "primer" refers to an oligonucleotide, whether occurring naturally (e.g., as in a purified restriction digest) or produced synthetically, which is capable of acting as a point of initiation of nucleic acid synthesis when placed under conditions in which synthesis of a primer extension product which is complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method.

A primer is said to be "capable of hybridizing to a DNA molecule" if that primer is capable of annealing to the DNA molecule; that is the primer shares a degree of complementarity with the DNA molecule. The degree of complementarity can be, but need not be, complete (i.e., the primer need not be 100% complementary to the DNA molecule). Indeed, when mutagenic PCR is to be conducted, the primer will contain at least one mismatched base which cannot hybridize to the DNA molecule. Any primer which can anneal to and support primer extension along a template DNA molecule under the reaction conditions employed is capable of hybridizing to a DNA molecule.

As used herein, the terms "complementary" or "complementarity" are used in reference to a sequence of nucleotides related by the base-pairing rules. For example, for the sequence 5' "A-G-T" 3', is complementary to the sequence 3' "T-C-A" 5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon hybridization of nucleic acids.

As used herein, the term "probe" refers to an oligonucleotide (i.e., a sequence of nucleotides), whether occurring naturally (e.g., as in a purified restriction digest) or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used herein interchangeably. In addition to probes, primers and deoxynucleoside triphosphates may contain labels; these labels may comprise, but are not limited to, $^{32}$P, $^{33}$P, 3S, enzymes, or fluorescent molecules (e.g., fluorescent dyes).

As used herein, the term "target," when used in reference to the polymerase chain reaction, refers to the region of nucleic acid of interest bounded by the primers. In PCR, this is the region amplified and/or identified. Thus, the "target" is sought to be isolated from other nucleic acid sequences. A "segment" is defined as a region of nucleic acid within the target sequence.

As used herein, the term "polymerase chain reaction" ("PCR") refers to the method described in U.S. Pat. Nos. 4,683,195, 4,889,818, and 4,683,202, all of which are hereby incorporated by reference. These patents describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase (e.g., Taq). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controlable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (i.e., hybridization with a labeled probe; incorporation of biotinylated primers followed by avidin-enzyme conjugate detection; incorporation of $^{32}$P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the terms "PCR product" and "PCR fragment" refer to the resultant mixture of compounds after two or more cycles of the PCR steps of denaturation, annealing and extension are complete. These terms encompass the case where there has been amplification of one or more segments of one or more target sequences.

A DNA polymerase is said herein to be "derived from the eubacterium T vulgaris" if that polymerase comprises all or a portion of the amino acid sequence of the Tvu DNA polymerase of SEQ ID NO: 2 and maintains DNA synthesis activity. DNA polymerases derived from *T. vulgaris* include the native Tvu DNA polymerase isolated from *T. vulgaris* cells, as well as recombinant Tvu DNA polymerases encoded by the wild-type Tvu DNA polymerase gene (SEQ ID NO: 1) or mutant or variants thereof which maintain DNA synthesis activity.

The term "full-length thermostable Tvu DNA polymerase" as used herein, refers to a DNA polymerase that encompasses essentially every amino acid encoded by the Tvu DNA polymerase gene (SEQ ID NO: 1). One skilled in the art knows there are subtle modifications of some proteins in living cells so that the protein is actually a group of closely related proteins with slight alterations. For example, some but not all proteins: a) have amino acids removed from the amino-terminus; and/or b) have added chemical groups (e.g., glycosylation groups). These modifications may result in molecular weight increases or decreases. These types of modifications are typically heterogenous. Thus, not all modifications occur in every molecule. Thus, the natural "full-length" molecule may actually be a family of molecules that start from the same amino acid sequence but have small differences in their modifications. The term "full-length thermostable Tvu DNA polymeras e" encompasses such a family of molecules. The Tvu DNA polymerase gene encodes a protein of 876 amino acids having a predicted molecular weight of 96.3 kilodaltons (kD). As shown in the Examples below, the full-length polymerase migrates with an apparent molecular weight of about 97 kD on a 4–20% gradient Tris-glycine PAGE.

The term "high fidelity polymerase" refers to DNA polymerases with error rates of $5\times10^{-6}$ per base pair or lower. Examples of high fidelity DNA polymerases include the Tli DNA polymerase derived from *Thermococcus litoralis* (Promega, Madison Wis.; New England Biolabs, Beverly Mass.), Pfu DNA polymerase derived from *Pyrococcus furiosus* (Stratagene, San Diego, Calif.), and Pwo DNA polymerase derived from *Pyrococcus woesii* (Boehringer Mannheim). The error rate of a DNA polymerase may be measured using assays known to the art.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein. The term "rTvu" is used to designate a recombinant form of Tvu polymerase. The term "nTvu" is used to designate the native form of Tvu polymerase. The term "Tvu polymerase" encompasses both nTvu and rTvu polymerase.

As used herein in reference to an amino acid sequence or a protein, the term "portion" (as in "a portion of an amino acid sequence") refers to fragments of that protein. The fragments may range in size from four amino acid residues to the entire amino acid sequence minus one amino acid. When used in relation to Tvu polymerases, the fragments may range in size from greater than or equal to about 300 amino acid residues, more preferably greater than or equal to about 400 amino acid residues, most preferably greater to or equal to about 500 amino acids to the entire amino acid sequence minus one amino acid. Particularly preferred fragments of Tvu polymerases retain one or more of the enzymatic activities associated with the wild-type Tvu polymerase (i.e., 5' exonuclease, 3' exonuclease and/or polymerization activity).

As used herein, the term "fusion protein" refers to a chimeric protein containing the protein of interest (e.g., Tvu DNA polymerases and fragments thereof) joined to an exogenous protein fragment (e.g., the fusion partner which consists of a non-Tvu polymerase protein). The fusion partner may enhance the solubility of Tvu polymerase protein as expressed in a host cell, may provide an affinity tag to allow purification of the recombinant fusion protein from the host cell or culture supernatant, or both. If desired, the fusion protein may be removed from the protein of interest (e.g., Tvu DNA polymerase or fragments thereof) by a variety of enzymatic or chemical means know to the art.

The terms "DNA polymerase activity," "synthesis activity" and "polymerase activity" are used interchangeably and refer to the ability of a DNA polymerase to synthesize new DNA strands by the incorporation of deoxynucleoside triphosphates. The examples below provide assays for the measurement of DNA polymerase activity, although a number of such assays are known in the art. A protein capable of directing the synthesis of new DNA strands by the incorporation of deoxynucleoside triphosphates in a template-dependent manner is said to be "capable of DNA synthesis activity."

The term "5' to 3' exonuclease activity" refers to the presence of an activity in a protein that is capable of removing nucleotides from the 5' end of an oligonucleotide. This 5' to 3' exonuclease activity may be measured using any of the assays provided herein or known in the art. The term "substantially free of 5' to 3' exonuclease activity" indicates that the protein has less than about 5% of the 5' to 3' exonuclease activity of wild-type Tvu, preferably less than about 3% of the 5' to 3' exonuclease activity of wild-type Tvu, and most preferably no detectable 5' to 3' exonuclease activity.

The term "3' to 5' exonuclease activity" refers to the presence of an activity in a protein that is capable of removing nucleotides from the 3' end of an oligonucleotide. The 3' to 5' exonuclease activity may be measured using any of the assays provided herein or known in the art. The term "substantially free of 3' to 5' exonuclease activity" indicates that the protein has less than about 5% of the 3' to 5' exonuclease activity of wild-type Tvu, preferably less than about 3% of the 3' to 5' exonuclease activity of wild-type Tvu, and most preferably no detectable 3' to 5' exonuclease activity.

The term "reduced levels of 5' to 3' exonuclease" is used in reference to the level of 5' to 3' exonuclease activity displayed by the wild-type Tvu DNA polymerase (i.e., the polymerase of SEQ ID NO:2) and indicates that the mutant polymerase exhibits lower levels of 5' to 3' exonuclease than does the full-length or unmodified enzyme.

A polymerase which "lacks significant 5' to 3' exonuclease" is a polymerase which exhibits less than about 5% of the 5' to 3' exonuclease activity of wild-type polymerases, preferably less than about 3% of the 5' to 3' exonuclease activity of wild-type polymerases, and most preferably no detectable 5' to 3' exonuclease activity.

The term "reverse transcriptase activity" and "reverse transcription" refers to the ability of an enzyme to synthesize a DNA strand (i.e., complementary DNA, cDNA) utilizing an RNA strand as a template. The term "substantially manganese ion independent," when used in reference to reverse transcriptase activity, refers to reverse transcriptase activity in a reaction mix that contains a low proportion (i.e., less than about 5% of the concentration) of manganese compared to magnesium.

A "DNA synthesis terminating agent which terminates DNA synthesis at a specific nucleotide base" refers to compounds, including but not limited to, dideoxynucleosides having a 2', 3' dideoxy structure (e.g., ddATP, ddCTP, ddGTP and ddTTP). It is contemplated that any compound capable of specifically terminating a DNA sequencing reaction at a specific base may be employed as a DNA synthesis terminating agent.

The terms "cell," "cell line," "host cell," as used herein, are used interchangeably, and all such designations include progeny or potential progeny of these designations. The words "transformants" or "transformed cells" include the primary transformed cells derived from that cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The present invention provides Tvu polymerases expressed in either prokaryotic or eukaryotic host cells. Nucleic acid encoding the Tvu polymerase may be introduced into bacterial host cells by a number of means including transformation of bacterial cells made competent for transformation by treatment with calcium chloride or by electroporation. In embodiments in which Tvu polymerases are to be expressed in the host cells, nucleic acid encoding the Tvu polymerase may be introduced into eukaryotic host cells by any suitable means, including calcium phosphate co-precipitation, spheroplast fusion, electroporation and the like. When the eukaryotic host cell is a yeast cell, transformation may be accomplished by such methods as treatment of the host cells with lithium acetate or by electroporation.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Nucleic acids are known to contain different types of mutations. A "point" mutation refers to an alteration in the sequence of a nucleotide at a single base position from the wild type sequence. Mutations may also refer to insertion or deletion of one or more bases, so that the nucleic acid sequence differs from the wild-type sequence.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity). In this case, in the absence of non-specific binding, the probe will not hybridize to the second non-complementary target.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the Tm (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989, *Nucleic Acid Hybridization, A Practical Approach*, IRL Press, Washington D.C., 1985, for a general discussion of the state of the art).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in absolution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

As used herein, the term "$T_m$" is used in reference to the "melting temperature". The melting temperature is the temperature at which 50% of a population of double-stranded nucleic acid molecules becomes dissociated into single strands. The equation for calculating the Tm of nucleic acids is well-known in the art. The $T_m$ of a hybrid nucleic acid is often estimated using a formula adopted from hybridization assays in 1 M salt, and commonly used for calculating $T_m$ for PCR primers: [(number of A+T)×2° C.+(number of G+C)×4° C.]. (C. R. Newton et al., *PCR*, 2nd Ed., Springer-Verlag (New York, 1997), p. 24). This formula was found to be inaccurate for primers longer than 20 nucleotides. (Id.) Another simple estimate of the $T_m$ value may be calculated by the equation: $T_m$=81.5+0.41(% G+C), when a nucleic acid is in aqueous solution at 1 M NaCl. (e.g., Anderson and Young, Quantitative Filter Hybridization, in *Nucleic Acid Hybridization* (1985). Other more sophisticated computations exist in the art which take structural as well as sequence characteristics into account for the calculation of $T_m$. A calculated $T_m$ is merely an estimate; the optimum temperature is commonly determined empirically.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs which encode a multitude of proteins. However, isolated nucleic acid encoding a Tvu polymerase includes, by way of example, such nucleic acid in cells ordinarily expressing a Tvu polymerase where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and anti-sense strands (i.e., the oligonucleotide may be double-stranded).

As used herein, the term "purified" or "to purify". means the result of any process that removes some of a contaminant from the component of interest, such as a protein or nucleic acid. The percent of a purified component is thereby increased in the sample. Percent purity can be determined by gel electrophoresis followed by authoradiography and quantitation of protein bands by laser densitometry. The bands quantified are the 97 kD band for the full-length Tvu polymerase and 66 kD band for mutant Tvu polyrnerases when compared to Mark 12 size markers (Novex) on a 4–20% Tris-Glycine gel (Novex EC6025). In this example, percent purity is determined by determining the density of the appropriate band (e.g., the 97 kD band or 66 kD band) and dividing by the total density of the lane in which the band appears.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional protein is produced.

As used herein, the term "promoter" means a recognition site on a DNA sequence or group of DNA sequences that provide an expression control element for a gene and to which RNA polymerase specifically binds and initiates RNA synthesis (transcription) of that gene.

As used herein, the term "recombinant DNA molecule" means a hybrid DNA sequence comprising at least two nucleotide sequences not normally found together in nature.

As used herein, the term "vector" is used in reference to nucleic acid molecules that transfer DNA segment(s) from one cell to another and capable of replication in a cell. Vectors may include plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in host cells and possibly other sequences, e.g. an optional operator sequence. A promoter is defined as a DNA sequence that directs RNA polymerase to bind to DNA and to initiate RNA synthesis. Eukaryotic expression vectors include a promoter, polyadenlyation signal and optionally an enhancer sequence.

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the term "a polynucleotide having a nucleotide sequence encoding a gene," means a nucleic acid sequence comprising the coding region of a gene, or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987). For example, the SV40 early gene enhancer is very active in a wide variety of cell types from many mammalian species and has been widely used for the expression of proteins in mammalian cells (Dijkema et al., EMBO J. 4:761, 1985). Two other examples of promoter/enhancer elements active in a broad range of mammalian cell types are those from the human elongation factor 1α gene (Uetsuki et al., J. Biol. Chem., 264:5791, 1989; Kim, et al., Gene 91:217, 1990; and Mizushima and Nagata, Nuc. Acids. Res., 18:5322, 1990) and the long terminal repeats of the Rous sarcoma virus (Gorman et al., Proc. Natl. Acad. Sci. USA 79:6777, 1982); and the human cytomegalovirus (Boshart, et al., Cell 41:521, 1985).

As used herein, the term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/Bcl restriction fragment and directs both termination and polyadenylation (Sambrook, supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors. containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (~100 copies/cell).

All amino acid residues identified herein are in the natural L-configuration. In keeping with standard polypeptide nomenclature, J. Biol. Chem., 243:3557–3559 (1969), abbreviations for amino acid residues are as shown in the following Table of Correspondence.

TABLE OF CORRESPONDENCE

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

DESCRIPTION OF THE INVENTION

The present invention provides purified thermostable DNA polymerase I enzymes derived from *T. vulgaris* (*Tvu*). The present invention encompasses both native and recombinant wild-type forms of the enzyme, as well as mutant and variant forms, some of which possess altered characteristics relative to the wild-type enzyme. In some embodiments, the present invention provides mutants that lack 5' to 3' exonuclease activity. The present invention also relates to methods of using the Tvu polymerase, including its use in amplification, reverse transcription, and sequencing reactions. Indeed, the novel properties of the polymerases of the present invention provide improved enzymes for a variety of applications utilizing thermostable DNA polymerases. The description of the invention is divided into: I. General Structural Features of Type A DNA Polymerases; II. Generation of Tvu DNA Polymerases; III. Use of Tvu DNA Polymerases in the PCR; IV. Use of Tvu DNA Polymerase for Reverse Transcription; and V. Use of Tvu DNA Polymerases in DNA Sequencing Methods.

I. General Structural Features Of DNA Polymerases

DNA polymerases (DNAPs), such as those isolated from mesophilic organisms (e.g., *E. coli*) as well as from thermophilic bacteria (e.g., Thermus, Thermotoga, and Thermoactinomyces), are enzymes that synthesize new DNA strands. As previously indicated, several of the known DNAPs contain associated nuclease activities in addition to the polymerization activity of the enzyme.

Some DNAPs have exonuclease activities that are known to remove nucleotides from the 5' and 3' ends of DNA chains (Kornberg, *DNA Replication*, W.H. Freeman and Co., San Francisco, pp. 127–139, 1980). These exonuclease activities are usually referred to as 5' to 3' exonuclease and 3' to 5' exonuclease activities, respectively. For example, the 5' to 3' exonuclease activity located in the N-terminal domain of several DNAPs participates in the removal of RNA primers during lagging strand synthesis during DNA replication and the removal of damaged nucleotides during DNA repair. Some DNAPs, such as the *E. coli* DNA polymerase I, also have a 3' to 5' exonuclease activity responsible for proofreading during DNA synthesis (Kornberg, supra).

DNAPs isolated from *Thermus aquaticus* (*Taq*), *Thermus flavus* (*Tfl*) and *Thermus thermophilus* (*Tth*) have a 5' to 3' exonuclease activity, but lack a functional 3' to 5' exonuclease (Tindall and Kunkell, Biochem. 27:6008, 1988). However, the lack of a 3' to 5' exonuclease activity is not a general feature of DNAPs derived from thermophilic bacteria as DNA polymerases from the thermophiles *Thermotoga maritima* (*Tma*), *Thermococcus litoralis* (*Tli*) and *Pyrococcus furiosus* (*Pfu*) do contain 3' to 5' exonuclease activity. *Bacillus caldotenax* has a very weak 3' to 5' exonuclease activity although it lacks the three aspartic acid residues of the 3' to 5' exonuclease consensus sequence as further discussed below.

The 5' to 3' exonuclease activity associated with a number of eubacterial Type-A DNA polymerases has been found to reside in the one-third N-terminal region of the protein as an independent functional domain. In these polymerase molecules, the C-terminal two-thirds of the molecule constitute the polymerization domain responsible for synthesis of DNA activity. Some Type-A DNA polymerases also have a 3' to 5' exonuclease activity associated with the C-terminal two-thirds of the molecule. As described more completely below, FIG. 1 provides a schematic showing the location of the 5' to 3' exonuclease, 3' to 5' exonuclease and polymerase encoded activities of a number of eubacterial DNAPs. As noted above, not all DNAPs contain both 5' to 3' and 3' to 5' exonuclease activities.

FIG. 1 provides a schematic depicting the arrangement of the 5' to 3' exonuclease ("5' EXO"), 3' to 5'exonuclease ("3' EXO") and polymerase ("POL") encoded activities in the DNA polymerases from phage T4 ("ϕT4"), phage T7 ("ϕT7"), *E. coli* (DNA polymerase I; "Eco Pol I"), *T. aquaticus* ("*Taq*"), *T. maritima* ("*Tma*") and *T. neapolitana* ("*Tne*"). The absence of a 3' to 5' exonuclease activity in Taq DNA polymerase is indicated by the use of the line between the boxed 5' to 3' exonuclease and polymerase domains; the absence of a 5' to 3' exonuclease activity in phage T4 polymerase is indicated by the absence of the term "5' EXO" in the first boxed region of the molecule.

The 5' to 3' exonuclease activity and the polymerization activity of DNAPs can be separated by proteolytic cleavage or genetic manipulation of the polymerase molecule. For example, the Klenow or large proteolytic cleavage fragment of *E. coli* DNA polymerase I contains polymerase and 3' to 5' exonuclease activity but lacks 5' to.3' exonuclease activity (Brutlag et al., Biochem. Biophys. Res. Commun. 37:982, 1969). The Stoffel fragment of Taq polymerase lacks 5' to 3' exonuclease activity due to a genetic manipulation which deletes the N-terminal 289 amino acids of the polymerase molecule (Erlich et al., Science 252:1643, 1991).

Removal of the 5' to 3' exonuclease domain from a DNAP may effect the activity of the remaining domains. For example, removal of the 5' to 3' exonuclease domain from the *E. coli* polymerase I protein to generate the Klenow fragment, affects the fidelity of the remaining large polymerase domain. The fidelity of a DNA polymerase involves several functions, including the ability to discriminate against errors when nucleotides are initially inserted, the ability to discriminate against extension from misaligned or mispaired primer termini, and exonucleolytic removal of errors.

In comparison to the full-length enzyme, the Klenow fragment exhibits altered base substitution error specificity and is less accurate for minus one base frameshift errors at reiterated template nucleotides (Bebenek et al., J. Biol. Chem. 265:13878, 1990). Thus, the removal of the 5' to 3' exonuclease encoding domain of *E. coli* DNA polymerase I adversely affects fidelity of the remaining 3' to 5' exonuclease and DNA synthesis encoding domains.

Removal of a 5' to 3' exonuclease encoding domain does not always adversely affect fidelity of the resultant polymerase fragment. For example, KlenTaq, a truncated version of Taq DNA polymerase that lacks the first 235 N-terminal amino acids (including the 5' to 3' exonuclease domain), has been reported to have a two-fold improvement in fidelity as compared to full-length Taq (Barnes, Gene 112:29, 1992).

Amino acid sequence comparisons of the 3' to 5' exonuclease encoding domain of a number of DNAPs have identified three domains, termed Exo I–III, that are highly conserved between a variety of mesophilic and thermophilic DNAPs (Bernad et al. Cell 59:219, 1989). FIG. 2 provides a schematic drawing showing an alignment of the amino acid residues from a number of DNAPs over the 3' to 5' exonuclease encoding domain. In FIG. 2, the one letter code is used for the amino acids; the numbers represent the amino acid residue in a given polymerase. Also, in FIG. 2, highly conserved residues which are indicated by the use of white letters within a black box. Portions of the 3' to 5' exonuclease encoding domain of following polymerases are shown: *Bacillus subtilus* (*Bsu*) polymerase III (SEQ ID NOS: 19–21); *E. coli* (*Eco*) polymerase IIIϵ (SEQ ID NOS: 22–24); phage T4 (SEQ ID NOS: 25–27); phage T7 (SEQ ID NOS: 28–30); *E. coli* polymerase I (SEQ ID NOS: 31–33); *T. maritima* (*Tma*) polymerase (SEQ ID NOS: 34–36); and *T. neapolitana* (*Tne*) polymerase (SEQ ID NOS: 37–39). The "∇" indicates amino acid residues involved in single strand DNA binding; the "Δ" indicates amino acid residues involved in metal binding and catalysis.

Site-directed mutagenesis experiments have identified a subset of these conserved residues as being critical for 3' to 5' exonuclease activity in *E. coli* polymerase I. The critical residues include D355, D424, and D501, which are known to bind divalent metal ions and are essential for 3' exonuclease activity, as mutation of these residues reduces 3' exonuclease activity several thousand fold. Amino acids analogous to these three D residues are not present in Tvu DNA polymerase; therefore, it is unlikely that Tvu DNA polymerase has significant 3' to 5' exonuclease activity although it may have a weak 3' to 5' exonuclease activity. Bca DNA polymerase is lacking these three D residues and has been shown to have weak 3' to 5' exonuclease activity (J. Biochem. 113:401–410, 1993). L361, F473 and Y497 are also important for 3' to 5' exonuclease activity and are believed to ensure correct positioning of the substrate in the active site. Mutation of L361 and Y497 reduces 3' to 5' exonuclease activity 12.5 to 25-fold, while mutation of F473 reduces 3' to 5' exonuclease activity about 3000-fold.

PCT Publ. No. WO 92/03556 (herein incoporated by reference) states that three characteristic domains are critical for 3' to 5' exonuclease activity in thermostable Tma DNA polymerases. However, no site-directed mutagenesis is shown for any of the "critical" residues, and no 3' to 5' exonuclease activity is reported for any of the mutant forms of Tma DNA polymerase (i.e., these are primarily deletion mutants) shown. The three domains identified in PCT Publ. No. WO 92/03556 are: Domain A, which comprises D-X-E-$X^3$-L; Domain B, which comprises N-$X^3$-D-$X^3$-L; and Domain C, which comprises Y-$X^3$-D, where $X^N$ represents the number (N) of non-critical amino acids between the specified amino acids. As shown in FIG. 2, the location, sequence and spacing of these three domains found in polymerases derived from thermophilic organisms is consistent with the three domains identified in polymerases derived from mesophilic organisms.

II. Generation Of Tvu DNA Polymerases

The present invention provides wild-type and mutant forms of Tvu DNA polymerases. The mutant forms are substantially free of 5' to 3' exonuclease activity. Without being limited to any particular mutant, representative examples of mutant Tvu DNA polymerases are provided herein. M285 (SEQ ID NO: 4) begins at the methionine codon located at residue 285 of the wild type Tvu DNA polymerase and ends at the wild type termination codon. M285 is encoded by the nucleic acid sequence of SEQ ID NO: 3. T289M (SEQ ID NO: 6) begins at residue 289 of the wild type Tvu DNA polymerase which was mutated from a threonine to a methionine and ends at the wild type termination codon. T289M is encoded by the nucleic acid sequence of SEQ ID NO: 5. The modified Tvu polymerases of the present invention are advantageous in situations where the polymerization (i.e., synthetic) activity of the enzyme is desired but the presence of 5' to 3' exonuclease activity is not.

The present invention is not intended to be limited by the nature of the alteration (e.g., deletion, insertion, substitution) necessary to render the Tvu polymerase deficient in 5' to 3' exonuclease activity. Indeed, the present invention contemplates a variety of methods, including but not limited to proteolysis and genetic manipulation.

A. Tvu Polynucleotides

The present invention provides nucleic acids encoding Tvu DNA polymerase I (SEQ ID NO: 1). Other embodiments of the present invention provide polynucleotide sequences that are capable of hybridizing to SEQ ID NO: 1 under conditions of medium stringency. In some embodiments, the hybridizing polynucleotide sequence encodes a protein that retains at least one biological activity of the naturally occurring Tvu DNA polymerase. In preferred embodiments, hybridization conditions are based on the melting temperature (Tm) of the nucleic acid binding complex and confer a defined "stringency" as explained above (e.g., Wahl, et al., Methods Enzymol. 152:399–407, 1987).

In other embodiments of the present invention, variants of Tvu DNA polymerase are provided (e.g., SEQ ID NOs: 3 and 5). In preferred embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

In still other embodiments of the present invention, the nucleotide sequences of the present invention may be engineered in order to alter a Tvu DNA polymerase coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

B. Tvu Polypeptides

In other embodiments, the present invention provides Tvu DNA polymerase polypeptide (e.g., SEQ ID NO: 2). Other embodiments of the present invention provide fragments, fusion proteins or functional equivalents of Tvu DNA polymerase (e.g., SEQ ID NOs: 4 and 6). In still other embodiments of the present invention, nucleic acid sequences corresponding to Tvu DNA polymerase may be used to generate recombinant DNA molecules that direct the expression of Tvu DNA polymerase and variants in appropriate host cells. In some embodiments of the present invention, the polypeptide may be a naturally purified product, while in other embodiments it may be a product of chemical synthetic procedures, and in still other embodiments it may be produced by recombinant techniques using a prokaryotic or eukaryotic host cell (e.g., by bacterial cells in culture). In other embodiments, the polypeptides of the invention may also include an initial methionine amino acid residue.

In one embodiment of the present invention, due to the inherent degeneracy of the genetic code, DNA sequences other than SEQ ID NO: 1 encoding substantially the same or a functionally equivalent amino acid sequence, may be used to clone and express Tvu DNA polymerase. In general, such polynucleotide sequences hybridize to SEQ ID NO: 1 under conditions of medium stringency as described above. As will be understood by those of skill in the art, it may be advantageous to produce Tvu DNA polymerase-encoding nucleotide sequences possessing non-naturally occurring codons. Therefore, in some preferred embodiments, codons preferred by a particular prokaryotic or eukaryotic host are selected, for example, to increase the rate of Tvu DNA polymerase expression or to produce recombinant RNA transcripts having desirable properties, such as a longer half-life than transcripts produced from naturally occurring sequence.

1. Vectors for Production of Tvu DNA Polymerase

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NO: 1, 3 or 5). In some embodiments of the present invention, the constructs comprise a vector such as a plasmid or viral vector into which a sequence of the invention has been inserted, in a forward or reverse orientation. In still other embodiments, the heterologous structural sequence (e.g., SEQ ID NO: 1, 3, or 5) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors that are replicable and viable in the host are known to those of skill in the art, and are commercially available. Any other plasmid or vector may be used as long as they are replicable and viable in the host. In some preferred embodiments of the present invention, bacterial expression vectors comprise an origin of replication, a suitable promoter and optionally an enhancer, and also any necessary ribosome binding sites, polyadenylation sites, transcriptional termination sequences, and 5' flanking nontranscribed sequences.

In certain embodiments of the present invention, the Tvu DNA sequence in the expression vector is operatively linked to an appropriate expression control sequence(s) (e.g., a constitutive or inducible promoter) to direct mRNA synthesis. Promoters useful in the present invention include, but are not limited to, retroviral LTRs, SV40 promoter, CMV promoter, RSV promoter, *E. coli lac* or trp promoters, phage lambda $P_L$ and $P_R$ promoters, T3, SP6 and T7 promoters. In other embodiments of the present invention, recombinant expression vectors include origins of replication and selectable markers, (e.g., tetracycline or ampicillin resistance in *E. coli*, or neomycin phosphotransferase gene for selection in eukaryotic cells).

In other embodiments, the expression vector also contains a ribosome binding site for translation initiation, as well as a transcription terminator. In still other embodiments of the present invention, the vector may also include appropriate sequences for enhancing expression.

2. Host Cells and Systems for Production of Tvu DNA Polymerase

The present invention contemplates that the nucleic acid construct of the present invention be capable of expression in a suitable host. In particular, it is preferable that the expression system chosen utilizes a controlled promoter such that expression of the Tvu polymerase is prevented until expression is induced. In this manner, potential problems of toxicity of the expressed polymerases to the host cells (and particularly to bacterial host cells) are avoided. Those in the art know methods for attaching various promoters and 3' sequences to a gene sequence in order to achieve efficient and tightly controlled expression. The examples below disclose a number of-suitable vectors and vector constructs. Of course, there are other suitable promoter/vector combinations that are useful in the present invention. The choice of a particular vector is also a function of the type of host cell to be employed (i.e., prokaryotic or eukaryotic).

In some embodiments of the present invention, the host cell can be a prokaryotic cell (e.g., a bacterial cell). Specific examples of host cells include, but are not limited to, *E. coli, Salmonella typhimurium, Bacillus subtilis*, and various species within the genera Pseudomonas, Streptomyces, and Staphylococcus.

The constructs in host cells can be used in a conventional manner to produce the gene product encoded by the recombinant sequence. In some embodiments, introduction of the construct into the host cell can be accomplished by any suitable method known in the art (e.g., calcium phosphate transfection, DEAE-Dextran mediated transfection, or electroporation [e.g., Davis et al., *Basic Methods in Molecular Biology*, 1986]). Alternatively, in some embodiments of the present invention, the polypeptides of the invention can be synthetically produced by conventional peptide synthesizers.

In some embodiments of the present invention, following transformation of a suitable host strain and growth of the host strain to an appropriate cell density, the selected promoter is induced by appropriate means (e.g., temperature shift or chemical induction), and the host cells are cultured for an additional period. In other embodiments of the present invention, the host cells are harvested (e.g., by centrifugation), disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

It is not necessary that a host organism be used for the expression of the nucleic acid constructs of the invention. For example, expression of the protein encoded by a nucleic acid construct may be achieved through the use of a cell-free in vitro transcriptionltranslation system. An example of such a cell-free system is the commercially available TnT™ Coupled Reticulocyte Lysate System (Promega; this cell-free system is described in U.S. Pat. No. 5,324,637, hereby incorporated by reference).

3. Purification of Tvu DNA Polymerase

The present invention also provides methods for recovering and purifying Tvu DNA polymerase from native and recombinant cell cultures including, but not limited to, ammonium sulfate precipitation, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed as one or more purification steps. In some embodiments, purification is performed as described in Example 1.

In other embodiments of the present invention, the nucleic acid construct containing DNA encoding the wild-type or a variant Tvu polymerase further comprises the addition of exogenous sequences (i.e., sequences not encoded by the Tvu polymerase coding region) to either the 5' or 3' end of the Tvu polymerase coding region to allow for ease in purification of the resulting polymerase protein (the resulting protein containing such an affinity tag is termed a "fusion protein"). Several commercially available expression vectors are available for attaching affinity tags (e.g., an exogenous sequence) to either the amino or carboxy-termini of a coding region. In general these affinity tags are short stretches of amino acids that do not alter the characteristics of the protein to be expressed (i.e., no change to enzymatic activities results).

For example, the pET expression system (Novagen) utilizes a vector containing the T7 promoter operably linked to a fusion protein with a short stretch of histidine residues at either end of the protein and a host cell that can be induced to express the T7 DNA polymerase (i.e., a DE3 host strain).

The production of fusion proteins containing a histidine tract is not limited to the use of a particular expression vector and host strain. Several commercially available expression vectors and host strains can be used to express protein sequences as a fusion protein containing a histidine tract (e.g., the pQE series [pQE-8, 12, 16, 17, 18, 30, 31, 32, 40, 41, 42, 50, 51, 52, 60 and 70] of expression vectors (Qiagen) used with host strains M15[pREP4] [Qiagen] and SG13009 [pREP4] [Qiagen]) can be used to express fusion proteins containing six histidine residues at the amino-terminus of the fusion protein). Additional expression systems which utilize other affinity tags are known to the art.

Once a suitable nucleic acid construct has been made, the Tvu DNA polymerase may be produced from the construct. The examples below and standard molecular biological teachings known in the art enable one to manipulate the construct by a variety of suitable methods. Once the desired Tvu polymerase has been expressed, the polymerase may be tested for DNA synthesis as described below.

4. Deletion Mutants of Tvu DNA Polymerase

The present invention further provides fragments of Tvu DNA polymerase (i.e., deletion mutants; e.g., SEQ ID NOs 4 and 6). In some embodiments of the present invention, when expression of a portion of Tvu DNA polymerase is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol. 169:751–757, 1987) and *S. typhimurium*, and its in vitro activity has been demonstrated on recombinant proteins (Miller et al., PNAS 84:2718–1722, 1990). Therefore, removal of an N-terminal methionine, if desired, can be achieved either in vivo by expressing such recombinant polypeptides in a host producing MAP (e.g., *E. coli* or CM89 or *S. cerevisiae*), or in vitro by use of purified MAP.

In other embodiments of the present invention, Tvu DNA polymerases having a reduced level of 5' to 3' exonuclease compared to wild-type were produced by subcloning portions of Tvu DNA polymerase lacking the 5' to 3' exonuclease-encoding domain (Examples 11–12). In other embodiments, proteolysis is used to remove portion of Tvu polymerase responsible for 5' to 3' exonuclease activity. Following proteolytic digestion, the resulting fragments are separated by standard chomatographic techniques and assayed for the ability to synthesize DNA and to act as a 5' to 3' exonulcease.

5. Variants of Tvu DNA Polymerase

Still other embodiments of the present invention provide other mutant or variant forms of Tvu DNA polymerase. It is possible to modify the structure of a peptide having an activity (e.g., DNA synthesis activity) of Tvu DNA polymerase for such purposes as enhancing stability (e.g., in vitro shelf life, and/or resistance to proteolytic degradation in vivo) or reducing 5' to 3' exonuclease activity. Such modified peptides are considered functional equivalents of peptides having an activity of Tvu DNA polymerase as defined herein. A modified peptide can be produced in which the nucleotide sequence encoding the polypeptide has been altered, such as by substitution, deletion, or addition. In some preferred embodiments of the present invention, the alteration decreases the 5' to 3' exonuclease activity to a level low enough to provide an improved enzyme for a variety of applications such as PCR and chain termination sequencing (including thermal cycle sequencing) as discussed in the Examples below. In particularly preferred embodiments, these modifications do not significantly reduce the DNA synthesis activity of the modified enzyme. In other words, construct "X" can be evaluated according to the protocol described below in order to determine whether it is a member of the genus of modified Tvu polymerases of the present invention as defined functionally, rather than structurally.

Moreover, as described above, variant forms of Tvu DNA polymerase are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of Tvu DNA polymerase containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs well known in the art, for example LASERGENE software (DNASTAR Inc., Madison, Wis.).

When a Tvu DNA polymerase enzyme of the present invention has an amino acid residue sequence that is not identical to that of SEQ ID NO: 2, 4 or 6 because one or more conservative substitutions has been made, it is preferred that no more than 20 percent, and more preferably no more than 10 percent, and most preferably no more than 5 percent of the amino acid residues are substituted as compared to SEQ ID NO: 2, 4 or 6.

A contemplated Tvu DNA polymerase can also have a length shorter than that of SEQ ID NO: 2 and maintain DNA synthesis activity. The first 284 amino acids at the amino terminus can be deleted as in an enzymes of SEQ ID NO: 4 and 6. Such variants exhibit DNA synthesis activity as discussed elsewhere herein and exhibit DNA synthesis activity at temperatures higher than about 50° C.

This invention further contemplates a method for generating sets of combinatorial mutants of the present Tvu DNA polymerase, as well as deletion mutants, and is especially useful for identifying potential variant sequences (i.e., homologs) with unique DNA synthetic activity. The purpose of screening such combinatorial libraries is to generate, for example, novel Tvu DNA polymerase homologs that possess novel activities.

In some embodiments of the combinatorial mutagenesis approach of the present invention, the amino acid sequences for a population of Tvu DNA polymerase homologs or other related proteins are aligned, preferably to promote the highest homology possible. Such a population of variants can include, for example, DNA polymerase homologs from one or more species, or Tvu DNA polymerase homologs from the same species but which differ due to mutation. Amino acids appearing at each position of the aligned sequences are selected to create a degenerate set of combinatorial sequences.

In a preferred embodiment of the present invention, the combinatorial Tvu DNA polymerase library is produced by way of a degenerate library of genes encoding a library of polypeptides including at least a portion of potential Tvu DNA polymerase-protein sequences. For example, a mixture of synthetic oligonucleotides are enzymatically ligated into gene sequences such that the degenerate set of potential Tvu DNA polymerase sequences are expressible as individual polypeptides, or alternatively, as a set of larger fusion proteins (e.g., for phage display) containing the set of Tvu DNA polymerase sequences therein.

There are many ways in which the library of potential Tvu DNA polymerase homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Tvu DNA polymerase sequences. The synthesis of degenerate oligonucleotides is well known in the art (e.g., Narang, Tetrahedron 39:39, 1983; Itakura et al., Recombinant DNA, Proc 3rd Cleveland Sympos. Macromol., Walton, ed., Elsevier, Amsterdam, pp 273–289, 1981; Itakura et al., Annu. Rev. Biochem. 53:323, 1984; Itakura et al., Science 198:1056, 1984; and Ike et al., Nucleic Acid Res. 11:477, 1983). Such techniques have been employed in the directed evolution of other proteins (e.g., Scott et al., Science 249:386–390, 1980; Roberts et al., PNAS 89:2429–2433, 1992; Devlin et al., Science 249: 404–406, 1990; Cwirla et al., PNAS 87: 6378–6382, 1990; as well as U.S. Pat. Nos. 5,223,409, 5,198,346, and 5,096,815, each of which is incorporated herein by reference).

A wide range of techniques are known in the art for screening gene products of combinatorial libraries generated by point mutations, and for screening cDNA libraries for gene products having a particular property of interest. Such techniques are generally adaptable for rapid screening of gene libraries generated by the combinatorial mutagenesis of Tvu DNA polymerase homologs. The most widely used techniques for screening large gene libraries typically comprise cloning the gene library into replicable expression vectors, transforming appropriate cells with the resulting library of vectors, and expressing the combinatorial genes under conditions such that detection of a desired activity facilitates relatively easy isolation of the vector encoding the gene whose product was detected. The illustrative assays described below are amenable to high through-put analysis as necessary to screen large numbers of degenerate sequences created by combinatorial mutagenesis techniques.

In some embodiments of the present invention, the gene library is expressed as a fusion protein on the surface of a viral particle. For example, foreign peptide sequences can be expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of viral replication. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (e.g., WO 90/02909; WO 92/09690; Marks et al., J. Biol. Chem., 267:16007–16010, 1992; Griffths et al., EMBO J., 12:725–734, 1993; Clackson et al., Nature, 352:624–628, 1991; and Barbas et al., PNAS 89:4457–4461, 1992).

In another embodiment of the present invention, the recombinant phage antibody system (e.g., RPAS, Pharmacia Catalog number 27-9400-01) is modified for use in expressing and screening Tvu polymerase combinatorial libraries. The pCANTAB 5 phagemid of the RPAS kit contains the gene encoding the phage gIII coat protein. In some embodiments of the present invention, the Tvu polymerase combinatorial gene library is cloned into the phagemid adjacent to the gIII signal sequence such that it will be expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate Tvu polymerase gene insert. The resulting recombinant phage contain phagemid DNA encoding a specific candidate Tvu polymerase-protein and display one or more copies of the corresponding fusion coat protein. In some embodiments of the present invention, the phage-displayed candidate proteins that are capable of, for example, binding nucleotides or nucleic acids, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning greatly enriches for Tvu polymerase homologs, which are then screened for further biological activities.

In light of the present disclosure, other forms of mutagenesis generally applicable will be apparent to those skilled in the art in addition to the aforementioned rational mutagenesis based on conserved versus non-conserved residues. For example, Tvu DNA polymerase homologs can be generated and screened using, for example, alanine scanning mutagenesis and the like (Ruf et al., Biochem., 33:1565–1572, 1994; Wang et al., J. Biol. Chem., 269:3095–3099, 1994; Balint et al. Gene 137:109–118, 1993; Grodberg et al., Eur. J. Biochem., 218:597–601, 1993; Nagashima et al., J. Biol. Chem., 268:2888–2892, 1993; Lowman et al., Biochem., 30:10832–10838, 1991; and Cunningham et al., Science, 244:1081–1085, 1989); linker scanning mutagenesis (Gustin et al., Virol., 193:653–660, 1993; Brown et al., Mol. Cell. Biol., 12:2644–2652, 1992; McKnight et al., Science, 232:316); or saturation mutagenesis (Meyers et al, Science, 232:613, 1986).

In some embodiments, the wild-type Tvu polymerase is cloned by isolating genomic DNA using molecular biological methods. The isolated genomic DNA is then cleaved into fragments (e.g., about 3 kb or larger) using restriction enzymes and the fragments are inserted into a suitable cloning vector such as a plasmid or bacteriophage vector. The vectors containing fragments of *T. vulgaris* genomic DNA are then transformed into a suitable *E. coli* host. Clones containing DNA encoding the Tvu polymerase may be isolated using functional assays (e.g., presence of thermostable polymerase in lysates of transformed cells) or by hybridization using a probe derived from a region of conservation among DNA polymerases derived from thermostable organisms. Alternatively, the *T. vulgaris* genomic DNA may be used as the target in PCR with primers selected from regions of high sequence conservation among the genes encoding thermostable DNA polymerases. Although such a PCR may not amplify the entire coding region of the Tvu polymerase I gene, the full-length Tvu gene can be isolated by using the amplified fragment as a probe to screen a genomic library containing *T. vulgaris* DNA.

Once the full-length Tvu polymerase gene is obtained, the region encoding the 5' to 3' exonuclease may be altered by a variety of means to reduce or eliminate these activities. Suitable deletion and site-directed mutagenesis procedures are known in the art.

In some embodiments of the present invention, deletion of amino acids from the protein is accomplished either by deletion in the encoding genetic material, or by introduction of a translational stop codon by mutation or frame shift. In other embodiments, proteolytic treatment of the protein molecule is performed to remove portions of the protein. In still further embodiments, deletion mutants are constructed by restiction digesting the wild-type sequence and introducing a new start site by annealing an appropriately designed oligomer to the digested fragment encoding the desired activity (e.g., Example 11).

6. Chemical Synthesis of Tvu DNA Polymerase

In an alternate embodiment of the invention, the coding sequence of Tvu DNA polymerase is synthesized, whole or in part, using chemical methods well known in the art (e.g., Caruthers et al., Nuc. Acids Res. Symp. Ser., 7:215–233, 1980; Crea and Horn, Nuc. Acids Res., 9:2331, 1980; Matteucci and Caruthers, Tetrahedron Lett., 21:719, 1980; and Chow and Kempe, Nuc. Acids Res., 9:2807–2817, 1981). In other embodiments of the present invention, the protein itself is produced using chemical methods to synthesize either a full-length Tvu DNA polymerase amino acid sequence or a portion thereof. For example, peptides can be synthesized by solid phase techniques, cleaved from the resin, and purified by preparative high performance liquid chromatography (e.g., Creighton, *Proteins Structures and Molecular Principles*, W H Freeman and Co, New York N.Y., 1983). In other embodiments of the present invention, the composition of the synthetic peptides is confirmed by amino acid analysis or sequencing (e.g., Creighton, supra).

Direct peptide synthesis can be performed using various solid-phase techniques (Roberge et al., Science 269:202–204, 1995) and automated synthesis may be achieved, for example, using ABI 431A Peptide Synthesizer (Perkin Elmer) in accordance with the instructions provided by the manufacturer. Additionally, the amino acid sequence of Tvu DNA polymerase, or any part thereof, may be altered during direct synthesis and/or combined using chemical methods with other sequences to produce a variant polypeptide.

III. Use of Tvu DNA Polymerases in PCR

The wild-type and modified Tvu polymerases of the present invention provide suitable enzymes for use in PCR. The PCR process is described in U.S. Pat. Nos. 4,683,195 and 4,683,202, the disclosures of which are incorporated herein by reference.

Any nucleic acid may be amplified by PCR methods of the present invention, so long as the nucleic acid contains regions complementary to the primer set. Examples of suitable nucleic acids include, but are not limited to, DNA, cDNA, chromosomal DNA, plasmid DNA, RNA, rRNA, and mRNA. The nucleic acid may be from any source, including, but not limited to, bacteria, viruses, fungi, protozoa, yeast, plants, animals, blood, tissues, and in vitro synthesized nucleic acids.

IV. Use of Tvu DNA Polymerases for Reverse Transcription

The present invention also contemplates the use of Tvu DNA polymerase for reverse transcription reactions. Reverse transcription of many RNA templates by commonly used reverse transcriptases (e.g., Avian myeloblastosis virus (AMV) reverse transcriptase and Moloney murine leukemia virus (MMLV) reverse transcriptase) is often limited by the secondary structure of the RNA template. Secondary structure in RNA results from hybridization between complementary regions within a given RNA molecule. Secondary structure causes poor synthesis of cDNA and premature termination of cDNA products, because these polymerases are unable to process through the secondary structure. Therefore, RNAs with secondary structure may be poorly represented in a cDNA library and it may be difficult to detect the presence of RNA with secondary structure in a sample by reverse transcription PCR (RT-PCR). Furthermore, secondary structure in RNA can cause inconsistent results in techniques such as differential display PCR. Accordingly, it is advantageous to conduct reverse transcription reactions at increased temperatures so that secondary structure is removed or limited.

Several thermostable DNA polymerases (e.g., *Thermus thermophilus* DNA polymerase, *Anaerocellum thermophilum* DNA polymerase [e.g., WO 98/14588]) possess reverse transcriptase activity. As these enzymes can be used at higher temperatures than retroviral reverse transcriptases, much of the secondary structure of RNA molecules is removed (i.e., due to thermal melting of the RNA structure). The reverse transcriptase activity of many of these polymerases is only observed in the presence of manganese ions, however, exceptions include *Anaerocellum thermophilium* DNA polymerase (e.g., WO 98/14588), *Bacillus caldotenax* DNA polymerase (e.g., U.S. Pat. No. 5,436,149), and C. THERM DNA polymerase (Boehringer Mannheim). Reverse transcription reactions conducted in the presence of manganese are often suboptimal because the presence of manganese ions lowers the fidelity of the polymerase and can cause damage to polynucleotides.

The present invention provides improvements in reverse transcriptase methods through the use of Tvu polymerase. Thus, in some embodiments of the present invention, the Tvu polymerase reverse transcriptase activity is utilized. In some embodiments, the reverse transcriptase activity is exhibited in the presence of magnesium or manganese ions. In other embodiments, the polymerase exhibits reverse transcriptase activity in the presence of magnesium ions and the substantial absence of manganese ions. Therefore, the present invention encompasses various reverse transcription methods using Tvu polymerase. In some embodiments; the reverse transcription reaction is conducted at about 50° C. to 80° C., preferably about 60° C. to 75° C. In still further embodiments, reverse transcription of an RNA molecule by Tvu polymerase results in the production of a cDNA molecule complementary to the RNA molecule. In other embodiments, the Tvu polymerase then catalyzes the synthesis of a second strand DNA complementary to the cDNA molecule to form a double stranded DNA molecule. In still further embodiments, the Tvu polymerase catalyzes the amplification of the double stranded DNA molecule in a PCR as described above. In some embodiments, the PCR is conducted in the same reaction mix as the reverse transcriptase reaction (i.e., coupled RT-PCR).

V. Use of Tvu DNA Polymerases in DNA Sequencing Methods

The present invention also contemplates the use of Tvu DNA polymerase in sequencing reactions. Thermal cycle sequencing is an alternative method for enzymatic sequence analysis that takes advantage of the intrinsic properties of thermophilic DNA polymerases, such as the one isolated from *Thermus aquaticus* (*Taq* DNA polymerase). Because the protocol utilizes a thermocycling apparatus, several advantages are realized over conventional sequencing strategies. First, the protocol yields a linear amplification of the template DNA, reducing the amount of template required to achieve a detectable sequence ladder. Using a $^{32}$P end-labeled primer, greater than 500 bases of sequence can be obtained from as little as 4 fmol ($4\times10^{-15}$ moles) of template after an overnight exposure. Secondly, the high temperatures employed during each denaturation cycle eliminate the requirement for alkaline denaturation and ethanol precipitation of double-stranded DNA (dsDNA) templates: The denaturation cycles also help to circumvent problems.associated with rapid reannealing of linear dsDNA templates such as PCR reaction products. Third, high annealing temperatures increase the stringency of primer hybridization. Fourth, the high polymerization temperature decreases the secondary structure of DNA templates and thus permits polymerization through highly structured regions (Innis et al., Proc. Natl. Acad. Sci USA 85:9436, 1988). Thermal cycle sequencing is useful for sequencing a wide variety of templates such as recombinant DNA, amplified DNA, large double-stranded DNA templates such as lambda, GC-rich templates and palindrome-rich templates.

In some embodiments of the present invention, Tvu DNA polymerase is used to sequence nucleic acids. The sequence of a deoxyribonucleic acid molecule can be elucidated using chemical (Maxam and Gilbert, Proc. Natl. Acad. Sci. USA 74:560, 1977) or enzymatic (Sanger et al., Proc. Natl. Acad. Sci. USA 74:5463, 1977) methods. The enzymatic sequencing method is based on the ability of a DNA polymerase to extend a primer hybridized to the template that is to be sequenced until a chain-terminating nucleotide is incorporated (referred to as "chain terminating sequencing"). Each sequence determination is carried out as a set of four separate reactions, each of which contains all four deoxyribonucleoside triphosphates (dNTP) supplemented with a limiting amount of a different dideoxyribonucleoside triphosphate (ddNTP). Because ddNTPs lack the 3'-OH group necessary for chain elongation, the growing oligonucleotide is terminated selectively at G, A, T, or C, depending on the respective dideoxy analog in the reaction.

The relative concentrations of each of the dNTPs and ddNTPs can be adjusted to give a nested set of terminated chains over several hundred to a few thousand bases in length. The resulting fragments, each with a common origin but ending in a different nucleotide, are separated according to size by high-resolution denaturing gel electrophoresis.

Incorporation of a label (e.g., a radiolabel or a fluorescent label) into the oligonucleotide chain permits the visualization of the sequencing products by autoradiography or fluorescence detection. The end-labeled primer protocol, a modification of a described procedure (Heiner et al., Applied Biosystems, Inc. DNA Sequencer Model 370 User Bulletin-Taq Polymerase: Increased Enzyme Versatility in DNA Sequencing, 1988), uses [$\gamma$-$^{32}$P]ATP, [$\gamma$-$^{33}$P]ATP or [$\gamma$-$^{35}$S] ATP to label the sequencing primer. Alternatively, primers containing a fluorescent dye at the 5' terminus may be employed. The DNA template and labeled primer are repeatedly annealed and enzymatically extended/terminated in thermal cycle sequencing. The end-labeled primer protocol is the most versatile sequencing method and is useful when working with lambda DNA (Kaledin et al., Biokhimiya 45:494, 1980), PCR templates, and any template where false priming may be a problem. This protocol generates sequence data very close to the primer and is recommended when this is needed. The reaction also contains deaza nucleotide mixes that substitute 7-deaza dGTP for dGTP. The deaza mixes resolve band compressions associated with GC-rich regions (Mizusawa et al., Nucl. Acids Res. 14:1319, 1986, and Barr et al., Biotechniques 4:428, 1986).

U.S. Pat. No. 4,707,235 (the disclosure of which is herein incorporated by reference) provides an automated system for the electrophoresis and analysis of radiolabelled products using a multichannel electrophoresis apparatus that is useful in sequencing. It is contemplated that Tvu polymerase will find use in this method as well.

EXAMPLES

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); fmol (femtomole); HPLC (high pressure liquid chromatography); DTT (dithiothreitol); DMF (N, N dimethyl formamide); DNA (deoxyribonucleic acid); p (plasmid); μl (microliters); ml (milliliters); μg (micrograms); pmoles (picomoles); mg (milligrams); MOPS (3-[N-Morpholino]propanesulfonic acid); M (molar); mM (milliMolar); μM (microMolar); nm (nanometers); kd (kilodaltons); OD (optical density); EDTA (ethylene diamine tetra-acetic acid); FITC (fluorescein isothiocyanate); SDS (sodium dodecyl sulfate); $NaPO_4$ (sodium phosphate); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); SDS-PAGE (sodium dodecyl sulfate polyacrylamide gel electrophoresis); Tween (polyoxyethylene-sorbitan); Boehringer Mannheim or BM (Boehringer Mannheim, Indianapolis, Ind.); Epicentre (Epicentre Technologies, Madison, Wis.); New England Biolabs or NEB (New England Biolabs, Beverly, Mass.); Novagen (Novagen, Inc., Madison, Wis.); Pharmacia (Pharmacia Biotech Inc., Piscataway, N.J.); Perkin Elmer (Perkin Elmer, Norwalk, Conn.); Promega (Promega Corp., Madison, Wis.); Qiagen (Qiagen Inc., Chatsworth, Calif.); Spectra (Spectra, Houston, Tex.); Stratagene (Stratagene Cloning Systems, La Jolla, Calif.); USB (U.S. Biochemical, Cleveland, Ohio); Tomah (Tomah Products Inc., Tomah, Wis.).

Example 1

Purification of Tvu DNA Polymerase

This example describes the purification of native *T. vulgaris* (*Tvu*) DNA polymerase. Tvu cells were obtained from the ATCC (Accession Number 43649). This purified polymerase was then used in the experiments represented in Examples 2 through 10. One milliliter from the frozen seed vial was thawed and inoculated into 1 liter Luria broth. The medium was supplemented with 10 ml of 20% glucose. The culture was grown for 15 hours on a shaker at 55° C. and 250 rpm. Five hundred milliliters of this culture were added to 17.5 liters medium in a 20-liter fermenter. The culture was grown at 55° C. The culture growth was monitored spectrophotometrically at 580 nm and measured based on wet weight of cell pellets from 40 ml of broth. After 4.75 hours, the contents were chilled and harvested using a CEPA tubular bowl centrifuge. The net yield of cell paste was 69.0 g. The cell paste was stored in a freezer at −85° C., until purification of Tvu DNA polymerase was performed.

Thirty grams of cell paste were suspended in ice cold 150 ml 0.25 M NaCl TEDGT buffer (50 mM Tris-HCl at pH 7.3, 1 mM EDTA, 1 mM DTT, 10% Glycerol, and 0.1% Tween 20) containing 2.5 mM PMSF, and lysed by sonication on ice. Then 11.5 ml of 5% PEI was added to the lysate to precipitate the DNA. The following purification steps were performed at 4° C. Centrifugation (15,000 rpm in a Beckman JA18 rotor for 15 minutes) was used to separate the supernatant from the precipitate. The supernatant was then collected, and ammonium sulfate was added to a final saturation of 65% to precipitate the DNA polymerase. Centrifugation (15,000 rpm in a Beckman JAI8 rotor for 20 minutes) was used to separate the ammonium sulfate precipitate from the supernatant. The precipitate was collected, suspended in TEDGT buffer and dialyzed against TEDGT buffer to remove the ammonium sulfate.

The dialyzed solution was then loaded onto a Heparin-Agarose column (SPL 1905-0004) equilibrated with TEDGT buffer. After washing the column with TEDGT buffer, elution was performed by applying a linear gradient of 0 to 1 M NaCl TEDGT buffer. The fractions were collected, and assayed for DNA polymerase activity as described in Example 2. Fractions with DNA polymerase activity were pooled. The presence of endonucleases was determined by incubating the equivalent of 1/64, 1/16, 1/8, 1/4, 1/2, and 1 μl of the pooled fractions with 1 μg lambda DNA (Promega, D150) in buffer E (Promega, R005A) for one hour at 74° C. Agarose gel analysis of the digest showed no restriction enzyme activity. The pooled fractions were dialyzed against TEDGT buffer, then loaded onto a TEDGT buffer equilibrated Cibacron Blue column (Sigma, C-1535). After washing the column with TEDGT buffer, elution was performed with a linear gradient of 0 to 1 M NaCl TEDGT buffer. The eluate was collected in fractions, and each fraction was assayed for DNA polymerase activity.

Fractions that contained DNA polymerase activity were pooled, dialyzed against TEDGT buffer, and loaded onto a TEDGT buffer equilibrated DEAE-Sepharose column (Sigma, DCL-6B-100). After washing the column with TEDGT buffer, elution was performed with a linear gradient of 0 to 1 M TEDGT buffer. The eluate was collected in fractions, and assayed for DNA polymerase activity. The fraction that showed the highest DNA polymerase activity was dialyzed against TEDGT buffer before it was loaded onto a TEDGT equilibrated DNA-Agarose column (Promega). After washing the column with TEDGT buffer, elution was performed with a linear gradient of 0 to 1 M NaCl TEDGT buffer. The eluate was collected in fractions, and assayed for DNA polymerase activity. Endonuclease and nickase activities were assayed by incubating 5 μl of fractions with the highest DNA polymerase activity with 1 μg of PhiX174 DNA digested with Hae III restriction enzyme (Promega, G176A) or pBR322 plasmid DNA (Promega D151A) in buffer E (Promega R005A) for 3 1/3 hours at 70° C. Fractions that showed highest level of DNA polymerase activity and no substantial endonuclease or nickase activity were pooled to yield a 3 ml solution. Sixty microliters 10% Tween 20 and 60 μl 10% NP40 detergents were added, and dialyzed against the storage buffer (20 mM Tris-HCl pH8.0, 100 mM KCl, 0.1 mM EDTA, 1 mM DTT, 50% glycerol, 0.5% NP-40, and 0.5% Tween 20), diluted with the storage buffer to a concentration of 5 units (as defined in Example 2) per microliter and stored at −20° C.

This experiment demonstrated that the Tvu DNA polymerase was purified to greater than 95% pure as indicated by the substantial absence of nuclease contamination, and a predominant band at about 97 kD when compared to Mark 12 size markers (Novex, LC5677) on a 4–20% gradient Tris-Glycine gel (Novex EC6025).

Example 2

DNA Polymerization Activity Assay

Activity of native, thermostable Tvu. DNA polymerase purified as described in Example 1 was assayed by incorporation of radiolabeled dTTP into nicked and gapped (i.e., activated) calf thymus DNA prepared as described below. One unit of thermostable DNA polymerase is defined as the amount of enzyme required to catalyze the incorporation of 10 nmol of dNTP into an acid-insoluble form in 30 minutes at 74° C. The reaction conditions comprised: 50 mM Tris-HCl (pH 9.0 at 25° C.), 50 mM NaCl, 10 mM $MgCl_2$, 12 μg activated calf thymus DNA, 0.2 mM dATP, 0.2 mM dGTP, 0.2 mM dCTP, 0.2 mM dTTP (Promega, U1240), and 1 μCi of $^3$HdTTP (Amersham, #TRK.424) per 50 μl reaction.

The reaction components were assembled at room temperature. Samples suspected of containing polymerase activity were added (5 μl containing 0.05 to 0.5 units) and the tube was incubated at 74° C. for 30 minutes. Then, 50 μl aliquots were removed at 6, 9, 12, and 15 minutes and placed in separate tubes on ice. The $^3$H-dTTP incorporation was determined by measuring TCA precipitation counts by the following procedure. To each 50 μl aliquot, 500 μl 10% cold TCA solution was added and the tubes were incubated on ice for 10 minutes before the contents of each tube were filtered onto a separate GF/A filter (Whatman, 1820 024). The filters were washed with 5 ml 5% cold TCA solution three times, and once with acetone. The filters were dried under a heat lamp, put into a scintillation vial, and then counted in a liquid scintillation counter in scintillation fluid (Beckman, 158735). A no-enzyme negative control was also performed using 50 μl DNA polymerase activity assay mix and washed as above. The total counts of each reaction were determined using 5 μl of DNA polymerase activity assay mix directly.

Activated calf thymus DNA was prepared by dissolving 1 g calf thymus DNA (#D-151, Sigma) in 400 ml TM buffer (10 mM Tris-HCl (pH 7.3), 5 mM MgCl2). Four hundred microliters of a solution containing 40 unites of RQ1-DNase (Promega) in TM buffer was added to the DNA solution and incubated at 37° C. for 10 minutes. The DNase digestion was stopped by heating the DNA solution at 68° C. for 30 minutes. The activated calf thymus DNA was stored at −20° C. until used. The activated calf thymus DNA was heated to 74° C. for 10 minutes and then cooled to room temperature before use.

Example 3

Comparison of RT Activity of Thermostable DNA Polymerases in the Presence of $Mg^{2+}$ or $Mn^{2+}$ Ions This example describes the determination of the reverse transcriptase activity of several different DNA polymerases in the presence of either $Mg^{2+}$ or $Mn^{2+}$ ions. In these experiments, a reverse transcription (RT) reaction mix was used. The final concentration of each component in a reaction was: 10 mM Tris-HCl (pH 8.3), 90 mM KCl, 0.5 mM dTTP (Promega, U123A), 0.25 mM polyriboadenylate, 0.025 mM oligodeoxythymidylate (Supertechs 111020A), and 0.25 μCi 3HdTTP (Amersham Life Science, catalog #TRK.424) in 50 μl reaction volume.

Each 45 μl aliquot of the RT reaction mix was mixed with 2 μl (10 units) of one of the DNA polymerases, and 1 μl of either 50 mM $MnCl_2$ or 50 mM $MgCl_2$. The solutions were then incubated at 70° C. for 15 minutes. Reactions were stopped by placing them on ice native Taq, sequencing grade Taq (sTaq), and Tth were from Promega (M166, M203, M210 respectively), Tne was purified as described in U.S. Pat. No. 6,001,645 incorporated herein by reference. The negative control was performed as described but without addition of any enzyme.

The $^3$HdTTP incorporation was determined by measuring TCA precipitation counts as follows. Each RT reaction was TCA precipitated by adding 10 μl calf thymus DNA (1 mg/ml), 500 μl 10% cold TCA solution, and then allowed to sit on ice for 10 minutes before it was filtered onto GF/C filter (Whatman, 1822024). The filter was washed with 5 ml 5% cold TCA solution three times, and once with acetone. The filter was dried under a heat lamp, and then counted in a liquid scintillation counter in scintillation fluid (Beckman, 158735). The results (corrected for background) are presented in Table 2.

TABLE 2

| Reverse Transcriptase Activity | | | |
|---|---|---|---|
| Enzyme | $MnCl_2$ (mM) | $MgCl_2$ (mM) | $^3$H-dTTP Incorporation (CPM) |
| native Tvu | 1 | — | 35654 |
| native Tvu | — | 1 | 10502 |
| Taq | 1 | — | 11110 |
| Taq | — | 1 | 70 |
| sTaq+ | 1 | — | 9920 |
| sTaq+ | — | 1 | 192 |
| Tth | 1 | — | 11201 |
| Tth* | 1 | — | 19988 |
| Tth* | — | 1 | 160 |
| Tne | 1 | — | 14456 |
| Tne | — | 1 | 114 |

*Reaction was done in 0.05% Tomah E-18-15 detergent
+Sequencing grade Taq

This experiment demonstrated that: 1) the DNA polymerases tested had high RT activity in the presence of $Mn^{2+}$; 2) addition of 0.05% Tomah E-18–15 detergent (See, e.g., U.S. patent application Ser. No. 09/338,174, incorporated herein by reference) increased Tth RT activity by 80% in $Mn^{2+}$ buffer; and 3) of the polymerases tested, only Tvu DNA polymerase has significant reverse transcriptase activity in the presence of $Mg^{2+}$ ions. As indicated by the data, the reverse transcriptase activity of Tvu DNA polymerase is approximately 150 times higher than native Taq DNA polymerase, approximately 52 times higher than sequencing-grade Taq DNA polymerase, approximately 66 times higher than Tth DNA polymerase, and approximately 92 times higher than Tne DNA polymerase in the presence of 1 mM $MgCl_2$.

Example 4

Reverse Transcriptase Activity of Tvu DNA Polymerase Tested Over a Range of Magnesium Concentrations This example describes the determination of the magnesium ion concentration at which Tvu DNA polymerase has the highest reverse transcriptase activity. A reverse transcription (RT) reaction mix was prepared as described in Example 3 above, except that 10 mM KCl (i.e., instead of 90 mM KCl) was used in the 10×RT buffer. The mix components and their concentrations are indicated in Table 3.

TABLE 3

| Component | Amount | | | | | | | | |
|---|---|---|---|---|---|---|---|---|---|
| | Reverse Transcriptase Reactions | | | | | | | | |
| 50 mM $MgCl_2$ (μl) | 1 | 1.5 | 2 | 2.5 | 0 | 0 | 0 | 0 | 0 |
| 100 mM $MgCl_2$ (μl) | 0 | 0 | 0 | 0 | 1.5 | 1.75 | 2 | 2.5 | 0 |
| 5u/μl Tvu (μl) | 2 | 2 | 2 | 2 | 2 | 2 | 2 | 2 | 0 |
| RT reaction mix (μl) | 45 | 45 | 45 | 45 | 45 | 45 | 45 | 45 | 45 |
| | $Mg^{2+}$ Concentration in Each Reaction (mM) | | | | | | | | |
| | 1.0 | 1.5 | 2.0 | 2.5 | 3.0 | 3.5 | 4.0 | 5.0 | 0 |

Each reaction was incubated at 70° C. for 20 minutes. Reactions were stopped by placing them on ice. The $^3$HdTTP incorporation was determined by measuring TCA precipitation counts as described in Example 3. The results are presented in Table 4 (all values shown were corrected for background).

TABLE 4

| Reverse Transcriptase Assay | |
|---|---|
| $MgCl_2$ (mM) | $^3$HdTTP Incorporation (CPM) |
| 1.0 | 14464 |
| 1.5 | 22787 |
| 2.0 | 25427 |
| 3.0 | 32395 |
| 3.5 | 25580 |
| 4.0 | 27472 |
| 5.0 | 26487 |

This experiment demonstrates that the reverse transcriptase activity of Tvu DNA polymerase increased at levels from 1 to 3 mM $Mg^{2+}$, was maximum at 3 mM $Mg^{2+}$, and then decreased when the $Mg^{2+}$ concentration was increased above 3 mM.

Example 5

Reverse Transcriptase Activity of Tvu DNA Polymerase Tested Over a Range of Manganese Ion Concentrations This experiments describes the determination of the optimum $Mn^{2+}$ concentration for reverse transcriptase activity. A reverse transcription (RT) reaction mix was prepared as described in Example 3, except that Tomah E-18-15 detergent was added to a final concentration of 0.01%, and Tvu DNA polymerase was added to a final concentration of 0.07 units per μl of RT reaction mix. The mix cornponents are indicated in Table 5.

TABLE 5

| Component | Amount | | | | | | |
|---|---|---|---|---|---|---|---|
| Reverse Transcription Reactions | | | | | | | |
| 25 mM $MnCl_2$ (μl) | 0 | 0 | 1.2 | 1.4 | 1.6 | 1.8 | 2.0 |
| 10 mM $MnCl_2$ (μl) | 2 | 2.5 | 0 | 0 | 0 | 0 | 0 |
| RT reaction mix (μl) | 45 | 45 | 45 | 45 | 45 | 45 | 45 |
| $Mn^{2+}$ Concentration in Each Reaction (mM) | | | | | | | |
| | 0.4 | 0.5 | 0.6 | 0.7 | 0.8 | 0.9 | 1.0 |

Each reaction was incubated at 74° C. for 20 minutes. Reactions were stopped by placing them on ice. The $^3$HDTTP incorporation was determined by measuring TCA precipitation counts as described in Example 3. The results are shown in Table 6 (all values shown were corrected for background).

TABLE 6

| Reverse Transcriptase Activity | |
|---|---|
| $MnCl_2$ (mM) | $^3$HdTTP incorporation (CPM) |
| 0.4 | 7670 |
| 0.5 | 8258 |
| 0.6 | 9200 |
| 0.7 | 8718 |
| 0.8 | 7600 |
| 0.9 | 7616 |
| 1.0 | 7610 |

This experiment demonstrates that the reverse transcriptase activity of Tvu DNA polymerase increased as the level of $Mn^{2+}$ in the reaction increased from 0.4 to 0.6 mM, was maximum at 0.6 mM $Mn^{2+}$, and decreased when $Mn^{2+}$ concentration was increased above 0.6 mM.

Example 6

Tvu Reverse Transcriptase Activity in $Mg^{2+}$ Buffer

This example measures the reverse transcriptase (RT) activity of Tvu DNA polymerase in a buffer containing magnesium. In these experiments, a RT reaction mix was prepared with the final concentration of each component of the mix in a reaction: 50 mM Tris-HCl (pH 8.3), 40 mM KCl, 0.5 mM dTTP (Promega, U123A), 7mM $MgCl_2$, 10 mM DTT, 0.25 mM polyriboadenylate, 0.025 mM oligodeoxythymidylate (Supertechs, #111020A), and 0.25 Ci $^3$HdTTP (Amersham, TRK.424) in a 50 μl reaction.

A 45 μl aliquot of the RT reaction mix was mixed with 1.25 units enzyme. The solution was then incubated at 74° C. for 15 minutes. The reactions were stopped by placing them on ice. The experiment was repeated for differing amounts of enzyme. A negative control was performed without any enzymes.

The results are presented in Table 7 (all values shown were corrected for background)

TABLE 7

| Reverse Transcriptase Activity | |
|---|---|
| Enzyme Units | $^3$HdTTP Incorporation (CPM) Tvu DNA Polymerase at 74° C. |
| 1.25 | 2054 |
| 2.5 | 2890 |
| 5 | 15786 |

Example 7

This example was performed to determine the thermostability of Tvu DNA Polymerase. Tvu DNA polymerase (0.08 units) was added to 55 μl of DNA polymerase activity assay mix described in Example 2. The solution was incubated at 70° C. for 10 minutes. The reaction was terminated by placing the tube on ice. The $^3$H-dTTP incorporation was determined by measuring TCA precipitation counts (See Example 2). The experiment was repeated using incubation temperatures of 72, 74, 76, 78, and 80° C. The results are presented in Table 8 (all values were corrected for background).

TABLE 8

| Thermostability | |
|---|---|
| Temperature (° C.) | $^3$H-dTTP Incorporation (CPM) |
| 70 | 7458 |
| 72 | 6556 |
| 74 | 3834 |
| 76 | 1202 |
| 78 | 790 |
| 80 | 596 |

This experiment demonstrates that Tvu DNA polymerase activity decreases as the temperature increases above 70° C. and that the optimal temperature for Tvu DNA polymerase activity is about 70° C. or lower.

Example 8

Tvu Reverse Transcriptase Activity at High Temperature

This example was performed to determine the optimum temperature for the reverse transcriptase activity of Tvu DNA polymerase. A 25 μl solution, containing 2.5 units Tvu DNA polymerase, 2 mM $MgCl_2$, and 1×RT reaction mix (See Example 3) was made. The solution was incubated at 65° C. for 10 minutes. The reaction was then terminated by placing it on ice. The $^3$H-dTTP incorporation was determined by measuring TCA precipitation counts as described in Example 3. The experiment was repeated using incubation temperatures of 68, 70, 72, 74, 76, and 78° C. The results obtained are presented in Table 9 (results were corrected to remove background).

TABLE 9

Reverse Transcriptase Activity at High Temperature

| Temperature (° C.) | $^3$HdTTP Incorporation (CPM) Tvu DNA Polymerase |
|---|---|
| 65 | 1756 |
| 68 | 1906 |
| 70 | 1458 |
| 72 | 1432 |
| 74 | 620 |
| 76 | 560 |
| 78 | 530 |

This experiment demonstrates that Tvu DNA polymerase reverse transcriptase activity increases as the reaction temperature rises from 65° C. to 68° C., is maximum at 68° C., and then decreases at temperatures above 74° C. This suggests that the optimal temperature for the reverse transcriptase activity of Tvu DNA polymerase is approximately 68° C.

Example 9

Tvu DNA Polymerase PCR

To demonstrate that Tvu DNA polymerases can be used to perform PCR, the following experiment was performed. A 49 μl solution, containing PCR buffer, dNTP (Promega U1240), template DNA, primer A, primer B (DNAs described below), and additives (Betaine for Bst, Formamide for Tvu) was made. The solution was incubated in a thermocycler at 95° C. for 2 minutes. The solution was then cooled to and incubated at 65° C. for 2 minutes. During this time, 1 μl Tvu DNA polymerase (5 μ/μl) was added to the solution to bring the final concentration of each component to the following: 10 mM Tris-HCl (pH 7.5), 50 mM NaCl, 10 mM $MgCl_2$, 1.5 mM dNTP, 10 ng template DNA, 1 μM primer A, 1 μM primer B, and 0.5% Formamide for Tvu. The solution was incubated for 35 cycles (75° C. for 15 seconds, and 65° C. for 2 minutes). The final extension reaction was performed at 65° C. for 5 minutes. The reaction was then stored at 4° C. Ten μl of the reaction were then loaded onto a 20% TBE gel (Novex, EC6315). The gel was run at 230 volts for 60 minutes and stained with ethidium bromide. A 36 bp band was detected for both DNA polymerase reactions. This example demonstrates that Tvu DNA polymerase is capable of performing PCR under the conditions described in this example.

In these experiments, Primer A had the following sequence:

5'-GACGTCGCATGCTCCT-3' (SEQ ID NO: 7); Primer B had the following sequence: sequence 5'-ACCGAATTCCTCGAGTC-3' (SEQ ID NO: 8). Template DNA was made by digesting plasmid pGEM-7fz+ (Promega, p225A) with restriction enzymes Apa I and Kpn I.

Example 10

Cloning Recombinant Tvu DNA Polymerases—Wild-type and Mutant Forms

Cloning of Gene Encoding Wild-type Tvu DNA Polymerase

Genomic DNA was isolated from Tvu and used to clone the full-length Tvu DNA polymerase into an expression vector. Two mutant recombinant Tvu DNA polymerases were then constructed, both of which have deleted the 5' to 3' exonuclease-encoding domain. Genomic DNA was isolated from Tvu by resuspending Tvu cells grown overnight in Luria Broth in TE (10 mM Tris, 1 mM EDTA) and vortexing vigorously. The cell solution was then combined with 0.1 mm glass/zircon beads and beaten at 5000 rpm for 2 cycles of 20 seconds each. The cells were then fully dispersed and appeared to be lysed. The liquid was transfered to a fresh tube and extracted twice with phenol and once with chloroform. Each time the aqueous phase was transferred to a clean tube. The aqueous phase was then treated with RNase I and ethanol precipitated. The DNA was spooled and washed in 70% ethanol before drying. The dried DNA pellet was then resuspended in TE to a final concentration of 3 μg/μl.

The DNA polymerase domain was amplified from the Tvu genomic DNA by PCR. The following components were combined:

| | |
|---|---|
| Tvu genomic DNA (predenatured at 98° C., 2 minutes) | 1 ul |
| Primer JH47 (500 picomoles) | 1 ul |
| Primer JH49 (500 picomoles) | 1 ul |
| 10X Taq buffer with 15 mM $MgCl_2$ (Promega) | 5 ul |
| 10 mM dNTPs | 1 ul |
| Nanopure water | 40 ul |

The sequence of the degenerate primers used are conserved in DNA polymerases and are listed below:

JH47 TAGAGCGGCCGCGAYCCIAAYYTICARAAYAT (SEQ ID NO: 9)

JH49 CTGCGGCCGCCTAIIACIAIYTCRTCRTGIAC (SEQ ID NO: 10)

Y indicates a pyrimidine (T or C)

I indicates inosine which anneals with any of the four conventional bases

R indicates a purine (A or G)

The PCR cycling profile was: 96° C., 1 min (94° C., 15 sec; 32° C., 30 sec; 72° C., 1 min)×25 cycles, 72° C. 1 minute. A 600 base pair fragment was produced as expected. The PCR product was purified with Wizard PCR Purification System (Promega, A7170) according to manufacturer's instructions. Twenty-five nanograms of the fragment was ligated to 50 ng T-vector (Promega, A3600) according to manufacturer's instructions. Four microliters of the ligation was transformed into competent JM109 cells. Clones were selected, digested with the Pvu II restriction enzyme and demonstrated to contain the 600 base pair PCR product. The product was sequenced by dideoxy sequencing. When the resulting amino acid sequence encoded by this polynucleotide was compared to the amino acid sequence of *E.coli* PolA and Taq DNA polym erase, it demonstrated about 50% homology to both, indicating that the cloned PCR product originated from the DNA polymerase gene of Tvu.

Oligonucleotide 11300 (5'-GCGCGAAGAACGGCTGCAGGC-3', SEQ ID NO:11) which is within the 600 bp PCR fragment was labelled with $^{33}$P-ATP using T4 polynucleotide kinase and used as a probe for a Southern blot. The Southern blot had Tvu genomic DNA digested with one of seven different restriction enzymes (BamH I, Acc65 I, Apa I, EcoR I, Hind III, Spe I, Xba I, Xho I) per lane. The prehybridization conditions were 65° C., 1.5 hours in 3 ml of 1×SSPE, 10% PEG-8000, 7% SDS, 250 ug/ml denatured Herring Sperm DNA. Hybridization conditions were the same solution as used for the prehybridization with the addition of the radiolabeled probe purified on a G-25 column and reaction at 50° C. for four hours. The washes were 15 to 30 minutes each, 200 ml of 0.3×SSC, 0.1% SDS at 25° C., repeated, followed by three washes of 200 ml of 0.3×SSC, 0.1% SDS at 50° C. The blot was then exposed to X-OMAT film for 2 days at 22° C. There was one band of about 3 kb detectable in the Hind III digested lane and one band larger than 10 kb detectable in the Xho I digested lane.

Tvu genomic DNA was digested with Hind III restriction enzyme and run into a 0.4% TAE agarose gel. The region near the 3 kb position was cut out of the gel, purified with Wizard PCR Purification System (Promega, A7170). The purified 3 kb fragment was ligated into pZERO-2 (Invitrogen) and transformed into TOP10 cells (LTI). Ninety-six clones were picked and each grown in 200 ul LB media containing 30 $\mu$/ml kanamycin, shaking overnight at 37° C. The cultures were dot blotted using oligonucleotide 11300 described above as the probe and prehybridization and hybridization conditions also described above. The washes were two 150 ml washes of 0.5×SSC, 0.1% SDS at 25° C., 15–30 minutes each, followed by three 150 ml washes of 0.5×SSC, 0.1% SDS at 50° C., 15–30 minutes each. The blot was then exposed to X-OMAT film for two hours and developed. Two colonies produced a strong signal. They were grown and plasmid isolated therefrom. The cloned fragments in the plasmids were sequenced and indicated that the Hind III restriction enzyme site was 183 base pairs upstream of the QNIP conserved region indicating about one third of the DNA polymerase gene (the C-terminus) was present in the clone.

To clone upstream of the Hind III site in the gene, a second PCR amplification was designed to amplify the region upstream of the Hind III site. Again, a degenerate primer (JH31) was used that contained conserved sequence present in DNA polymerases. The second primer (11299) was chosen from within the previously cloned Hind III fragment of Tvu DNA polymerase. The following PCR reaction was assembled:

| | |
|---|---|
| Tvu genomic DNA | 1 $\mu$l |
| JH31 primer 400 pmoles | 4 $\mu$l |
| 11299 primer 50 pmoles | 5 $\mu$l |
| 10 mM dNTPs | 1 $\mu$l |
| 10X Taq buffer | 5 $\mu$l |
| 50 mM $MgSO_4$ | 2 $\mu$l |
| Taq polymerase | 1 $\mu$l |
| Water/enhancer | 31 $\mu$l |

JH31 TTCAACCIIAACTCIIIIAICAGCT (SEQ ID NO: 12)

11299 CGGCTCCGACGGCACGAACG (SEQ ID NO: 13)

The PCR cycling conditions were 96° C, 1 minute (94° C., 15 sec; 37° C., 30 sec; 72° C., 1 minute)×25, 72° C., 1 minute. The PCR reaction was run on a 1.2% TBE/agarose gel. The resulting 350 bp band was as expected and was purified using Wizard PCR Purification System (Promega, A7170). The fragment was ligated into a T-vector and transformed into JM109 cells. Positive clones were sequenced. The sequence downstream from the Hind III site was identical to the previous clone. The sequence upstream of the Hind III site encoded amino acids homologous to other DNA polymerases.

New Tvu genomic DNA was isolated as previously described, except cells were lysed with Proteinase K, in order to obtain DNA that was less sheared than the present stock. An oligonucleotide (11761) was prepared using sequence upstream of the Hind III site obtained as described above. This oligonucleotide sequence is listed below:

11761 TCAACACCGGGAGCTGCAGCTTGTCA (SEQ ID NO: 14)

Tvu genomic DNA was digested with Hind III or Hind III plus another restriction enzyme (Acc I, BamH I, Bgl II, EcoR I, Spe I, Xba I, Xho I, Xho II) and each digested sample run on a lane of a 0.6% TBE/agarose gel. The DNA in the gel was transferred to a nylon membrane by Southern blot procedure. The 11761 oligonucleotide was end labelled with $^{33}$P-gamma-ATP using T4 polynucleotide kinase and purified over a NAP-5 column (Pharmacia) according to manufacturer's instructions. Prehybridization, Hybridization, and Wash conditions were as previously described. The membrane was then exposed to X-OMAT film for several days and developed. There was a 4 kb band in all of the lanes except for the Hind III+EcoR I digest lane in which the band was slightly smaller. These results indicate that there is a Hind III restriction enzyme site located about 4 kb upstream of the Hind III site previously localized to the coding sequence of Tvu DNA polymerase.

Tvu genomic DNA was digested with Hind III and run into a 0.6% TBE/agarose gel. The agarose at the 4 kb position was cut out of the gel and the DNA isolated. The resulting DNA was ligated into pZERO-2 (Invitrogen) at the Hind III site and transformed into TOP10 cells. Clones were screened by dot blot as described above using the 11761 radiolabeled olignucleotide as the probe. A positive clone was grown, the plasmid purified, and the insert containing the remainder the Tvu DNA polymerase gene was sequenced.

The two Hind III fragments were cloned in correct order into Litmus 29 plasmid (New England Biolabs) and resequenced across fragment junctions. This full length clone of Tvu DNA polymerase in Litmus 29 plasmid is named L29b. The resulting open reading frame nucleotide sequence is SEQ ID NO: 1.

Mutant Tvu DNA Polymerase Construction—T289M

The construction of T289M mutant of Tvu DNA polymerase resulted in a plasmid containing an IPTG-inducible mammalian promoter directing expression of the Tvu DNA fragment beginning at the nucleotides encoding amino acid 289 of the wild type enzyme, mutated to encode a methionine residue instead of a threonine, and ending at the termination codon of the wild type enzyme.

The JHEX25 vector (Promega) was digested with Nco I and Acc65 I restriction enzymes and the large linear band isolated from an agarose gel. The L29b vector, described above, was digested with Sgf I and Acc65 I restriction enzymes and the 1.8 kb band isolated from an agarose gel. The Sgf I cut site in L29b is located 912 base pairs downstream from the polymerase start codon and the Acc65 I cut site in L29b is located 69 base pairs downstream from the polymerase termination codon.

Oligonucleotides 12144 and 12145 were designed such that when they are annealed to each other an Sgf I overhang exists on one end and an Nco I overhang exists on the other end. The ATG within the Nco I site creates the new, non-native start site for the T289M DNA polymerase. The oligonucleotides were annealed by combining in a tube 2 pmols/$\mu$l of each in TNE (10 mM Tris, 5 mM NaCl, 1 mM EDTA), placing the tube in a 9600 thermocycler and slowly decreasing the temperature from 80° C. to 25° C. over a period of 40 minutes.

The purified Sgf I/Acc65 I fragment of L29b was ligated to 2 pmols of annealed 12144/12145 oligonucleotides using T4 DNA ligase at room temperature for about two hours. Four microliters of the ligation reaction was then transformed into JM109 cells and plated onto LB plates containing tetracycline. Colonies were screened by isolating plasmid and digesting with Nco I and Acc65 I restriction enzymes and further confirmed to be correct by dideoxy sequencing across the sequence encoding the DNA polymerase. The plasmid was named TvuK-25. The nucleotide sequence encoding the T289M polymerase is shown in FIG. 7, SEQ ID NO: 5. The amino acid sequence of T289M polymerase is shown in FIG. 8, SEQ ID NO: 6.

12144 CATGGATGAAGGTGAGAAGCCACTGGCCGGGATGGACTTTGCGAT (SEQ ID NO: 15) 12145 CGCAAAGTCCATCCCGGCCAGTGGCTTCTCACCTTCATC (SEQ ID NO: 16)

Mutant Tvu DNA Polymerase Construction—M285

The construction of the M285 mutant of Tvu DNA polymerase resulted in a plasmid containing an IPTG-inducible mammalian promoter directing expression of the Tvu DNA fragment beginning at the nucleotides encoding the methionine amino acid at position 285 of the wild type enzyme and ending at the termination codon of the wild type enzyme.

The TvuK-25 plasmid described above was digested with Dra I and Sgf I restriction enzymes. The large linear band was isolated from an agarose gel. Oligonucleotides 12230 and 12231 were designed such that when they are annealed to each other an Sgf I overhang exists on one end and a Dra I overhang exists on the other end. The oligonucleotides were annealed by combining in a tube 2 pmols/$\mu$l of each in TNE (10 mM Tris, 5 mM NaCl, 1 mM EDTA), placing the tube in a 9600 thermocycler and slowly decreasing the temperature from 80° C. to 25° C. over a period of 40 minutes.

The purified Sgf I/Dra I fragment of TvuK-25 was ligated to 2 pmols of annealed 12230/12231 oligonucleotides using T4 DNA ligase at room temperature for about two hours. Four microliters of the ligation reaction was then transformed into JM109 cells and plated onto LB plates containing tetracycline. Colonies were screened by isolating plasmid and digesting with either Dra I or AccB7 I restriction enzymes and further confirmed to be correct by dideoxy sequencing across the sequence encoding the DNA polymerase.

The nucleotide sequence encoding the M285 polymerase is shown in FIG. 5, SEQ ID NO: 3. The amino acid sequence of M285 polymerase is shown in FIG. 6, SEQ ID NO: 4. 12230 AAACCATGGCAGTTCAAACCGATGAAGGCGAGAAACCA CTGGCTGGGATGGACTTTGCGAT (SEQ ID NO: 17) 12231 CGCAAAGTCCATCCCAGCCAGTGGTTTCTCGCCTTCATCG GTTTGAACTGCCATGGTTT (SEQ ID NO: 18)

Example 11

Expression and Purification of Recombinant Tvu DNA Polymerases

The recombinant Tvu DNA polymerases, both full-length and mutant, were 10 expressed and purified as described herein. For the full-length clone, a liter of Terrific Broth containing 100 ug/ml ampicillin was grown at 37° C. to saturation with *E.coli* transformed with the vector capable of expressing recombinant full-length Tvu DNA polymerase (described in Example 11). The cells were harvested by centrifugation at 9,000 rpm for 5 minutes.

For the full-length recombinant Tvu DNA polymerase, 20 g cell paste was combined with 200 ml of 0.25 M NaCl TEDG (50 mM Tris-HCl at pH 7.3, 1 mM EDTA, 1 mM DTT, and 10% Glycerol) containing 2.5 mM PMSF. The solution was sonicated at 100% output three times for two minutes each at 10° C. The solution (40 ml aliquots) was then heat treated at 65° C. for 5 minutes and then cooled to 4° C. Then 4 ml of 5% PEI was added to the lysate to precipitate the DNA. The following purification steps were performed at 4° C. Centrifugation (12,000 rpm in a Beckman JA18 rotor for 90 minutes) was used to separate the supernatant from the precipitate. The supernatant was then collected, and ammonium sulfate was added to a final saturation of 65% to precipitate the DNA polymerase. Centrifugation (15,000 rpm in a Beckman JA18 rotor for 30 minutes) was used to separate the ammonium sulfate precipitate from the supernatant. The precipitate was collected, suspended in TEDG buffer and dialyzed against TEDG buffer containing 2.5 mM PMSF overnight to remove the ammonium sulfate.

The dialyzed solution was then loaded onto a Heparin-Agarose column (SPL 1905-0004) equilibrated with TEDG buffer. After washing the column with TEDG buffer, elution was performed by applying a linear gradient of 0 to 0.6 M NaCl TEDG buffer. The 30 fractions were collected, and assayed for DNA polymerase activity as described in Example 2. The presence of endonucleases was determined by incubating 2 $\mu$l of fractions with 1 $\mu$g lambda DNA (Promega, D150) or pBR322 plasmid DNA in activity assay buffer for 17 hours at 70° C. Agarose gel analysis of the digest showed no evidence of nuclease contamination. Fractions with DNA polymerase activity were pooled. The pooled fractions were dialyzed against TEDG buffer, then loaded onto a TEDG buffer equilibrated Cibacron Blue column (Sigma, C-1535). After washing the column with 0.05 M NaCl/TEDG buffer, elution was performed with a linear gradient of 0.05 to 0.75 M NaCl/TEDG buffer. The eluate was collected in fractions, and sample fractions were assayed for DNA polymerase activity and retested for nuclease contamination. No such contamination was detected. The fractions with DNA polymerase activity were pooled and Tomah-34 detergent added to a final concentration of 0.2% (See, e.g., U.S. patent application Ser. No. 09/338,174, incorporated herein by reference). The polymerase solution was then dialyzed overnight against the storage buffer (50% glycercol, 20 mM Tris, pH 8.0 at 25° C., 100 mM KCl, 0.1 mM EDTA, 1 mM DTT, 0.5% Toman-34).

The mutant Tvu DNA polymerases (M285 and T289M) were ed by IPTG-inducible plasmids. For growth of these mutant plasmids, 3 liters of Terrific Broth containing 10 ug/ml tetracycline were seeded separately with 50 ml overnight seedstocks of *E. coli* containing either mutant plasmid. The cultures were grown to about A600=1.5 OD shaking at 37° C. Then the culture growth temperature was adjusted to 25° C. and IPTG was added to a final concentration of 1 mM. The culture was allowed to grow overnight, shaking at 25° C. and the cells were then harvested by centrifugation at 9,000 rpm for 5 minutes. The purification procedure is then the same as that described above for the full-length rTvu DNA polymerase.

This experiment demonstrated that the recombinant Tvu DNA polymerases were purified to greater than 85% as indicated by the substantial absence of nuclease contamination, and a predominant band at about 97 kD for the full-length polymerase and 66 kD for the mutant polymerases when compared to Mark 12 size markers (Novex) on a 4–20% Tris-Glycine gel (Novex EC6025).

Example 13

Use of Recombinant Tvu DNA Polymerases in Reverse Transcription Reaction

Reverse transcription activity in the presence of magnesium ions was measured for the full-length and mutant recombinant Tvu DNA polymerase enzymes purified as described in Example 12.

In these experiments, a reverse transcription (RT) reaction mix was used. The final concentration of each component in a reaction was: 10 mM Tris-HCl (pH 8.3), 50 MM KCl, 0.5 mM dTTP (Promega, U123A), 0.25 mM polyriboadenylate, 0.025 mM oligodeoxythymidylate (Supertechs 111020A), and 0:25 $\mu$Ci $^3$HdTTP (Amersham, TRK.424) in 50 $\mu$l reaction volume.

Each 45 $\mu$l aliquot of the RT reaction mix was mixed with 2 $\mu$l (10 units) or 1 $\mu$l (5 units) of one of the DNA polymerases and water to a final volume of 50 $\mu$l. The solutions were then incubated at 74° C. for 20 minutes. Reactions were stopped by placing them on ice. The negative control was performed as described but without addition of any enzyme.

The $^3$HdTTP incorporation was determined by measuring TCA precipitation counts as follows. Each RT reaction was TCA precipitated by adding 10 $\mu$l calf thymus DNA (1 mg/ml), 500 $\mu$l 10% cold TCA solution, and then allowed to sit on ice for 10 minutes before it was filtered onto GF/C filter (Whatman, 1822024). The filter was washed with 5 ml 5% cold TCA solution three times, and once with acetone. The filter was dried under a heat lamp, and then counted in a liquid scintillation counter in scintillation fluid (Beckman, 158735). The results (corrected for background) are presented in Table 10.

TABLE 10

Reverse Transcription Activity of Recombinant Tvu DNA Polymerase

| Enzyme | Amount of Enzyme | cpm |
|---|---|---|
| Full Length rTvu DNA pol. | 5 units | 12,560 |
| Full Length rTvu DNA pol. | 10 units | 18,794 |
| M285 | 5 units | 13,202 |
| M285 | 10 units | 19,390 |
| T289M | 5 units | 8,434 |
| T289M | 10 units | 16,264 |

The results demonstrate that all recombinant Tvu DNA polymerases tested have reverse transcriptase activity at 74° C., and 10 units produced more activity than 5 units as expected.

Example 14

RT-PCR using Tvu and Taq DNA Polymerase Mixtures

Multiple mixtures of Tvu and Taq DNA polymerases were used, at multiple pH's, to demonstrate that RT-PCR can be performed in a one-pot reaction in the presence of magnesium and the substantial absence of manganese ions.

Kanamycin mRNA (Promega C1381) was used as the nucleic acid substrate in the RT-PCR reactions. The reactions were assembled as detailed in the table below.

| Reaction number: | 1 | 2 | 3 | 4 | 5 |
|---|---|---|---|---|---|
| Reaction mix ($\mu$l) | 43 | 43 | 43 | 43 | 43 |
| Water | 4 | 4 | 4 | 4 | 5 |
| nTaq | 1 | 1 | 1 | 1 | 1 |
| mRNA (0.5 mg/ml) | 1 | 1 | 1 | 1 | 1 |
| nTvu (full-length) | 1 | 0 | 0 | 0 | 0 |
| rTvu (full-length) | 0 | 1 | 0 | 0 | 0 |
| M285 Tvu | 0 | 0 | 1 | 0 | 0 |
| T289M Tvu | 0 | 0 | 0 | 1 | 0 |

The Taq and Tvu DNA polymerases were all at a concentration of 5 units per microliter. nTaq and nTvu are native enzymes, rTvu is the recombinant enzyme. Reaction 5 is the negative control reacton. One set of reactions was at pH 8.3, another set of reactions was at pH 9.0. The reaction mixture was: 5 $\mu$l 10×buffer (500 mM KCl, 100 mM Tris pH 8.3 or 9.0); 5 $\mu$l 2 mM dNTP, 1 $\mu$l Primer 1 (Promega, A109B); 1 $\mu$l Primer 2 (Promega, A110B); 5 $\mu$l 25 mM $MgCl_2$; 26 $\mu$l water.

The PCR cycling program used was 70° C. for 20 minutes to allow for reverse transcription, followed by 95° C. for 1 minute, (94° C. for 15 seconds, 68° C. for 1 minute)×30; 68° C. for 5 minutes, 4° C. soak. An aliquot of the RT-PCR reaction was then run on a 20% TBE gel and ethidium bromide stained to visualize the 300 bp product.

All of the Tvu DNA polymerase enzyme-containing reactions produced robust RT-PCR product when coupled with nTaq DNA polymerase in the above reaction. The RT reaction was run at either 70° C. or 78° C. and both produced nearly equal amounts of RT-PCR product. Likewise, pH 8.3 and pH 9.0 were both efficient and produced nearly equal amounts of RT-PCR product. The mutant and full-length Tvu DNA polymerases produced nearly equal amounts of RT-PCR product.

A 1:10 serial dilution of the mRNA template was performed and the reaction as described above was run using 2 $\mu$l of each dilution and the full-length rTvu DNA polymerase. RT-PCR product of 300 bp was detectable even when using an mRNA dilution containing 1 copy in the 2 $\mu$l aliquot. The negative control reactions containing no Tvu DNA polymerase produced no detectable RT-PCR product.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A composition comprising a purified and isolated DNA polymerase; wherein said DNA polym erase has the amino acid sequence set forth in SEQ ID NO:2; and wherein said DNA polymerase has DNA synthesis activity.

2. The composition of claim 1, wherein said polymerase has a molecular weight of about 97 kD.

3. The composition of claim 1, wherein said polymerase has reverse transcriptase activity in the presence of magnesium ions.

4. The composition of claim 3, wherein said reverse transcriptase activity is substantially manganese ion independent.

5. The composition of claim 1, wherein said DNA polymerase is thermostable.

6. The composition of claim 1, wherein said DNA polymerase is substantially free of endonuclease activity.

7. The composition of claim 1, wherein said DNA polymerase is greater than 85% pure.

8. The composition of claim 1, wherein said DNA polymerase is greater than 95% pure.

9. The polymerase of claim 1, wherein said polymerase is a native polymerase.

10. The polymerase of claim 1, wherein said polymerase is a recombinant polymerase.

11. A purified thermostable mutant DNA polymerase comprising an amino acid sequence selected from the group consisting of SEQ ID NO: 4 and SEQ ID NO: 6.

12. The polymerase of claim 11, wherein said polymerase has DNA synthesis activity, and wherein said polymerase has reverse transcriptase activity.

13. The polymerase of claim 11, wherein said polymerase is substantially free of 5' to 3' exonuclease activity.

* * * * *

SEQUENCE LISTING

<160> NUMBER OF SEQ ID NOS: 39

<210> SEQ ID NO 1
<211> LENGTH: 2631
<212> TYPE: DNA
<213> ORGANISM: Thermoactinomyces vulgaris

<400> SEQUENCE: 1

```
ttgaaaaaca agctcgtctt aattgacggc aacagcgtgg cgtaccgcgc ctttttcgcg     60

ttgccgcttt tgcataacga taaagggatt catacgaacg cagtctacgg gtttacgatg    120

atgttaaaca aaattttggc ggaagagcag ccgacccaca ttctcgtggc gtttgacgcc    180

gggaaaacga cgttccgcca tgaaacgttc caagactata aaggcgggcg gcagcagacg    240

ccgccggaac tgtcggaaca gtttccgctg ctgcgcgaat tgctcaaggc gtaccgcatc    300

cccgcctatg agctcgacca ttacgaagcg gacgatatta tcggaacgat ggcggcgcgg    360

gctgagcggg aagggtttgc agtgaaagtc atttccggcg accgcgattt aacccagctt    420

gcttccccgc aagtgacggt ggagattacg aaaaaaggga ttaccgacat cgagtcgtac    480

acgccggaga cggtcgcgga aaaatacggc ctcaccccgg agcaaattgt cgacttgaaa    540

ggattgatgg gcgacaaatc cgacaacatc cccggcgtgc ccggcatcgg ggaaaaaaca    600

gccgtcaagc tgctcaagca attcggcacg gtcgaaaacg tactggcatc gatcgatgag    660

atcaaagggg agaagctgaa agaaaatttg cgccaatacc gggatttggc gcttttaagc    720

aaacagctgg ccgccattcg ccgcgacgcc ccagttgagc tgacgctcga tgacattgtc    780

tacaaaggag aagaccggga aaaagtggtc gccttattta aggagctcgg gttccagtcg    840

tttctcgaca agatggccgt ccaaacggat gaaggcgaga agccgctcgc cgggatggac    900

tttgcgatcg ccgacggcgt cacggacgaa atgctcgccg acaaggcggc cctcgtcgtg    960

gaggtggtgg gcgacaacta tcaccatgcc ccgattgtcg ggatcgcctt ggccaacgaa   1020

cgcgggcggt tttcctgcg cccggagacg gcgctcgccg atccgaaatt tctcgcttgg   1080

cttggcgatg agacgaagaa aaaaacgatg tttgattcaa agcgggcggc cgtcgcgtta   1140

aaatggaaag gaatcgaact gcgcggcgtc gtgttcgatc tgttgctggc cgcttacttg   1200

ctcgatccgg cgcaggcggc gggcgacgtt gccgcggtgg cgaaaatgca tcagtacgag   1260

gcggtgcggt cggatgaggc ggtctatgga aaaggagcga agcggacggt tcctgatgaa   1320

ccgacgcttg ccgagcatct cgcccgcaag gcggcggcca tttgggcgct tgaagagccg   1380

ttgatggacg aactgcgccg caacgaacaa gatcggctgc tgaccgagct cgaacagccg   1440

ctggctggca ttttggccaa tatggaattt actggagtga aagtggacac gaagcggctt   1500

gaacagatgg gggcggagct caccgagcag ctgcaggcgg tcgagcggcg catttacgaa   1560

ctcgccggcc aagagttcaa cattaactcg ccgaaacagc tcgggacggt tttatttgac   1620

aagctgcagc tcccggtgtt gaaaaagaca aaaaccggct attcgacttc agccgatgtg   1680

cttgagaagc ttgcaccgca ccatgaaatc gtcgaacata ttttgcatta ccgccaactc   1740

ggcaagctgc agtcaacgta tattgaaggg ctgctgaaag tggtgcaccc cgtgacgggc   1800

aaagtgcaca cgatgttcaa tcaggcgttg acgcaaaccg ggcgcctcag ctccgtcgaa   1860

ccgaatttgc aaaacattcc gattcggctt gaggaagggc ggaaaatccg ccaggcgttc   1920

gtgccgtcgg agccggactg gctcatcttt gcggccgact attcgcaaat cgagctgcgc   1980

gtcctcgccc atatcgcgga agatgacaat ttgattgaag cgttccggcg cgggttggac   2040
```

-continued

```
atccatacga aaacagccat ggacattttc catgtgagcg aagaagacgt gacagccaac   2100

atgcgccgcc aagcgaaggc cgtcaatttt ggcatcgtgt acggcattag tgattacggt   2160

ctggcgcaaa acttgaacat tacgcgcaaa gaagcggctg aatttattga gcgatatttt   2220

gccagttttc caggtgtaaa gcaatatatg gacaacactg tgcaagaagc gaaacaaaaa   2280

gggtatgtga cgacgctgct gcatcggcgc cgctatttgc ccgatattac aagccgcaac   2340

ttcaacgtcc gcagcttcgc cgagcggacg gcgatgaaca caccgattca agggagcgcc   2400

gctgatatta ttaaaaaagc gatgatcgat ctaagcgtga ggctgcgcga agaacggctg   2460

caggcgcgcc tgttgctgca agtgcatgac gaactcattt tggaggcgcc gaaagaggaa   2520

atcgagcggc tgtgccgcct cgttccagag gtgatggagc aagccgtcgc actccgcgtg   2580

ccgctgaaag tcgattacca ttacggtccg acgtggtacg acgccaaata a            2631
```

```
<210> SEQ ID NO 2
<211> LENGTH: 876
<212> TYPE: PRT
<213> ORGANISM: Thermoactinomyces vulgaris

<400> SEQUENCE: 2

Leu Lys Asn Lys Leu Val Leu Ile Asp Gly Asn Ser Val Ala Tyr Arg
  1               5                  10                  15

Ala Phe Phe Ala Leu Pro Leu Leu His Asn Asp Lys Gly Ile His Thr
             20                  25                  30

Asn Ala Val Tyr Gly Phe Thr Met Met Leu Asn Lys Ile Leu Ala Glu
         35                  40                  45

Glu Gln Pro Thr His Ile Leu Val Ala Phe Asp Ala Gly Lys Thr Thr
     50                  55                  60

Phe Arg His Glu Thr Phe Gln Asp Tyr Lys Gly Gly Arg Gln Gln Thr
 65                  70                  75                  80

Pro Pro Glu Leu Ser Glu Gln Phe Pro Leu Leu Arg Glu Leu Leu Lys
                 85                  90                  95

Ala Tyr Arg Ile Pro Ala Tyr Glu Leu Asp His Tyr Glu Ala Asp Asp
            100                 105                 110

Ile Ile Gly Thr Met Ala Ala Arg Ala Glu Arg Glu Gly Phe Ala Val
        115                 120                 125

Lys Val Ile Ser Gly Asp Arg Asp Leu Thr Gln Leu Ala Ser Pro Gln
    130                 135                 140

Val Thr Val Glu Ile Thr Lys Lys Gly Ile Thr Asp Ile Glu Ser Tyr
145                 150                 155                 160

Thr Pro Glu Thr Val Ala Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
        195                 200                 205

Gly Thr Val Glu Asn Val Leu Ala Ser Ile Asp Glu Ile Lys Gly Glu
    210                 215                 220

Lys Leu Lys Glu Asn Leu Arg Gln Tyr Arg Asp Leu Ala Leu Leu Ser
225                 230                 235                 240

Lys Gln Leu Ala Ala Ile Arg Arg Asp Ala Pro Val Glu Leu Thr Leu
                245                 250                 255

Asp Asp Ile Val Tyr Lys Gly Glu Asp Arg Glu Lys Val Val Ala Leu
            260                 265                 270
```

-continued

```
Phe Lys Glu Leu Gly Phe Gln Ser Phe Leu Asp Lys Met Ala Val Gln
        275                 280                 285

Thr Asp Glu Gly Glu Lys Pro Leu Ala Gly Met Asp Phe Ala Ile Ala
    290                 295                 300

Asp Gly Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
                325                 330                 335

Leu Ala Asn Glu Arg Gly Arg Phe Phe Leu Arg Pro Glu Thr Ala Leu
            340                 345                 350

Ala Asp Pro Lys Phe Leu Ala Trp Leu Gly Asp Glu Thr Lys Lys Lys
        355                 360                 365

Thr Met Phe Asp Ser Lys Arg Ala Ala Val Ala Leu Lys Trp Lys Gly
    370                 375                 380

Ile Glu Leu Arg Gly Val Val Phe Asp Leu Leu Leu Ala Ala Tyr Leu
385                 390                 395                 400

Leu Asp Pro Ala Gln Ala Ala Gly Asp Val Ala Ala Val Ala Lys Met
                405                 410                 415

His Gln Tyr Glu Ala Val Arg Ser Asp Glu Ala Val Tyr Gly Lys Gly
            420                 425                 430

Ala Lys Arg Thr Val Pro Asp Glu Pro Thr Leu Ala Glu His Leu Ala
        435                 440                 445

Arg Lys Ala Ala Ala Ile Trp Ala Leu Glu Glu Pro Leu Met Asp Glu
    450                 455                 460

Leu Arg Arg Asn Glu Gln Asp Arg Leu Leu Thr Glu Leu Glu Gln Pro
465                 470                 475                 480

Leu Ala Gly Ile Leu Ala Asn Met Glu Phe Thr Gly Val Lys Val Asp
                485                 490                 495

Thr Lys Arg Leu Glu Gln Met Gly Ala Glu Leu Thr Glu Gln Leu Gln
            500                 505                 510

Ala Val Glu Arg Arg Ile Tyr Glu Leu Ala Gly Gln Glu Phe Asn Ile
        515                 520                 525

Asn Ser Pro Lys Gln Leu Gly Thr Val Leu Phe Asp Lys Leu Gln Leu
    530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu His Ile Leu His
                565                 570                 575

Tyr Arg Gln Leu Gly Lys Leu Gln Ser Thr Tyr Ile Glu Gly Leu Leu
            580                 585                 590

Lys Val Val His Pro Val Thr Gly Lys Val His Thr Met Phe Asn Gln
        595                 600                 605

Ala Leu Thr Gln Thr Gly Arg Leu Ser Ser Val Glu Pro Asn Leu Gln
    610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Glu Asp Asp Asn Leu Ile
            660                 665                 670

Glu Ala Phe Arg Arg Gly Leu Asp Ile His Thr Lys Thr Ala Met Asp
        675                 680                 685
```

-continued

```
Ile Phe His Val Ser Glu Glu Asp Val Thr Ala Asn Met Arg Arg Gln
    690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
            740                 745                 750

Thr Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
    770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
                805                 810                 815

Glu Glu Arg Leu Gln Ala Arg Leu Leu Leu Gln Val His Asp Glu Leu
            820                 825                 830

Ile Leu Glu Ala Pro Lys Glu Glu Ile Glu Arg Leu Cys Arg Leu Val
        835                 840                 845

Pro Glu Val Met Glu Gln Ala Val Ala Leu Arg Val Pro Leu Lys Val
    850                 855                 860

Asp Tyr His Tyr Gly Pro Thr Trp Tyr Asp Ala Lys
865                 870                 875


<210> SEQ ID NO 3
<211> LENGTH: 1779
<212> TYPE: DNA
<213> ORGANISM: Thermoactinomyces vulgaris

<400> SEQUENCE: 3

atggccgtcc aaacggatga aggcgagaag ccgctcgccg ggatggactt tgcgatcgcc      60

gacggcgtca cggacgaaat gctcgccgac aaggcggccc tcgtcgtgga ggtggtgggc     120

gacaactatc accatgcccc gattgtcggg atcgccttgg ccaacgaacg cgggcggttt     180

ttcctgcgcc cggagacggc gctcgccgat ccgaaatttc tcgcttggct tggcgatgag     240

acgaagaaaa aaacgatgtt tgattcaaag cgggcggccg tcgcgttaaa atggaaagga     300

atcgaactgc gcggcgtcgt gttcgatctg ttgctggccg cttacttgct cgatccggcg     360

caggcggcgg gcgacgttgc cgcggtggcg aaaatgcatc agtacgaggc ggtgcggtcg     420

gatgaggcgg tctatggaaa aggagcgaag cggacggttc ctgatgaacc gacgcttgcc     480

gagcatctcg cccgcaaggc ggcggccatt tgggcgcttg aagagccgtt gatggacgaa     540

ctgcgccgca acgaacaaga tcggctgctg accgagctcg aacagccgct ggctggcatt     600

ttggccaata tggaatttac tggagtgaaa gtggacacga agcggcttga acagatgggg     660

gcggagctca ccgagcagct gcaggcggtc gagcggcgca tttacgaact cgccggccaa     720

gagttcaaca ttaactcgcc gaaacagctc gggacggttt tatttgacaa gctgcagctc     780

ccggtgttga aaaagacaaa aaccggctat tcgacttcag ccgatgtgct tgagaagctt     840

gcaccgcacc atgaaatcgt cgaacatatt ttgcattacc gccaactcgg caagctgcag     900

tcaacgtata ttgaagggct gctgaaagtg gtgcaccccg tgacgggcaa agtgcacacg     960

atgttcaatc aggcgttgac gcaaaccggg cgcctcagct ccgtcgaacc gaatttgcaa    1020

aacattccga ttcggcttga ggaagggcgg aaaatccgcc aggcgttcgt gccgtcggag    1080
```

-continued

```
ccggactggc tcatctttgc ggccgactat tcgcaaatcg agctgcgcgt cctcgcccat   1140

atcgcggaag atgacaattt gattgaagcg ttccggcgcg ggttggacat ccatacgaaa   1200

acagccatgg acattttcca tgtgagcgaa gaagacgtga cagccaacat gcgccgccaa   1260

gcgaaggccg tcaattttgg catcgtgtac ggcattagtg attacggtct ggcgcaaaac   1320

ttgaacatta cgcgcaaaga agcggctgaa tttattgagc gatattttgc cagttttcca   1380

ggtgtaaagc aatatatgga caacactgtg caagaagcga aacaaaaagg gtatgtgacg   1440

acgctgctgc atcggcgccg ctatttgccc gatattacaa gccgcaactt caacgtccgc   1500

agcttcgccg agcggacggc gatgaacaca ccgattcaag ggagcgccgc tgatattatt   1560

aaaaaagcga tgatcgatct aagcgtgagg ctgcgcgaag aacggctgca ggcgcgcctg   1620

ttgctgcaag tgcatgacga actcattttg gaggcgccga aagaggaaat cgagcggctg   1680

tgccgcctcg ttccagaggt gatggagcaa gccgtcgcac tccgcgtgcc gctgaaagtc   1740

gattaccatt acggtccgac gtggtacgac gccaaataa                           1779
```

```
<210> SEQ ID NO 4
<211> LENGTH: 592
<212> TYPE: PRT
<213> ORGANISM: Thermoactinomyces vulgaris

<400> SEQUENCE: 4

Met Ala Val Gln Thr Asp Glu Gly Glu Lys Pro Leu Ala Gly Met Asp
  1               5                  10                  15

Phe Ala Ile Ala Asp Gly Val Thr Asp Glu Met Leu Ala Asp Lys Ala
             20                  25                  30

Ala Leu Val Val Glu Val Val Gly Asp Asn Tyr His His Ala Pro Ile
         35                  40                  45

Val Gly Ile Ala Leu Ala Asn Glu Arg Gly Arg Phe Phe Leu Arg Pro
     50                  55                  60

Glu Thr Ala Leu Ala Asp Pro Lys Phe Leu Ala Trp Leu Gly Asp Glu
 65                  70                  75                  80

Thr Lys Lys Lys Thr Met Phe Asp Ser Lys Arg Ala Ala Val Ala Leu
                 85                  90                  95

Lys Trp Lys Gly Ile Glu Leu Arg Gly Val Val Phe Asp Leu Leu Leu
            100                 105                 110

Ala Ala Tyr Leu Leu Asp Pro Ala Gln Ala Ala Gly Asp Val Ala Ala
        115                 120                 125

Val Ala Lys Met His Gln Tyr Glu Ala Val Arg Ser Asp Glu Ala Val
    130                 135                 140

Tyr Gly Lys Gly Ala Lys Arg Thr Val Pro Asp Glu Pro Thr Leu Ala
145                 150                 155                 160

Glu His Leu Ala Arg Lys Ala Ala Ala Ile Trp Ala Leu Glu Glu Pro
                165                 170                 175

Leu Met Asp Glu Leu Arg Arg Asn Glu Gln Asp Arg Leu Leu Thr Glu
            180                 185                 190

Leu Glu Gln Pro Leu Ala Gly Ile Leu Ala Asn Met Glu Phe Thr Gly
        195                 200                 205

Val Lys Val Asp Thr Lys Arg Leu Glu Gln Met Gly Ala Glu Leu Thr
    210                 215                 220

Glu Gln Leu Gln Ala Val Glu Arg Arg Ile Tyr Glu Leu Ala Gly Gln
225                 230                 235                 240

Glu Phe Asn Ile Asn Ser Pro Lys Gln Leu Gly Thr Val Leu Phe Asp
```

-continued

```
                245                 250                 255

Lys Leu Gln Leu Pro Val Leu Lys Lys Thr Lys Thr Gly Tyr Ser Thr
            260                 265                 270

Ser Ala Asp Val Leu Glu Lys Leu Ala Pro His His Glu Ile Val Glu
        275                 280                 285

His Ile Leu His Tyr Arg Gln Leu Gly Lys Leu Gln Ser Thr Tyr Ile
    290                 295                 300

Glu Gly Leu Leu Lys Val Val His Pro Val Thr Gly Lys Val His Thr
305                 310                 315                 320

Met Phe Asn Gln Ala Leu Thr Gln Thr Gly Arg Leu Ser Ser Val Glu
                325                 330                 335

Pro Asn Leu Gln Asn Ile Pro Ile Arg Leu Glu Glu Gly Arg Lys Ile
            340                 345                 350

Arg Gln Ala Phe Val Pro Ser Glu Pro Asp Trp Leu Ile Phe Ala Ala
        355                 360                 365

Asp Tyr Ser Gln Ile Glu Leu Arg Val Leu Ala His Ile Ala Glu Asp
    370                 375                 380

Asp Asn Leu Ile Glu Ala Phe Arg Arg Gly Leu Asp Ile His Thr Lys
385                 390                 395                 400

Thr Ala Met Asp Ile Phe His Val Ser Glu Glu Asp Val Thr Ala Asn
                405                 410                 415

Met Arg Arg Gln Ala Lys Ala Val Asn Phe Gly Ile Val Tyr Gly Ile
            420                 425                 430

Ser Asp Tyr Gly Leu Ala Gln Asn Leu Asn Ile Thr Arg Lys Glu Ala
        435                 440                 445

Ala Glu Phe Ile Glu Arg Tyr Phe Ala Ser Phe Pro Gly Val Lys Gln
    450                 455                 460

Tyr Met Asp Asn Thr Val Gln Glu Ala Lys Gln Lys Gly Tyr Val Thr
465                 470                 475                 480

Thr Leu Leu His Arg Arg Arg Tyr Leu Pro Asp Ile Thr Ser Arg Asn
                485                 490                 495

Phe Asn Val Arg Ser Phe Ala Glu Arg Thr Ala Met Asn Thr Pro Ile
            500                 505                 510

Gln Gly Ser Ala Ala Asp Ile Ile Lys Lys Ala Met Ile Asp Leu Ser
        515                 520                 525

Val Arg Leu Arg Glu Glu Arg Leu Gln Ala Arg Leu Leu Leu Gln Val
    530                 535                 540

His Asp Glu Leu Ile Leu Glu Ala Pro Lys Glu Glu Ile Glu Arg Leu
545                 550                 555                 560

Cys Arg Leu Val Pro Glu Val Met Glu Gln Ala Val Ala Leu Arg Val
                565                 570                 575

Pro Leu Lys Val Asp Tyr His Tyr Gly Pro Thr Trp Tyr Asp Ala Lys
            580                 585                 590
```

<210> SEQ ID NO 5
<211> LENGTH: 1767
<212> TYPE: DNA
<213> ORGANISM: Thermoactinomyces vulgaris

<400> SEQUENCE: 5

```
atggatgaag gcgagaagcc gctcgccggg atggactttg cgatcgccga cggcgtcacg     60

gacgaaatgc tcgccgacaa ggcggccctc gtcgtggagg tggtgggcga caactatcac    120

catgccccga ttgtcgggat cgccttggcc aacgaacgcg ggcggttttt cctgcgcccg    180
```

```
gagacggcgc tcgccgatcc gaaatttctc gcttggcttg gcgatgagac gaagaaaaaa    240

acgatgtttg attcaaagcg ggcggccgtc gcgttaaaat ggaaaggaat cgaactgcgc    300

ggcgtcgtgt tcgatctgtt gctggccgct tacttgctcg atccggcgca ggcggcgggc    360

gacgttgccg cggtggcgaa aatgcatcag tacgaggcgg tgcggtcgga tgaggcggtc    420

tatggaaaag gagcgaagcg gacggttcct gatgaaccga cgcttgccga gcatctcgcc    480

cgcaaggcgg cggccatttg ggcgcttgaa gagccgttga tggacgaact gcgccgcaac    540

gaacaagatc ggctgctgac cgagctcgaa cagccgctgg ctggcatttt ggccaatatg    600

gaatttactg gagtgaaagt ggacacgaag cggcttgaac agatgggggc ggagctcacc    660

gagcagctgc aggcggtcga gcggcgcatt tacgaactcg ccggccaaga gttcaacatt    720

aactcgccga aacagctcgg gacggtttta tttgacaagc tgcagctccc ggtgttgaaa    780

aagacaaaaa ccggctattc gacttcagcc gatgtgcttg agaagcttgc accgcaccat    840

gaaatcgtcg aacatatttt gcattaccgc caactcggca agctgcagtc aacgtatatt    900

gaagggctgc tgaaagtggt gcaccccgtg acgggcaaag tgcacacgat gttcaatcag    960

gcgttgacgc aaaccgggcg cctcagctcc gtcgaaccga atttgcaaaa cattccgatt   1020

cggcttgagg aagggcggaa aatccgccag gcgttcgtgc cgtcggagcc ggactggctc   1080

atctttgcgg ccgactattc gcaaatcgag ctgcgcgtcc tcgcccatat cgcggaagat   1140

gacaatttga ttgaagcgtt ccggcgcggg ttggacatcc atacgaaaac agccatggac   1200

attttccatg tgagcgaaga agacgtgaca gccaacatgc gccgccaagc gaaggccgtc   1260

aattttggca tcgtgtacgg cattagtgat tacggtctgg cgcaaaactt gaacattacg   1320

cgcaaagaag cggctgaatt tattgagcga tattttgcca gttttccagg tgtaaagcaa   1380

tatatggaca acactgtgca agaagcgaaa caaaaagggt atgtgacgac gctgctgcat   1440

cggcgccgct atttgcccga tattacaagc cgcaacttca acgtccgcag cttcgccgag   1500

cggacggcga tgaacacacc gattcaaggg agcgccgctg atattattaa aaaagcgatg   1560

atcgatctaa gcgtgaggct gcgcgaagaa cggctgcagg cgcgcctgtt gctgcaagtg   1620

catgacgaac tcattttgga ggcgccgaaa gaggaaatcg agcggctgtg ccgcctcgtt   1680

ccagaggtga tggagcaagc cgtcgcactc cgcgtgccgc tgaaagtcga ttaccattac   1740

ggtccgacgt ggtacgacgc caaataa                                       1767
```

```
<210> SEQ ID NO 6
<211> LENGTH: 588
<212> TYPE: PRT
<213> ORGANISM: Thermoactinomyces vulgaris

<400> SEQUENCE: 6

Thr Asp Glu Gly Glu Lys Pro Leu Ala Gly Met Asp Phe Ala Ile Ala
  1               5                  10                  15

Asp Gly Val Thr Asp Glu Met Leu Ala Asp Lys Ala Ala Leu Val Val
             20                  25                  30

Glu Val Val Gly Asp Asn Tyr His His Ala Pro Ile Val Gly Ile Ala
         35                  40                  45

Leu Ala Asn Glu Arg Gly Arg Phe Phe Leu Arg Pro Glu Thr Ala Leu
     50                  55                  60

Ala Asp Pro Lys Phe Leu Ala Trp Leu Gly Asp Glu Thr Lys Lys Lys
 65                  70                  75                  80

Thr Met Phe Asp Ser Lys Arg Ala Ala Val Ala Leu Lys Trp Lys Gly
                 85                  90                  95
```

-continued

```
Ile Glu Leu Arg Gly Val Val Phe Asp Leu Leu Leu Ala Ala Tyr Leu
            100                 105                 110

Leu Asp Pro Ala Gln Ala Ala Gly Asp Val Ala Ala Val Ala Lys Met
        115                 120                 125

His Gln Tyr Glu Ala Val Arg Ser Asp Glu Ala Val Tyr Gly Lys Gly
    130                 135                 140

Ala Lys Arg Thr Val Pro Asp Glu Pro Thr Leu Ala Glu His Leu Ala
145                 150                 155                 160

Arg Lys Ala Ala Ala Ile Trp Ala Leu Glu Glu Pro Leu Met Asp Glu
                165                 170                 175

Leu Arg Arg Asn Glu Gln Asp Arg Leu Leu Thr Glu Leu Glu Gln Pro
            180                 185                 190

Leu Ala Gly Ile Leu Ala Asn Met Glu Phe Thr Gly Val Lys Val Asp
        195                 200                 205

Thr Lys Arg Leu Glu Gln Met Gly Ala Glu Leu Thr Glu Gln Leu Gln
    210                 215                 220

Ala Val Glu Arg Arg Ile Tyr Glu Leu Ala Gly Gln Glu Phe Asn Ile
225                 230                 235                 240

Asn Ser Pro Lys Gln Leu Gly Thr Val Leu Phe Asp Lys Leu Gln Leu
                245                 250                 255

Pro Val Leu Lys Lys Thr Lys Thr Gly Tyr Ser Thr Ser Ala Asp Val
            260                 265                 270

Leu Glu Lys Leu Ala Pro His His Glu Ile Val Glu His Ile Leu His
        275                 280                 285

Tyr Arg Gln Leu Gly Lys Leu Gln Ser Thr Tyr Ile Glu Gly Leu Leu
    290                 295                 300

Lys Val Val His Pro Val Thr Gly Lys Val His Thr Met Phe Asn Gln
305                 310                 315                 320

Ala Leu Thr Gln Thr Gly Arg Leu Ser Ser Val Glu Pro Asn Leu Gln
                325                 330                 335

Asn Ile Pro Ile Arg Leu Glu Glu Gly Arg Lys Ile Arg Gln Ala Phe
            340                 345                 350

Val Pro Ser Glu Pro Asp Trp Leu Ile Phe Ala Ala Asp Tyr Ser Gln
        355                 360                 365

Ile Glu Leu Arg Val Leu Ala His Ile Ala Glu Asp Asp Asn Leu Ile
    370                 375                 380

Glu Ala Phe Arg Arg Gly Leu Asp Ile His Thr Lys Thr Ala Met Asp
385                 390                 395                 400

Ile Phe His Val Ser Glu Glu Asp Val Thr Ala Asn Met Arg Arg Gln
                405                 410                 415

Ala Lys Ala Val Asn Phe Gly Ile Val Tyr Gly Ile Ser Asp Tyr Gly
            420                 425                 430

Leu Ala Gln Asn Leu Asn Ile Thr Arg Lys Glu Ala Ala Glu Phe Ile
        435                 440                 445

Glu Arg Tyr Phe Ala Ser Phe Pro Gly Val Lys Gln Tyr Met Asp Asn
    450                 455                 460

Thr Val Gln Glu Ala Lys Gln Lys Gly Tyr Val Thr Thr Leu Leu His
465                 470                 475                 480

Arg Arg Arg Tyr Leu Pro Asp Ile Thr Ser Arg Asn Phe Asn Val Arg
                485                 490                 495

Ser Phe Ala Glu Arg Thr Ala Met Asn Thr Pro Ile Gln Gly Ser Ala
            500                 505                 510
```

-continued

```
Ala Asp Ile Ile Lys Lys Ala Met Ile Asp Leu Ser Val Arg Leu Arg
        515                 520                 525

Glu Glu Arg Leu Gln Ala Arg Leu Leu Leu Gln Val His Asp Glu Leu
    530                 535                 540

Ile Leu Glu Ala Pro Lys Glu Glu Ile Glu Arg Leu Cys Arg Leu Val
545                 550                 555                 560

Pro Glu Val Met Glu Gln Ala Val Ala Leu Arg Val Pro Leu Lys Val
                565                 570                 575

Asp Tyr His Tyr Gly Pro Thr Trp Tyr Asp Ala Lys
            580                 585


<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence:  Synthetic

<400> SEQUENCE: 7

gacgtcgcat gctcct                                                    16


<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 8

accgaattcc tcgagtc                                                   17


<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:  Synthetic
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (24)
<223> OTHER INFORMATION: i

<400> SEQUENCE: 9

tagagcggcc gcgayccnaa yytncaraay at                                  32


<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:  Synthetic
<220> FEATURE:
<221> NAME/KEY: modified_base
<222> LOCATION: (14)..(15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (20)
<223> OTHER INFORMATION: i
<220> FEATURE:
```

-continued

<221> NAME/KEY: modified_base
<222> LOCATION: (30)
<223> OTHER INFORMATION: i

<400> SEQUENCE: 10
ctgcggccgc ctannacnan ytcrtcrtgn ac 32

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 11
gcgcgaagaa cggctgcagg c 21

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (8)..(9)
<223> OTHER INFORMATION: i
<220> FEATURE:
<221> NAME/KEY: modified_base
<222> LOCATION: (15)..(19)
<223> OTHER INFORMATION: i
<220> FEATURE:
<221> NAME/KEY: modified_base
<222> LOCATION: (21)
<223> OTHER INFORMATION: i

<400> SEQUENCE: 12
ttcaaccnna actcnnnnna ncagct 26

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
cggctccgac ggcacgaacg 20

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 14
tcaacaccgg gagctgcagc ttgtca 26

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic

<400> SEQUENCE: 15
catggatgaa ggtgagaagc cactggccgg gatggacttt gcgat 45

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 16
cgcaaagtcc atcccggcca gtggcttctc accttcatc 39

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence: Synthetic

<400> SEQUENCE: 17
aaaccatggc agttcaaacc gatgaaggcg agaaaccact ggctgggatg gactttgcga 60
t 61

<210> SEQ ID NO 18
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 18
cgcaaagtcc atcccagcca gtggtttctc gccttcatcg gtttgaactg ccatggttt 59

<210> SEQ ID NO 19
<211> LENGTH: 17
<212> TYPE: PRT
<213> ORGANISM: Bacillus subtilis

<400> SEQUENCE: 19

Glu Thr Tyr Val Val Phe Asp Val Glu Thr Thr Gly Leu Ser Ala Val
1 5 10 15

Tyr

<210> SEQ ID NO 20
<211> LENGTH: 14
<212> TYPE: PRT
<213> ORGANISM: Bacillus subtilis

<400> SEQUENCE: 20

Leu Val Ala His Asn Ala Ser Phe Asp Met Gly Phe Leu Asn
1 5 10

<210> SEQ ID NO 21
<211> LENGTH: 13
<212> TYPE: PRT
<213> ORGANISM: Bacillus subtilis

<400> SEQUENCE: 21

Thr Leu Cys Lys Lys Phe Asp Ile Glu Leu Thr Gln His
1 5 10

<210> SEQ ID NO 22
<211> LENGTH: 17
<212> TYPE: PRT
<213> ORGANISM: Escherichia coli

<400> SEQUENCE: 22

Thr Arg Gln Ile Val Leu Asp Thr Glu Thr Thr Gly Met Asn Gln Ile
1 5 10 15

Gly

<210> SEQ ID NO 23
<211> LENGTH: 14
<212> TYPE: PRT
<213> ORGANISM: Escherichia coli

<400> SEQUENCE: 23

Leu Val Ile His Asn Ala Ala Phe Asp Ile Gly Phe Met Asp
1 5 10

<210> SEQ ID NO 24
<211> LENGTH: 13
<212> TYPE: PRT
<213> ORGANISM: Escherichia coli

<400> SEQUENCE: 24

Ala Leu Cys Ala Arg Tyr Glu Ile Asp Asn Ser Lys Arg
1 5 10

<210> SEQ ID NO 25
<211> LENGTH: 18
<212> TYPE: PRT
<213> ORGANISM: Escherichia coli

<400> SEQUENCE: 25

Arg Val Ile Tyr Met Pro Phe Asp Asn Glu Arg Asp Met Leu Met Glu
1 5 10 15

Tyr Ile

<210> SEQ ID NO 26
<211> LENGTH: 15
<212> TYPE: PRT
<213> ORGANISM: phage T4

<400> SEQUENCE: 26

Phe Thr Gly Trp Asn Ile Glu Gly Phe Asp Val Pro Tyr Ile Met
1 5 10 15

<210> SEQ ID NO 27
<211> LENGTH: 12
<212> TYPE: PRT
<213> ORGANISM: phage T4

<400> SEQUENCE: 27

Asp Lys Ile Arg Gly Phe Ile Asp Leu Val Leu Ser
1 5 10

<210> SEQ ID NO 28
<211> LENGTH: 15
<212> TYPE: PRT
<213> ORGANISM: phage T7

<400> SEQUENCE: 28

Met Ile Val Ser Asp Ile Glu Ala Asn Ala Leu Leu Glu Ser Val
1 5 10 15

<210> SEQ ID NO 29
<211> LENGTH: 14

-continued

<212> TYPE: PRT
<213> ORGANISM: phage T7

<400> SEQUENCE: 29

Val Phe His Asn Gly His Lys Tyr Asp Val Pro Ala Leu Thr
1 5 10

<210> SEQ ID NO 30
<211> LENGTH: 14
<212> TYPE: PRT
<213> ORGANISM: phage T7

<400> SEQUENCE: 30

Glu Glu Met Met Asp Tyr Asn Val Gln Asp Val Val Val Thr
1 5 10

<210> SEQ ID NO 31
<211> LENGTH: 18
<212> TYPE: PRT
<213> ORGANISM: Escherichia coli

<400> SEQUENCE: 31

Lys Ala Pro Val Phe Ala Phe Asp Thr Glu Thr Asp Ser Leu Asp Asn
1 5 10 15

Ile Ser

<210> SEQ ID NO 32
<211> LENGTH: 13
<212> TYPE: PRT
<213> ORGANISM: Escherichia coli

<400> SEQUENCE: 32

Val Gly Gln Asn Leu Lys Tyr Asp Arg Gly Ile Leu Ala
1 5 10

<210> SEQ ID NO 33
<211> LENGTH: 14
<212> TYPE: PRT
<213> ORGANISM: Escherichia coli

<400> SEQUENCE: 33

Glu Glu Ala Gly Arg Tyr Ala Ala Glu Asp Ala Asp Val Thr
1 5 10

<210> SEQ ID NO 34
<211> LENGTH: 18
<212> TYPE: PRT
<213> ORGANISM: T. maritima

<400> SEQUENCE: 34

Glu Ser Pro Ser Phe Ala Ile Asp Leu Glu Thr Ser Ser Leu Asp Pro
1 5 10 15

Phe Asp

<210> SEQ ID NO 35
<211> LENGTH: 13
<212> TYPE: PRT
<213> ORGANISM: T. maritima

<400> SEQUENCE: 35

Val Gly Gln Asn Leu Lys Phe Asp Tyr Lys Val Leu Met
1 5 10

-continued

```
<210> SEQ ID NO 36
<211> LENGTH: 14
<212> TYPE: PRT
<213> ORGANISM: T. maritima

<400> SEQUENCE: 36

Glu Lys Ala Ala Asn Tyr Ser Cys Glu Asp Ala Asp Ile Thr
  1               5                   10


<210> SEQ ID NO 37
<211> LENGTH: 18
<212> TYPE: PRT
<213> ORGANISM: T. neapolitana

<400> SEQUENCE: 37

Glu Val Pro Ser Phe Ala Leu Asp Leu Glu Thr Ser Ser Leu Asp Pro
  1               5                   10                  15

Phe Asn


<210> SEQ ID NO 38
<211> LENGTH: 13
<212> TYPE: PRT
<213> ORGANISM: T. neapolitana

<400> SEQUENCE: 38

Val Gly Gln Asn Leu Lys Tyr Asp Tyr Lys Val Leu Met
  1               5                   10


<210> SEQ ID NO 39
<211> LENGTH: 14
<212> TYPE: PRT
<213> ORGANISM: T. neapolitana

<400> SEQUENCE: 39

Asp Lys Ala Ala Asn Tyr Ser Cys Glu Asp Ala Asp Ile Thr
  1               5                   10
```